(12) United States Patent
Kapas et al.

(10) Patent No.: US 10,449,296 B2
(45) Date of Patent: Oct. 22, 2019

(54) COMPACT AUTO-INJECTOR

(71) Applicant: Pirouette Medical LLC, Boston, MA (US)

(72) Inventors: Elijah Kapas, Medford, MA (US); Matthew Kane, Somerville, MA (US); Conor Cullinane, Hampton, NH (US)

(73) Assignee: PIROUETTE MEDICAL LLC, Hampton, NH (US)

( * ) Notice: Subject to any disclaimer, the term of this patent is extended or adjusted under 35 U.S.C. 154(b) by 0 days.

(21) Appl. No.: 16/272,628

(22) Filed: Feb. 11, 2019

(65) Prior Publication Data

US 2019/0167905 A1 Jun. 6, 2019

Related U.S. Application Data

(63) Continuation of application No. 16/117,911, filed on Aug. 30, 2018, now Pat. No. 10,265,471.

(Continued)

(51) Int. Cl.
*A61M 5/20* (2006.01)
*A61M 5/46* (2006.01)
(Continued)

(52) U.S. Cl.
CPC ...... *A61M 5/2033* (2013.01); *A61M 5/14244* (2013.01); *A61M 5/14248* (2013.01);
(Continued)

(58) Field of Classification Search
CPC ............ A61M 5/2033; A61M 5/3202; A61M 5/2466; A61M 5/31565; A61M 5/31571;
(Continued)

(56) References Cited

U.S. PATENT DOCUMENTS 2,693,186 A * 11/1954 Riker ............... A61M 5/2033
604/139
3,074,541 A 1/1963 Roehr
(Continued)

FOREIGN PATENT DOCUMENTS

DE 19725203 C2 10/2002
WO WO-1997039787 A1 10/1997
(Continued)

OTHER PUBLICATIONS http://www.enableinjections.com/_(Last Accessed Apr. 8, 2019).
(Continued)

*Primary Examiner* — Nilay J Shah
(74) *Attorney, Agent, or Firm* — Goodwin Procter LLP

(57) ABSTRACT

A novel single use auto-injector for delivering a fixed amount of medicament is described. The auto-injector may include a sealed housing rotatably held in a cover. Once the auto-injector is positioned at the injection location, the user can transition the housing from a locked to an armed position. The user can then compress the sealed housing into the cover, triggering activation mechanisms that initiate the injection. A first activation mechanism engages an interlock to prevent reuse of the auto-injector. A second activation mechanism straightens and extends a curved needle to a set the exposed needle length. A third activation mechanism pierces a sealed reservoir allowing the medicament to be forced through the injection needle. Following the injection, the auto-injector expands and interlocks, retracting the needle into the auto-injector and preventing reuse.

30 Claims, 88 Drawing Sheets

Related U.S. Application Data

(60) Provisional application No. 62/568,567, filed on Oct. 5, 2017, provisional application No. 62/552,052, filed on Aug. 30, 2017.

(51) Int. Cl.
  *A61M 5/142* (2006.01)
  *A61M 5/32* (2006.01)
  *A61M 5/24* (2006.01)
  *A61M 5/315* (2006.01)

(52) U.S. Cl.
  CPC ............... *A61M 5/20* (2013.01); *A61M 5/46* (2013.01); *A61M 5/24* (2013.01); *A61M 5/2466* (2013.01); *A61M 5/3158* (2013.01); *A61M 5/31565* (2013.01); *A61M 5/31571* (2013.01); *A61M 5/3202* (2013.01); *A61M 5/3232* (2013.01); *A61M 2005/14284* (2013.01); *A61M 2005/206* (2013.01); *A61M 2005/2073* (2013.01)

(58) Field of Classification Search
  CPC .............. A61M 5/3158; A61M 5/3243; A61M 5/3232; A61M 5/46; A61M 2005/2073
  See application file for complete search history.

(56) References Cited

U.S. PATENT DOCUMENTS

| | | | |
|---|---|---|---|
| 3,368,558 A * | 2/1968 | Sarnoff | A61M 5/24 604/198 |
| 4,287,943 A | 9/1981 | Hotta | |
| 4,429,793 A | 2/1984 | Ehmann | |
| 4,573,581 A | 3/1986 | Galloway et al. | |
| 4,738,364 A | 4/1988 | Yeager | |
| 5,015,235 A | 5/1991 | Crossman | |
| 5,361,603 A | 11/1994 | Merritt-Munson | |
| 5,390,791 A | 2/1995 | Yeager | |
| 5,405,012 A | 4/1995 | Shindler et al. | |
| 5,658,259 A | 8/1997 | Pearson et al. | |
| 5,714,217 A | 2/1998 | Andersen et al. | |
| 5,858,001 A | 1/1999 | Tsals et al. | |
| 5,950,827 A | 9/1999 | Odom et al. | |
| 5,983,661 A | 11/1999 | Wiesman | |
| 6,086,562 A | 7/2000 | Jacobsen et al. | |
| 6,336,340 B1 | 1/2002 | Laby | |
| 6,405,556 B1 | 6/2002 | Bucholz | |
| 6,508,391 B2 | 1/2003 | Gilbert | |
| 6,595,362 B2 | 7/2003 | Penney et al. | |
| 6,605,067 B1 * | 8/2003 | Larsen | A61M 5/3287 604/192 |
| 6,780,426 B2 | 8/2004 | Zhang et al. | |
| 6,935,133 B2 | 8/2005 | Keeter et al. | |
| 6,984,222 B1 | 1/2006 | Hitchins et al. | |
| 7,047,983 B2 | 5/2006 | Manougian et al. | |
| 7,434,686 B2 | 10/2008 | Prindle | |
| 7,597,196 B2 | 10/2009 | Langone | |
| 7,686,786 B2 | 3/2010 | Moller et al. | |
| 8,137,314 B2 | 3/2012 | Mounce et al. | |
| 8,152,771 B2 | 4/2012 | Mogensen et al. | |
| 8,298,173 B2 | 10/2012 | Bates et al. | |
| 8,323,250 B2 | 12/2012 | Chong et al. | |
| 8,517,988 B2 | 8/2013 | Smith | |
| 8,684,968 B2 | 4/2014 | Genosar | |
| 8,734,396 B2 | 5/2014 | Wyss | |
| 8,753,310 B2 | 6/2014 | Sullivan et al. | |
| 8,932,254 B2 | 1/2015 | Eaton | |
| 9,072,838 B2 | 7/2015 | Hogdahl | |
| 9,096,364 B2 | 8/2015 | Rust et al. | |
| 9,168,337 B2 | 10/2015 | Miyazaki | |
| 9,174,002 B2 | 11/2015 | Chang et al. | |
| 9,220,837 B2 | 12/2015 | Pesach et al. | |
| 9,227,023 B2 | 1/2016 | Kraft | |
| 9,381,294 B2 | 7/2016 | Ziegner | |
| 9,408,984 B2 | 8/2016 | Durack et al. | |
| 9,480,792 B2 | 11/2016 | Constantineau et al. | |
| 9,486,616 B2 | 11/2016 | Eppstein et al. | |
| 9,533,105 B2 | 1/2017 | Veasey et al. | |
| 9,590,683 B2 | 3/2017 | Greiner | |
| 9,597,450 B2 | 3/2017 | Cindrich et al. | |
| 9,707,156 B2 | 7/2017 | Wengreen et al. | |
| 9,750,892 B2 | 9/2017 | Radmer et al. | |
| 2002/0091357 A1 | 7/2002 | Trautman et al. | |
| 2004/0211806 A1 | 10/2004 | Wilkerson et al. | |
| 2005/0222539 A1 | 10/2005 | Gonzales et al. | |
| 2005/0279664 A1 | 12/2005 | Hommann | |
| 2007/0125677 A1 | 6/2007 | Oronsky et al. | |
| 2008/0295833 A1 | 12/2008 | Rohrschneider et al. | |
| 2010/0187270 A1 | 7/2010 | Puglisi | |
| 2010/0270315 A1 | 10/2010 | Davis | |
| 2010/0282762 A1 | 11/2010 | Leonard | |
| 2011/0083445 A1 | 4/2011 | Heyd et al. | |
| 2011/0202011 A1 * | 8/2011 | Wozencroft | A61M 5/2033 604/192 |
| 2011/0276027 A1 | 11/2011 | Trautman et al. | |
| 2012/0191102 A1 | 7/2012 | Matsumoto et al. | |
| 2012/0310175 A1 | 12/2012 | Vedrine et al. | |
| 2014/0088508 A1 | 3/2014 | Ryan et al. | |
| 2014/0090997 A1 | 4/2014 | Dasbach et al. | |
| 2014/0138402 A1 | 5/2014 | Warren et al. | |
| 2014/0142507 A1 | 5/2014 | Armes | |
| 2014/0166528 A1 | 6/2014 | Bianchi | |
| 2014/0309591 A1 | 10/2014 | Holmqvist | |
| 2015/0314117 A1 | 11/2015 | Arami et al. | |
| 2015/0343151 A1 | 12/2015 | Stefansen | |
| 2016/0030284 A1 | 2/2016 | Vedrine | |
| 2016/0038689 A1 | 2/2016 | Lee et al. | |
| 2016/0082189 A1 | 3/2016 | Anderson et al. | |
| 2016/0175524 A1 | 6/2016 | Henderson et al. | |
| 2016/0237752 A1 | 8/2016 | Jones | |
| 2016/0287791 A1 | 10/2016 | Olson | |
| 2016/0296710 A1 | 10/2016 | Bainton et al. | |
| 2017/0056579 A1 | 3/2017 | Muri | |
| 2017/0143896 A1 | 5/2017 | Lorenzen et al. | |
| 2017/0143900 A1 | 5/2017 | Rioux et al. | |
| 2017/0175859 A1 | 6/2017 | Brockmeier | |
| 2017/0209643 A1 | 7/2017 | Geipel et al. | |

FOREIGN PATENT DOCUMENTS

| | | |
|---|---|---|
| WO | WO-2007051563 A1 | 5/2007 |
| WO | WO-2009062510 A1 | 5/2009 |
| WO | WO-2011012849 A1 | 2/2011 |
| WO | WO-2012058192 A1 | 5/2012 |
| WO | WO-2013147440 A1 | 10/2013 |
| WO | WO-2014072993 A3 | 7/2014 |
| WO | WO-2015/117913 A1 | 8/2015 |
| WO | WO-2016055505 A1 | 4/2016 |
| WO | WO-2017/004315 A1 | 1/2017 |
| WO | WO-2017072333 A1 | 5/2017 |
| WO | WO-2017083622 A1 | 5/2017 |
| WO | WO-2017118681 A1 | 7/2017 |

OTHER PUBLICATIONS http://www.enableinjections.com/ (2017).
International Search Report and Written Opinion dated Nov. 15, 2018 for International Application No. PCT/US2018/048878, 15 pages.
https://exposingmodernmugwumps.com/2015/04/13/the-epibracelet-a-wearable-portable-and-fashionable-automatic-epinephrine-injection-device/_(Last Accessed Apr. 5, 2019).

* cited by examiner

| Parameter | Exemplary Value Range | Units |
|---|---|---|
| Needle Diameter | 15-34 | Gage |
| Width/Height Ratio | 1-10 | - |
| Needle Injection Depth | 2.5-32 | mm |
| User Compression Force | ≤100 | N |
| Vial Volume | ≤5 | mL |
| Injection Time | ≤15 | s |
| Expansion/Collapsed Height Ratio | 1.25-3 | - |
| Torsion Spring Torque | ≤1000 | N-mm |
| Compression Spring Rate | ≤10 | N/mm |
| Collapsed Height | ≤80 | mm |
| Water-resistant | ≤7.5 | m |
| Injection Needle Rotation Angle | ≥2 | deg |
| Housing Rotation Relative to Cover | ≤180 | deg |
| Material | Thermoplastics, Composites, Metals | - |
| Dosing | Fixed Single-Dose | - |
| Mass of Device | ≤0.4 | kg |

FIG. 141

COMPACT AUTO-INJECTOR

CROSS-REFERENCE TO RELATED APPLICATION

This application is a continuation of and claims the benefit of priority to U.S. patent application Ser. No. 16/117,911 entitled "Compact Auto-Injector," filed on Aug. 30, 2018, which claims the benefit of priority to U.S. Provisional Patent Application No. 62/552,052 entitled "Compact Auto-Injector," filed on Aug. 30, 2017, and U.S. Provisional Patent Application No. 62/568,567 entitled "Protective Case for an Auto-Injector," filed on Oct. 5, 2017, the contents of all of which are incorporated herein by reference in their entireties.

TECHNICAL FIELD

The invention relates generally to medicament auto-injectors and, more particularly, to an auto-injector of a relatively low profile and high aspect ratio. The auto-injector allows for administration of a desired dose of medicament intramuscularly or subcutaneously.

BACKGROUND

The auto-injector market is growing rapidly through an increase in prescriptions, along with new indications for use. Auto-injectors are becoming more dominant as they provide an innovative approach to administer drugs or biological products, and they may enhance safety, improve dosing accuracy, and increase patient compliance, particularly in self-administration settings.

Existing auto-injectors leave patients actively seeking an alternative to address the anxiety they feel associated with existing pain points; poor portability, unwanted attention, accidental injections, and lacerations. An improved auto-injector is needed.

SUMMARY OF THE INVENTION

Through a human-centered design focus, embodiments of the auto-injector described herein are portable, intuitive, and easy-to-use. The auto-injector technology is diversely applicable to many indications for uses that require fixed dose, single-use intramuscular or subcutaneous injections. Embodiments of the auto-injector are designed to consider the human element. The enhanced ergonomics of embodiments of the device, in combination with the high aspect ratio injector technology, are designed to match modern lifestyles. Embodiments of the invention include a high aspect ratio auto-injector technology that enables the creation of a portable as well as wearable auto-injector for safe and effective dosing of epinephrine, and other medicaments (note that the exemplary value ranges in the chart of FIG. 141 relate to the delivery of multiple medicaments, but can be adjusted, as necessary, to accommodate the delivery of other medicaments). FIG. 1 provides example illustrations of how the aspect ratio of an auto-injector is calculated, using both conventional auto-injectors and the inventive auto-injector described herein. As used herein, and with reference to FIG. 1, height (H) is defined as the largest straight-line length of the auto-injector away from the skin during injection (perpendicular to the injection surface), and width (W) is measured as the smallest straight-line length on the surface that is in contact with a patient's skin during injection (parallel to the injection surface).

The novel auto-injector technology can be readily incorporated into an auto-injector that can be worn in a bracelet, pendant or other accessory to ensure that the auto-injector is always within reach in the event of an emergency. The objectives of a portable and wearable auto-injector that is safe, easy to use, as well as other objectives, will be apparent to those skilled in the art.

In one aspect, the invention is a compact auto-injector for delivering a medicament dose subcutaneously or intramuscularly. The auto-injector may be composed of two main components: a sealed housing, and a cover. Disposed inside the sealed housing is a medicament reservoir containing the medicament, a medicament dispensing system (MDS) and a needle extension system (NES). Upon time of injection, the medicament reservoir and needle extension system are in fluidic connection.

The sealed housing may be rotatably retained in a cover. In one embodiment, the sealed housing may be rotated relative to the cover from an initial position, to a second position following a user input through a designed interface. At least one of the components comprising the sealed housing or the cover may include indicia indicating the first, second, or subsequent positions. The sealed housing may be bounded during the transition such that the sealed housing may be displaced relative to the cover in a controlled means. The auto-injector can further include a biasing member, whose function includes displacing the sealed housing relative to the cover. In various embodiments, the biasing member can be a spring that is integrally formed with the sealed housing or cover or conversely a separate component which can be disposed between the sealed housing and the cover. The auto-injector may further include an interlock, such that the sealed housing cannot be displaced unless the mechanism has been removed or released by the user when use of the auto-injector is required.

To assist the user in performing a proper administration, the auto-injector should be correctly oriented at the time of injection. The auto-injector may assist orientation with labeling, tactile surfaces, material color or transparency, and other indicia indicating select sides. Furthermore, the auto-injector may present itself with rotational aids, whereas the aids can be contoured, textured, coated or combination of such to further indicate orientation and operation. In addition, the auto-injector can include a viewing window into the internals of the auto-injector for medicament inspection which may further assist the user in establishing orientation.

In one aspect the sealed housing is composed of two components; a top and bottom half that are mated together. Disposed inside the sealed housing is a medicament reservoir containing the medicament, a medicament dispensing system (MDS), and a needle extension system (NES). The embodiment of the bottom half may provide an aperture for the injection needle to pass through. The two halves, are of such geometry that they may locate and secure the internal components. The two halves which comprise the sealed housing may provide a mechanism or interface for rotating the housing relative to the cover. In some embodiments the sealed housing may aid in determining the fixation location for the MDS, and the NES, as well as aid in the releasing of both systems at time of injection. Additionally, the housing may provide a feature for determining the angular displacement or rotation of the needle barrel that the injection needle is affixed to. The sealed housing may aid in providing alignment during the displacement relative to the cover. Furthermore, the two halves may each provide features to assist in assembly of the two halves to ensure the correct internal alignment. The sealed housing can provide a means of bracing or supporting the injection needle. In addition, the two halves may contain or align the interlocks for preventing displacement of the sealed housing relative to the cover, once the injection has been performed.

The medicament dispensing system (MDS) which dispenses the medicament is composed of a plunger, a biasing member, a retainer, and a keeper. The biasing member may be similar to a mechanical compression spring. The spring may be held in a state preserving potential energy to be released at the time of injection. The retainer which displaces the plunger, may bound the spring on one end and may have a fixation point on the opposite end. The retainer may facilitate a self-fixation or be fixed in place with a separate locking mechanism which may be released or unlocked at the time of injection. The keeper may bound the side of the spring opposite of the retainer and control the displacement of the retainer relative to the keeper. The displacement of the retainer relative to the keeper is proportional to the volume of medicament dispensed. The MDS may further include a dispensing needle coupled to the retainer in constant fluidic communication to the injection needle. Once the retainer contacts the plunger, the dispensing needle pierces the plunger and is in communication with the contained medicament, and therefore, the medicament is in fluidic connection with the injection needle as well. Once released, the retainer further displaces the plunger to pump the dose out of the reservoir, through the dispensing needle, through the fluidic connection, and through the injection needle. A flexible or combination of a rigid and flexible tube may be used to interconnect the dispensing needle with the injection needle.

In certain embodiments the needle extension system (NES) can include a curved injection needle, a needle barrel for supporting the curved injection needle, a needle barrel guide for aligning the needle barrel and injection needle during administration, and a biasing member coupled to the needle barrel for rotating the needle barrel to straighten the curved injection needle to deploy the distal end of the tissue. The biasing member may be a torsion spring. In some embodiments, the axis of rotation of the needle barrel may be substantially perpendicular to a longitudinal axis of the medicament reservoir. The NES can include a needle barrel cap, or another means of fixating or securing a proximal end of the injection needle to the barrel. Additionally, the needle barrel cap may aid in securing the flexible tubing to the needle. The barrel cap and or barrel may provide a means of determining the starting and ending rotational position of the injection needle proportional to the depth of injection. In certain embodiments the needle barrel may be secured with a locking mechanism to maintain the potential energy of the torsion spring while held under load, to be released or removed at the time of injection. Furthermore, the needle barrel guide may maintain the concentricity of the needle barrel during the injection. The step of triggering the deployment of the curved injection needle through the aperture in the housing can include manually compressing the auto-injector when the housing is aligned with the cover for an injection and the rotation of the needle barrel to drive the distal end of the curved injection needle through the aperture. Advantageously, the step of retracting the distal end of the injection needle through the aperture, results from releasing the manual compression of the auto-injector. Following the injection, the displacement of the sealed housing relative to the cover may actuate an interlock, preventing further reuse of the auto-injector.

In certain embodiments the housing is protected by the cover which provides protection for the sealed housing during the storage of the auto-injector. The cover may also provide a means of bounding the sealed housing, such that the sealed housing is displaced with respect to the cover in a controlled manner. In various embodiments, a biasing member facilitates this displacement of the housing relative to the cover. The biasing member can be a spring that is integrally formed with the cover, or sealed housing, or conversely a separate component which can be disposed between the sealed housing and the cover. The cover may act or perform as the triggering mechanism for the injection. In addition to acting or performing as a protection and a triggering mechanism, the cover may also provide a stable base or platform to perform the injection. The injection contact surface of the cover may provide a tactile surface, which can facilitate the following functionalities: provide a stabilizing base for the auto-injector during injection, aid the user in establishing orientation, as well as affix the auto-injector to the injection location through the means of an adhesive layer or other attachment means. Furthermore, the bounding of the sealed housing by the cover may serve as a means of alignment during the injection. Once the sealed housing has been displaced relative to the cover to perform an injection, the cover will maintain alignment during the manual compression of the auto-injector from the armed to injection position to release the MDS and NES. The manual compression of the sealed housing while performing an injection, reduces the total height of the auto-injector and causes the sealed housing to contact with the intended triggers or protrusions on the cover. The contact with the triggers or protrusions between the cover and the sealed housing while performing an injection, due to the compression of the auto-injector by the user may release the energy stored in the biasing members to both deploy the injection needle and dispense the medicament. Upon compressing the sealed housing relative to the cover, the distal end of the injection needle will protrude past the cover, through an aperture, and dispense the desired dose. In some embodiments the cover may serve as a means of straightening the injection needle and provide a backing to support the injection needle during injection. In this manner, the length of the injection needle that is deployed into the tissue can be straight and perpendicular to the injection surface. Additionally, the cover can provide a means of guiding the sealed housing during the manual compression to aid in the alignment between the two components, to ensure proper release of the MDS and NES. Upon releasing the applied compression force, the biasing member displaces the sealed housing relative to the cover, increasing the height of the auto-injector and retracting the distal end of the injection needle to conceal the needle and protect the user from accidental needle sticks. Advantageously, the auto-injector can include an interlock to prevent a subsequent manual compression of the auto-injector, thereby rendering the auto-injector single-use. The interlock can be an abutting structure in the housing and the cover. The method mentioned above includes the steps of triggering deployment of the curved injection needle through an aperture in the housing, straightening of the injection needle, to embed the distal end of the injection needle in tissue at a desired depth, triggering piercing of the medicament reservoir with the dispensing needle to provide fluidic communication between the reservoir and the injection needle, dispensing the dose through the injection needle and, thereafter, retracting the distal end of the injection needle.

In certain embodiments the auto-injector will be presented with a safety mechanism to be removed firstly before any subsequent operations. The injection surface may be exposed to the user once the safety mechanism has been removed, further aiding in establishing an auto-injector orientation. The safety mechanism may also provide a means of preventing the sealed housing from displacing relative to the cover prior to removal, such that the injection sequence may not commence without first removing said mechanism. Alternatively, or additionally, the safety mechanism may protect the user from the injection needle if an accidental discharge were to happen or remove a protective shroud or sheath that would perform a similar functionality. Therefore, the removal of the safety mechanism may provide or facilitate the following functionalities: establish orientation of the auto-injector, provide an interlock to prevent the displacement of the sealed housing relative to the cover prior to removal, protecting the user from the injection needle, removing a conjoined or coupled component that would further protect the injection needle or user from said injection needle, as well as protecting a tactile coating or surface on the injection contact surface of the cover.

Prior to performing the injection, the injection needle in the NES and the dispensing needle in the MDS may be covered or sealed to maintain predetermined cleanliness criteria during storage of the auto-injector. Subsequently one embodiment of the auto-injector may provide the user with protection from the distal end of the injection needle by the means of a needle sheath. The needle sheath may fully encase the injection needle to prevent any contamination to the needle prior to use. In one embodiment the needle sheath is used in conjunction with another component to protect the distal portion of the injector needle, which will be embedded in the tissue, from contaminants. The needle sheath may also provide a means to prevent the needle from injuring the user if an accidental discharge were to occur. In other embodiments, the needle sheath may be fixed to the safety mechanism to aid in preventing an accidental injection. The needle sheath may provide a means of fixation to aid in removal prior to use. In one embodiment the needle sheath has a snap fit which allows the joining of the needle sheath to the safety mechanism to assist in removal prior to injection. Alternatively, the needle sheath may only serve to prevent the injection needle from being contaminated and the safety mechanism can provide the user with protection from an accidental discharge of the injection needle.

In some embodiments the auto-injector may have an internal power source to allow certain functionalities of the auto-injector during storage, during injection, and post injection. The auto-injector may provide audible instructions for performing an injection. Additionally, connectivity of the auto-injector to everyday smart devices allows for additional functionality. The connected smart device may display visual and/or auditory instructions for performing an injection. Certain embodiments may allow for the user to monitor the temperature, and location of the auto-injector. Additionally, the connected smart device may allow the user to see if other auto-injectors are nearby. Additional embodiments may allow the smart device to contact emergency responders or next of kin once an injection has been initiated. Furthermore, information about the auto-injector may be monitored remotely by the manufacturer.

In one aspect, the invention relates to a compact, high aspect ratio auto-injector for delivering a medicament dose subcutaneously or intramuscularly. The auto-injector can include a housing; a medicament dispensing system disposed within the housing and including a medicament reservoir adapted to contain the dose; and a needle extension mechanism coupled to the medicament reservoir, the needle extension mechanism including a curved injection needle adapted to be straightened during deployment of the needle to facilitate dispensing of the dose by the auto-injector.

In some embodiments of the above aspect, the housing includes a sealed housing rotatably retained in a cover. The housing can also include an interface to receive user input to facilitate a manual rotation of the housing relative to the cover from a first locked position to a second unlocked position. In some cases, the housing, the cover, a label, and/or a component directly visible to the user includes indicia indicating the locked position, the unlocked position, and an armed position. The auto-injector can also include a biasing member, such that when the housing is rotated to the unlocked position, the sealed housing is automatically displaced axially relative to the cover, increasing a height of the auto-injector. The biasing member can include a spring that integrally formed with the housing integrally formed with the cover, and disposed between the housing and the cover. In some instances, the auto-injector also includes an interlock, such that the housing cannot be rotated relative to the cover or displaced axially relative to the cover without removal of the interlock. In some cases, manual compression of the auto-injector in an armed position, reduces the height of the auto-injector, and activates a mechanism that straightens and extends a distal end of the injection needle through the housing, dispenses the dose through the injection needle, and activates an interlock. In such cases, upon release of manual compression, the biasing member can automatically displace the housing axially relatively to the cover, increasing a height of the auto-injector and retracting the distal end of the injection needle into the housing. The auto-injector can also include an interlock to prevent subsequent manual compression of the auto-injector, thereby rendering the auto-injector single-use. The interlock can include an abutting structure in the housing and the cover.

In some embodiments of the above aspect, the medicament dispensing system can further include a plunger within the medicament reservoir and forming a sealed cavity for retaining the dose. The medicament dispensing system can include a dispensing needle in fluidic communication with the injection needle. In some cases, the auto-injector can include a flexible tube interconnecting the dispensing needle with the injection needle. The medicament dispensing system can also include a spring, a retainer, and a locking mechanism such that when the locking mechanism is released, the spring displaces the retainer and forces the dispensing needle to pierce the plunger to provide fluidic communication with the dose. In some cases, the cover includes a second trigger to release the retainer and the locking mechanism. The spring (e.g., a compression spring) may further displace the plunger out of the vial and through the dispensing needle to the injection needle.

In some embodiments of the above aspect, the needle extension mechanism can also include a needle barrel for supporting the curved injection needle, a spring (e.g., a torsion spring) coupled to the barrel for rotating the barrel to uncoil the curved injection needle, and a barrel locking mechanism to prevent inadvertent rotation of the barrel. The cover can form an aperture through which a distal end of the injection needle passes during rotation of the barrel to straighten the injection needle. In some cases, release of the barrel locking mechanism permits the spring to rotate the barrel and deploy the injection needle. In some cases, the cover includes a first trigger to release the needle barrel locking mechanism. The needle extension mechanism may also include a barrel cap to secure a proximal end of the injection needle to the needle barrel.

In another aspect, the invention relates to a method of operating a compact, high aspect ratio auto-injector auto-injector for delivering a medicament dose subcutaneously or intramuscularly. The auto-injector can include a housing, a medicament dispensing system including a medicament reservoir adapted to contain the dose, and a needle extension mechanism coupled to the medicament reservoir, the needle extension mechanism including a curved injection needle. The method can include the steps of triggering deployment of a distal end of a curved injection needle through an aperture in a cover of the housing to straighten the injection needle; triggering piercing of the medicament reservoir to provide fluidic communication between the reservoir and the curved injection needle; dispensing the dose through the injection needle at a desired injection location; and thereafter, retracting the distal end of the injection needle into the auto-injector.

In some embodiments of the above aspect, the auto-injector further includes an interlock, such that the housing cannot be rotated relative to the cover or displaced axially relative to the cover without removal of the interlock. In some cases the housing can include a sealed housing rotatably retained in the cover and the method further includes manually rotating the housing relative to the cover from a first locked position to a second unlocked position, in which the sealed housing is automatically displaced axially relative to the cover to an armed position, increasing a height of the auto-injector. In some instances, the method further includes the step of determining the locked position, the unlocked position, and the armed position based on indicia on at least one of the housing, the cover, a label, and a component directly visible to the user. The method can further include adhering the cover to the desired injection location prior to triggering of the auto-injector. In some instances, the step of triggering piercing of the medicament reservoir includes manually compressing the auto-injector when the auto-injector is in the armed position, which includes activating the medicament dispensing mechanism triggering piercing of a plunger within the medicament reservoir with a distal end of a dispensing needle. The step of triggering piercing of the medicament reservoir can further include pumping the dose out of the reservoir to the injection needle.

In some embodiments of the above aspect, the step of manually compressing the auto-injector when the auto-injector is in the armed position further includes activating the needle extension mechanism triggering the deployment of the curved injection needle through the aperture in the cover. In some cases, the step of activating the needle extension mechanism including deploying the curved injection needle through the aperture in the cover further includes rotating a needle barrel to drive the distal end of the curved injection needle through the aperture. In some cases, the step of activating the needle extension mechanism includes deploying a distal end of the curved injection needle through the aperture in the cover to straighten the injection needle. The step of retracting the distal end of the injection needle into the auto-injector can result from releasing manual compression of the auto-injector. The method can also include the step of removing the auto-injector from the desired injection location after dispensing the dose. The method can also include the step of automatically interlocking the auto-injector after retraction of the needle to prevent reuse of the auto-injector and exposure of a distal end of the injection needle. The method can also include the step of disposing of the auto-injector after a single use.

BRIEF DESCRIPTION OF THE DRAWINGS

In the drawings, reference characters generally refer to the same parts throughout the different views. Also, the drawings are not necessarily to scale, emphasis is instead generally being placed upon illustrating the principles of the invention. In the following description, various embodiments of the present invention are described with reference to the following drawings, in which:

FIG. 141 is a chart listing exemplary value ranges for certain parameters of the auto-injector, according to various embodiments.

DETAILED DESCRIPTION

A first embodiment of an auto-injector 1 is described below. Example user interactions and inputs with the auto-injector 1 are described first, followed by example internal mechanisms and interactions of the auto-injector's 1 components.

Figure 29:
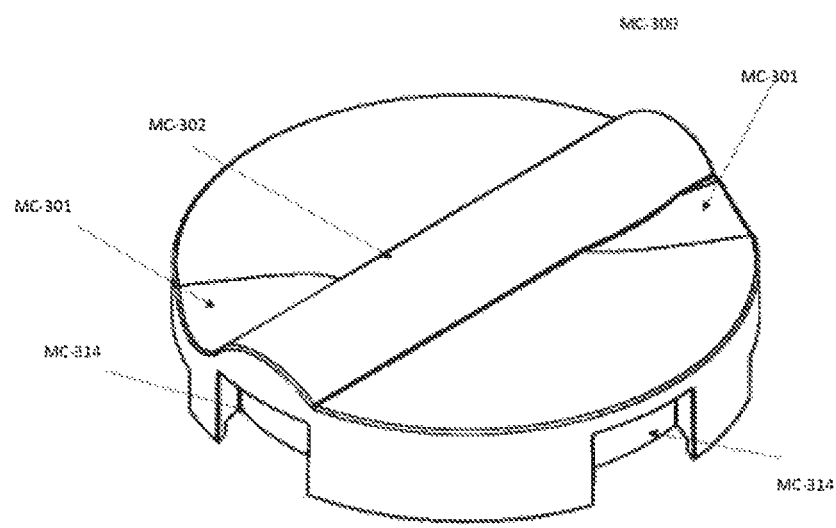
Figure 30:
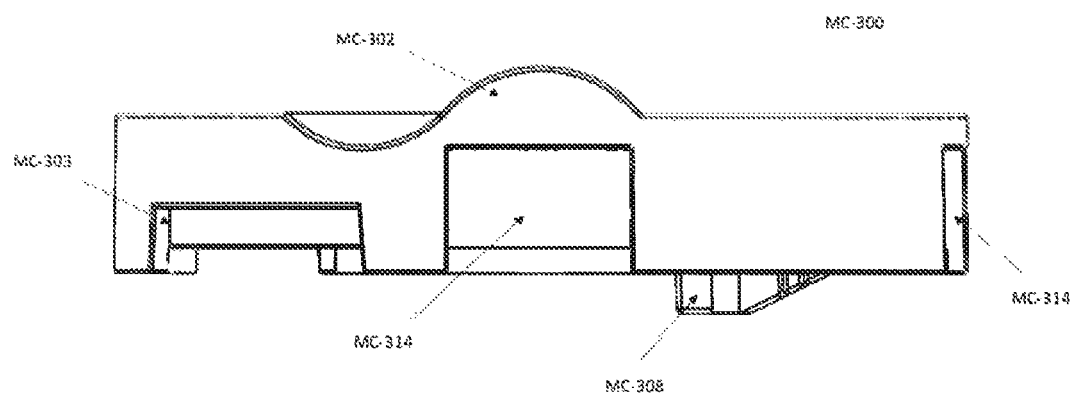

To assist the user in performing a proper administration, the auto-injector 1 should be correctly oriented at the time of injection. The auto-injector 1 may assist orientation with labeling, tactile surfaces, material color or transparency, and/or other indicia indicating select sides. Furthermore, the auto-injector 1 may present itself with rotational aids MC-301 (see, e.g., FIG. 29), which can be contoured, textured, coated (or combinations thereof) such to further indicate orientation and operation. In addition, the auto-injector 1 can include a viewing window into the internals of the auto-injector 1 for medicament inspection which may further assist the user in establishing proper orientation.

Figure 17:
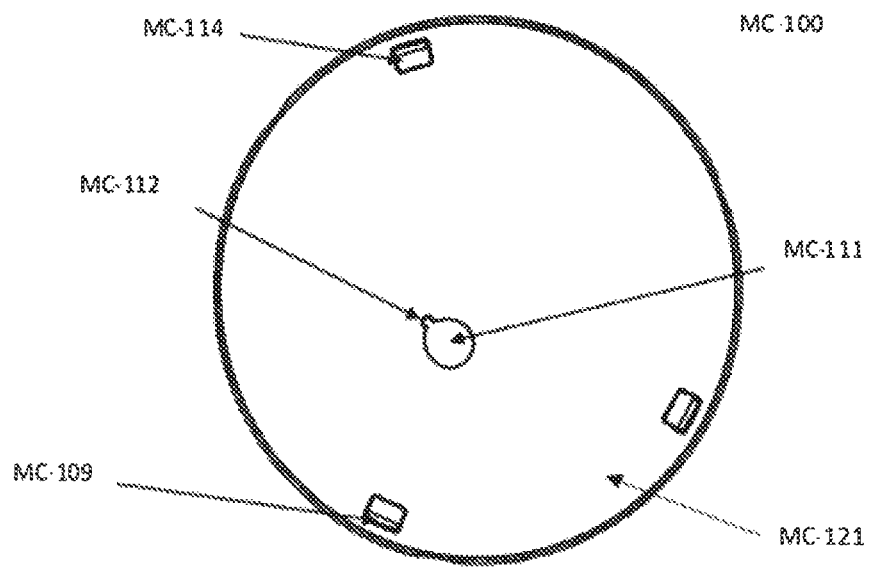
Figure 38:
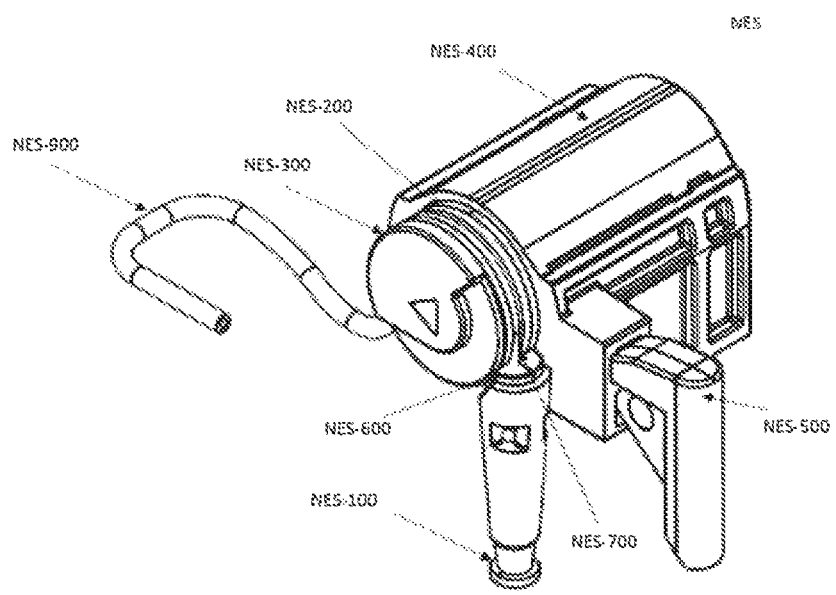
Figure 39:
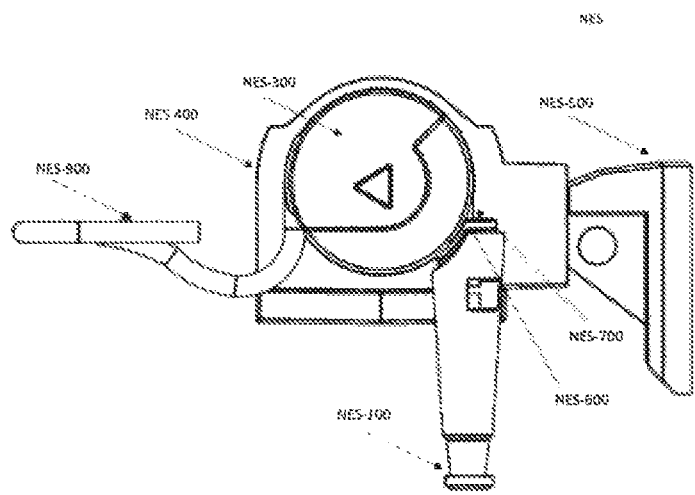
Figure 40:
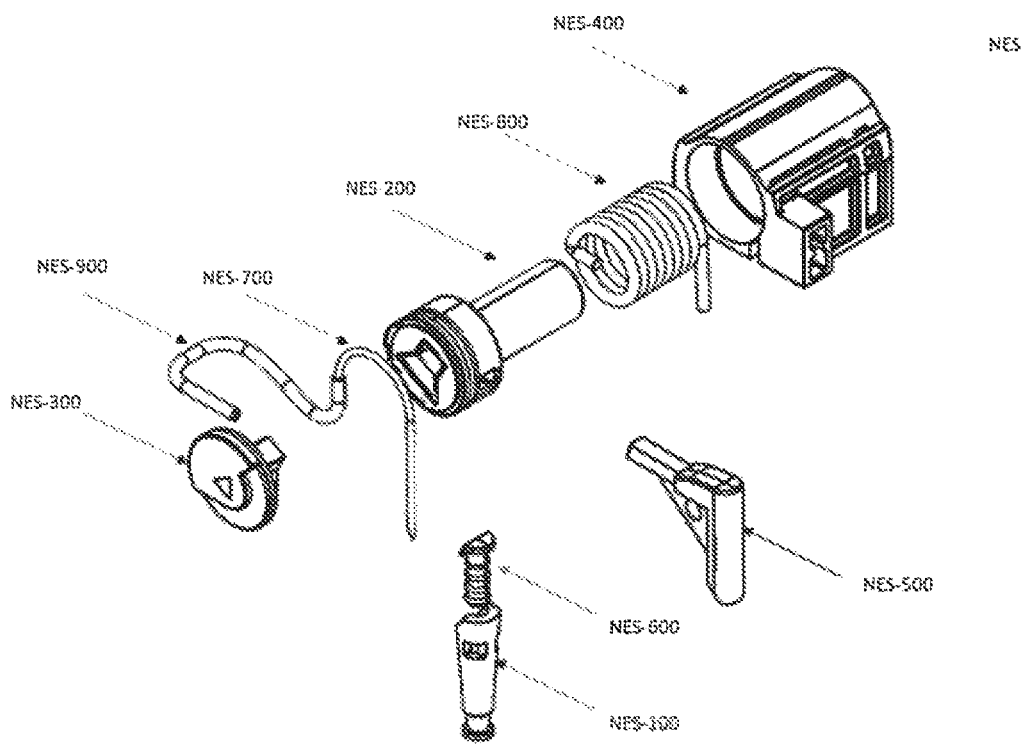
Figure 41:
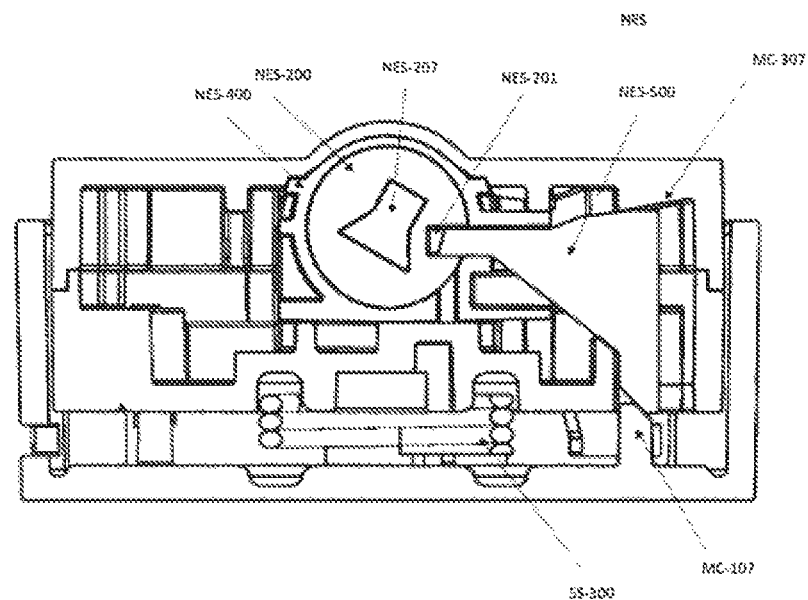
Figure 42:
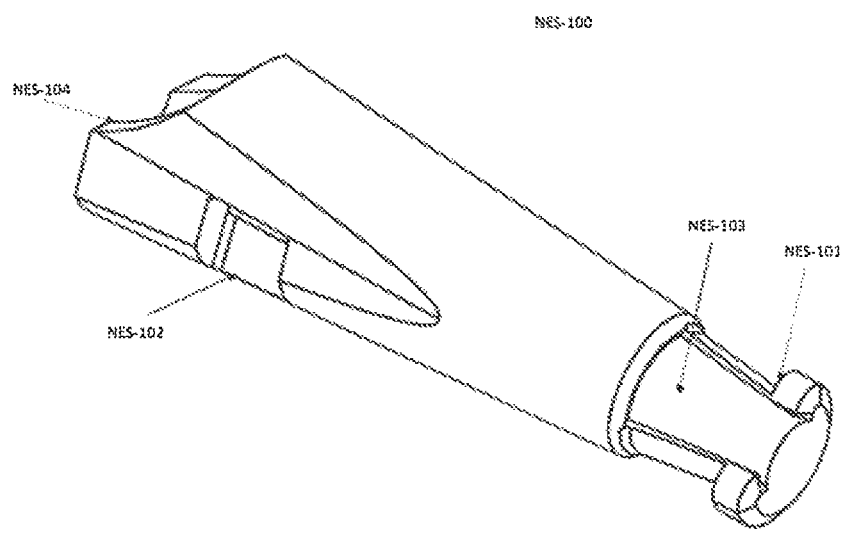
Figure 43:
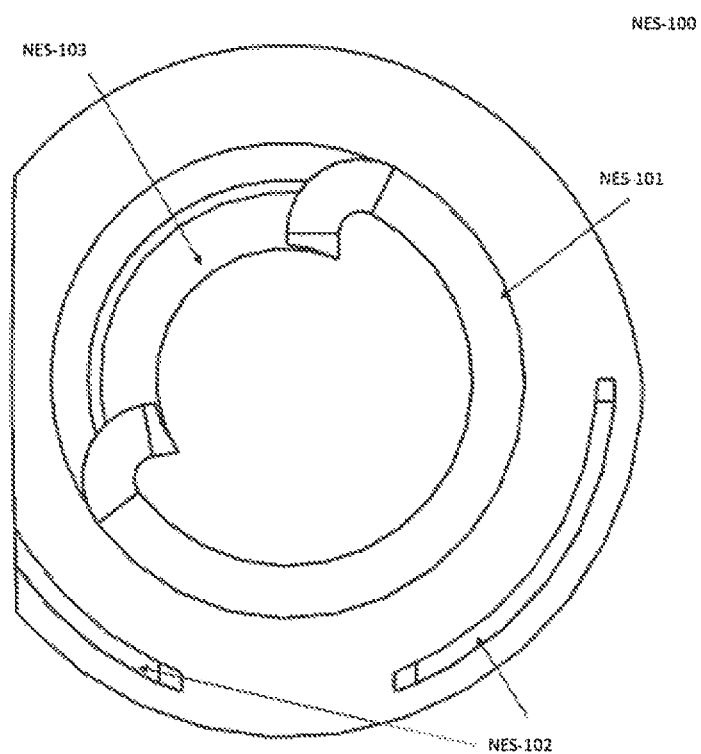
Figure 44:
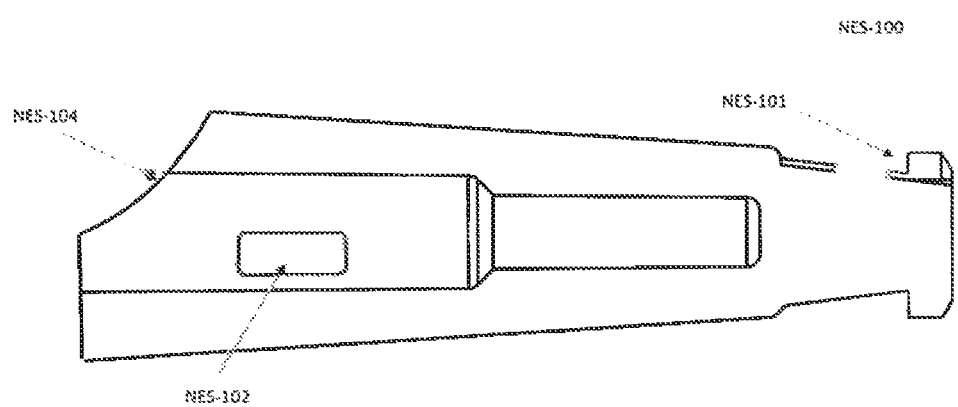
Figure 45:
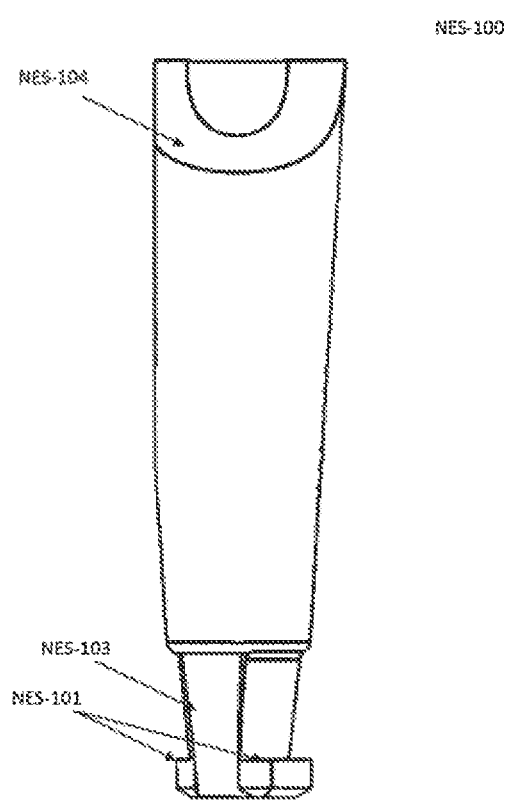
Figure 46:
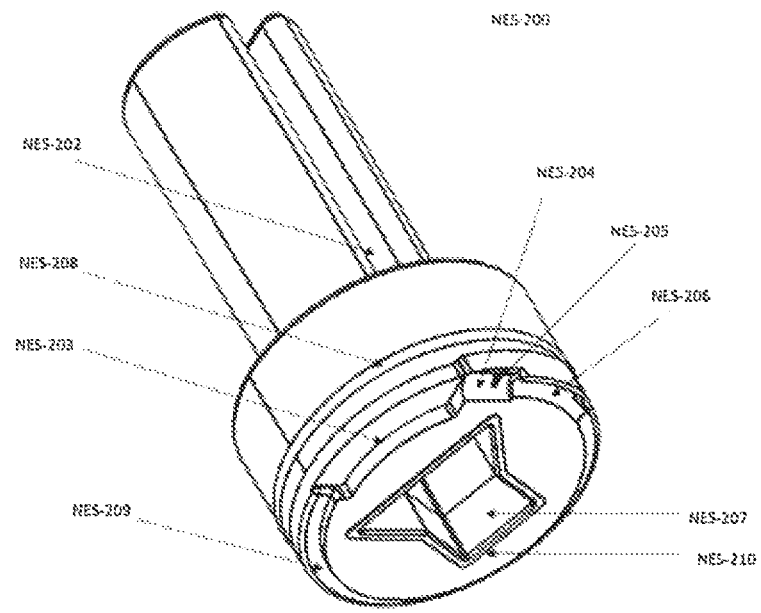
Figure 65:
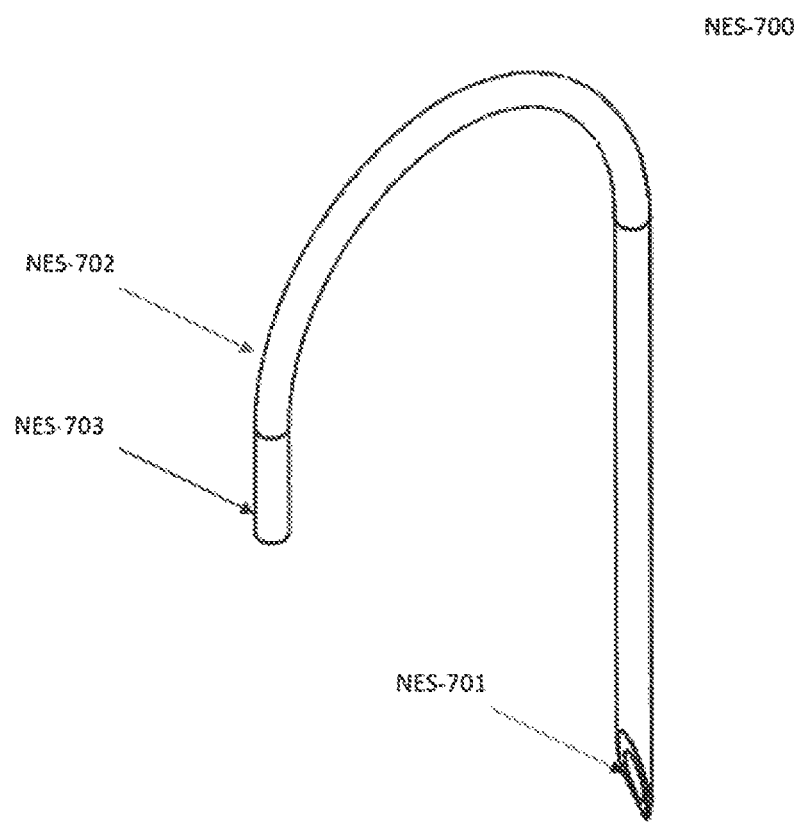
Figure 101:
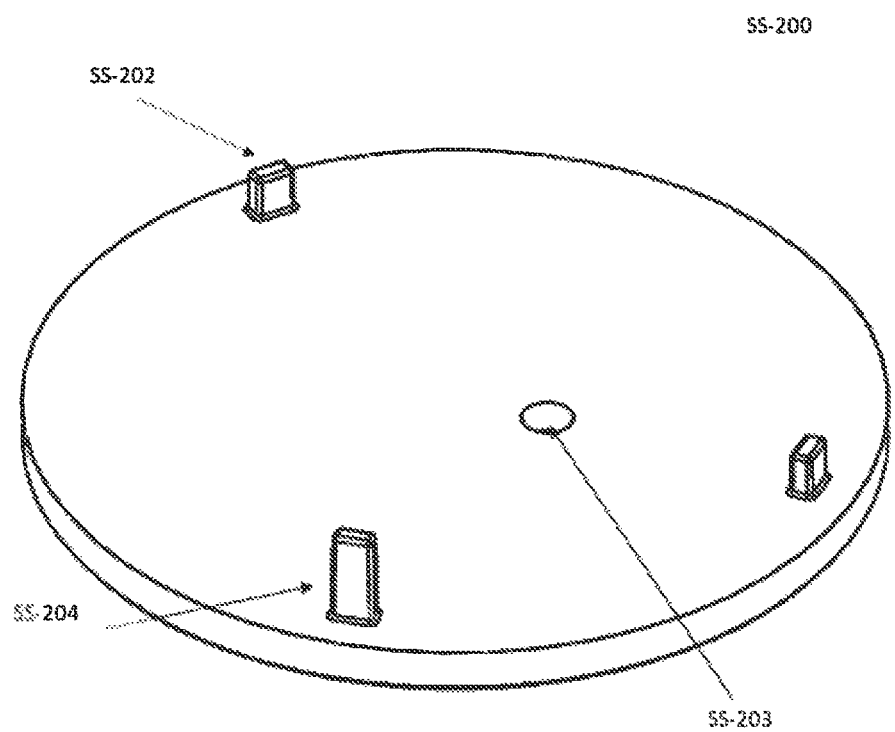
Figure 102:
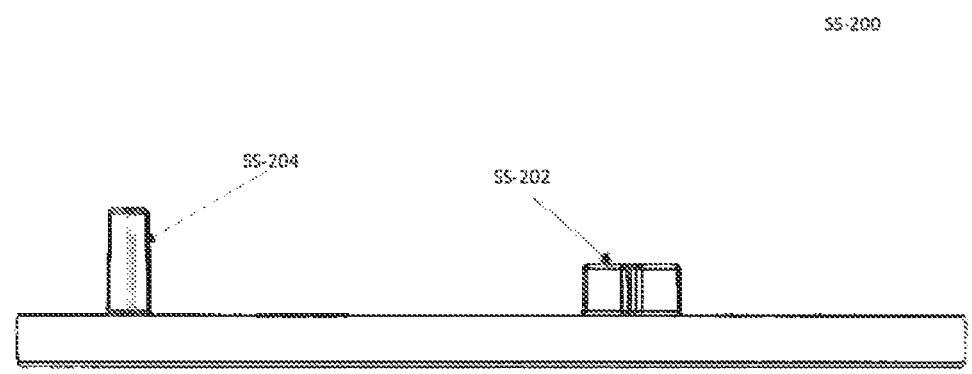

In certain embodiments, the auto-injector 1 includes a safety mechanism SS-200 (see, e.g., FIGS. 3-7) to be initially removed before any subsequent operations. An injection surface MC-121 (see, e.g., FIG. 17) may be exposed to the user once the safety mechanism SS-200 has been removed, further aiding in establishing a proper orientation. The safety mechanism SS-200 may also provide a means of preventing the sealed housing MC-200, MC-300 (see, e.g., FIGS. 3-6) from displacing relative to the cover MC-100 (see, e.g., FIGS. 3-6) prior to removal, such that the injection sequence may not commence without first removing said mechanism SS-200. Alternatively, or additionally, the safety mechanism SS-200 may protect the user from an injection needle NES-700 (see, e.g., FIG. 65) if an accidental discharge were to happen or remove a protective shroud or sheath NES-100 (see, e.g., FIG. 38-40) that performs a similar functionality. Therefore, the removal of the safety mechanism SS-200 may provide or facilitate the following functionalities: establish orientation of the auto-injector 1, provide an interlock SS-204 (see, e.g., FIGS. 101-102) to prevent the displacement of the sealed housing MC-200, MC-300 relative to the cover MC-100 prior to removal, protecting the user from the injection needle NES-700, removing a conjoined or coupled component NES-100 that would further protect the injection needle NES-700 or user from said injection needle NES-700, as well as protecting a tactile coating or surface on the injection contact surface MC-121 (see, e.g., FIG. 17) of the cover MC-100.

Figure 1:
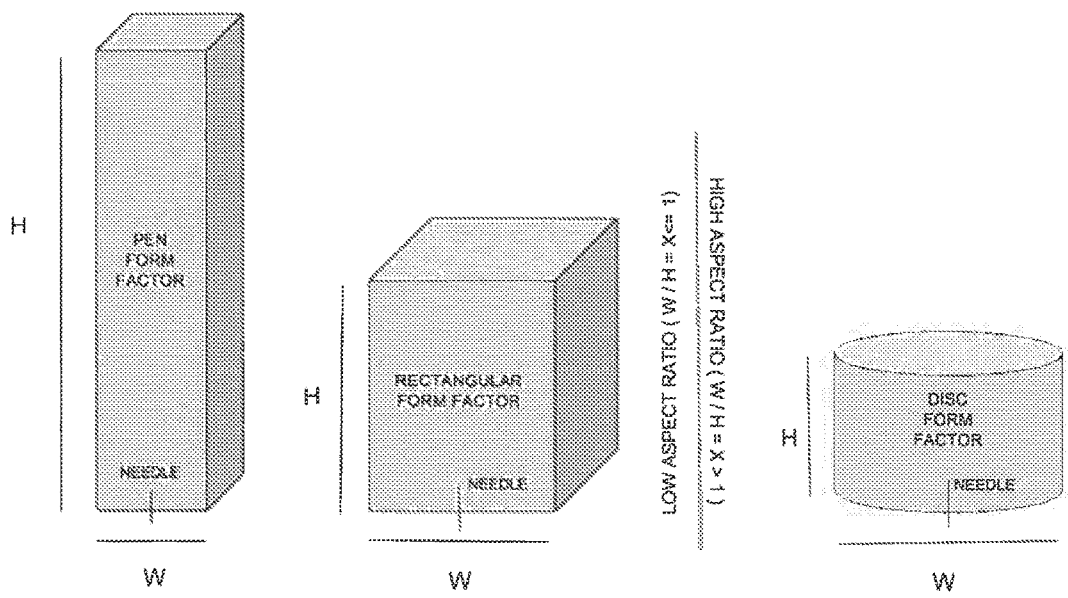
FIG. 1 is a comparison of existing auto-injector form factor aspect ratios versus an example high aspect ratio auto-injector, according to various embodiments.
Figure 2:
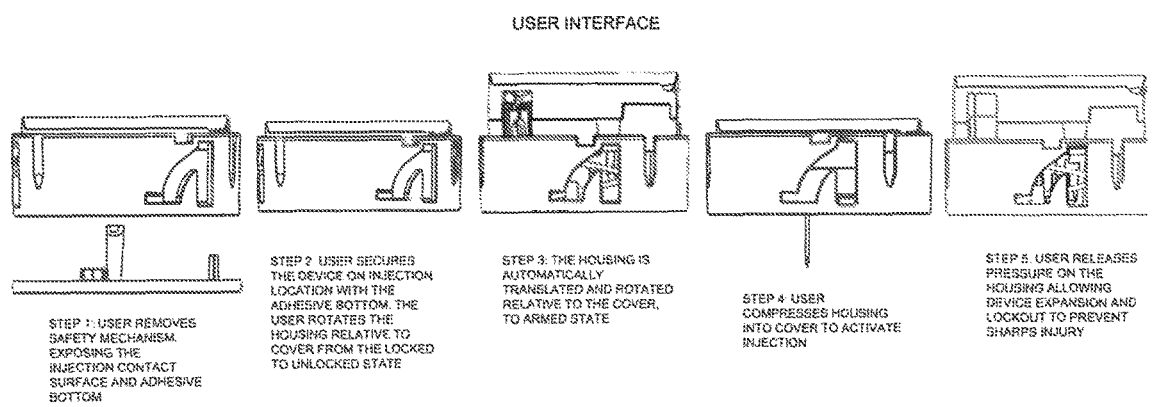
FIG. 2 is a depiction of the injection sequence indicating a user's inputted actions with the auto-injector and the subsequent auto-injector outputs, according to various embodiments.
Figure 3:
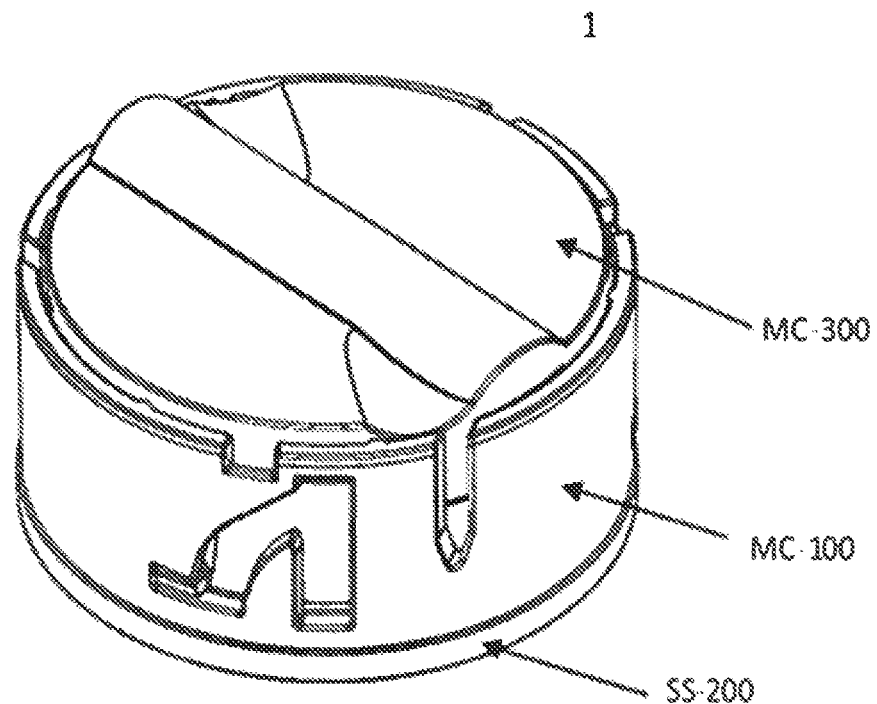
FIG. 3 is a schematic isometric view of an auto-injector in the stored or locked position, according to various embodiments.
Figure 4:
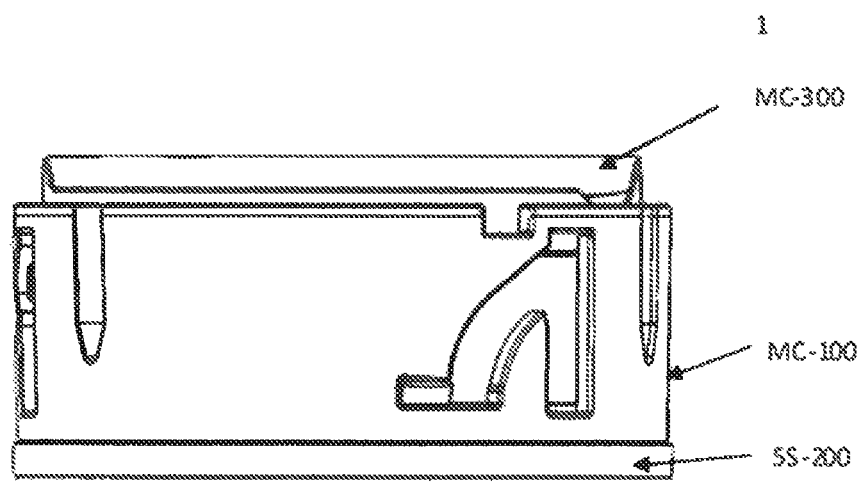
FIG. 4 is a schematic side view of the auto-injector in the stored or locked position, according to various embodiments.
Figure 5:
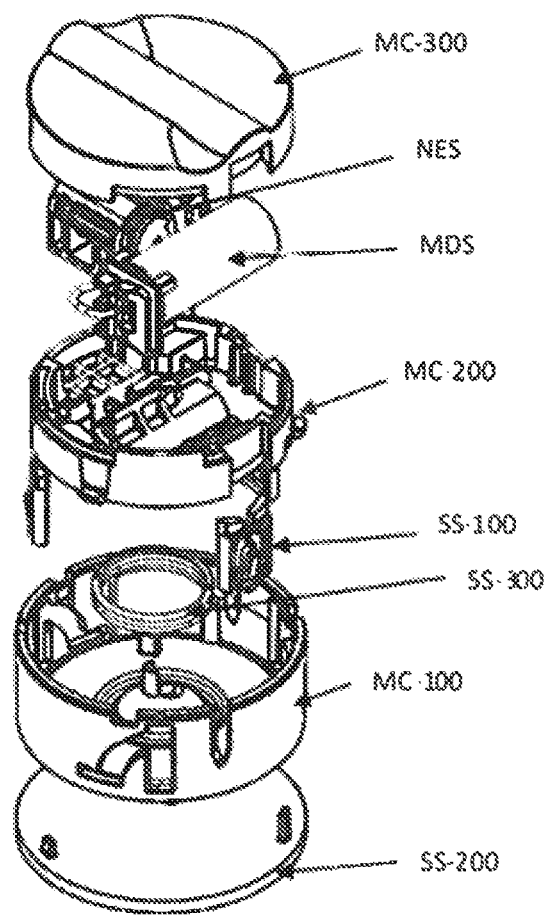
FIG. 5 is a schematic isometric exploded view of internals of the auto-injector, according to various embodiments.
Figure 6:
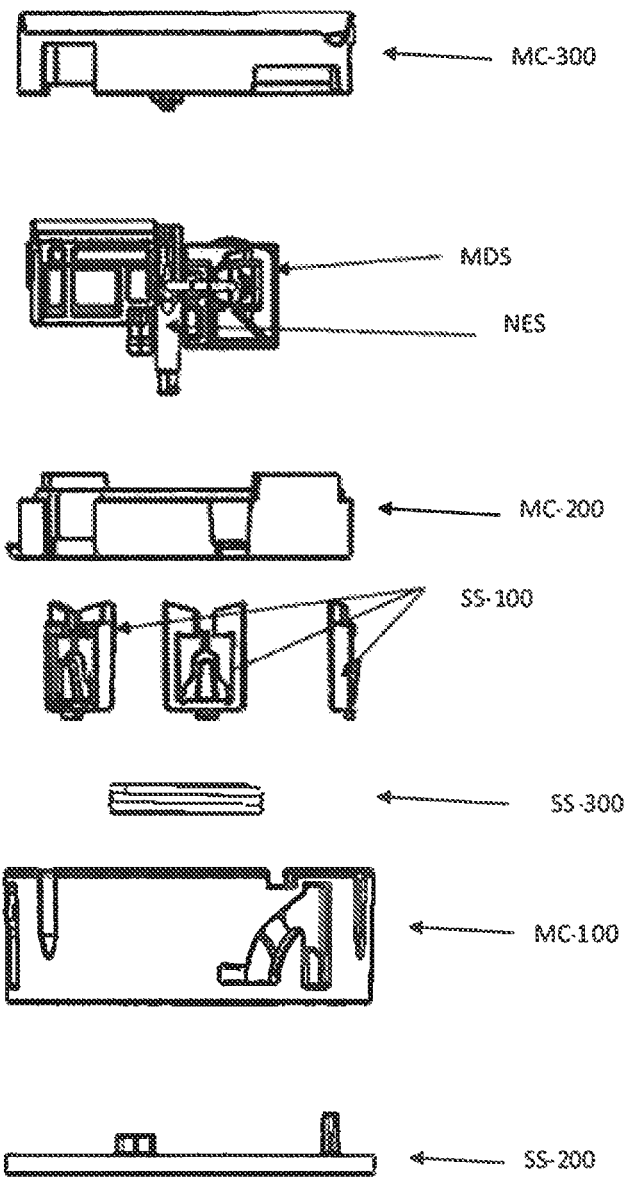
FIG. 6 is a schematic side exploded view of internals of the auto-injector, according to various embodiments.
Figure 7:
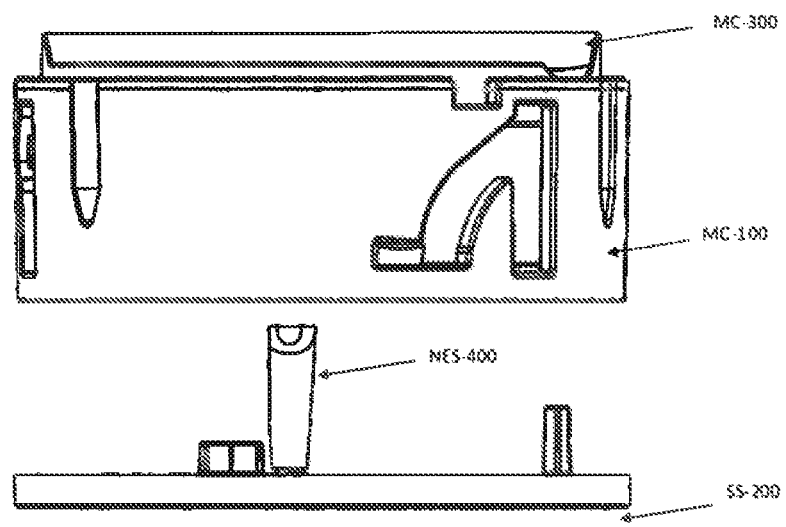
FIGS. 7-11 are schematic side view of the sequential steps in performing an injection, according to various embodiments (e.g., depicted in FIG. 2)
Figure 8:
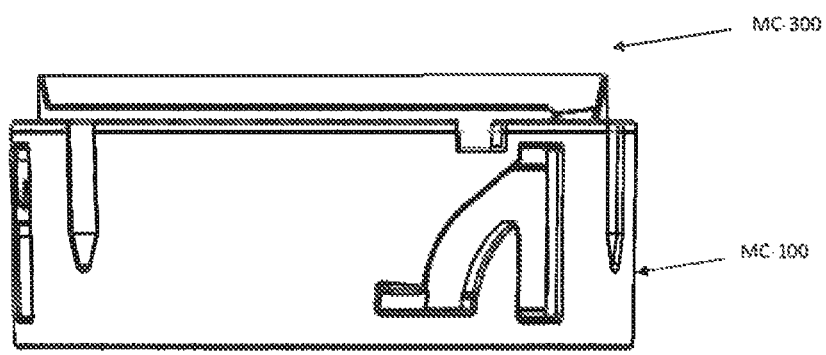
Figure 9:
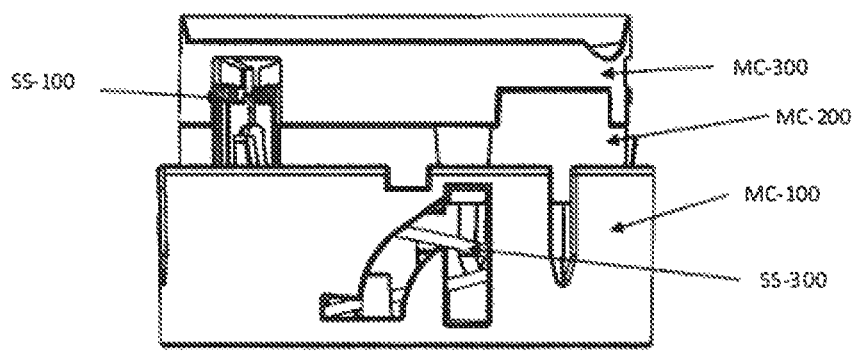
Figure 10:
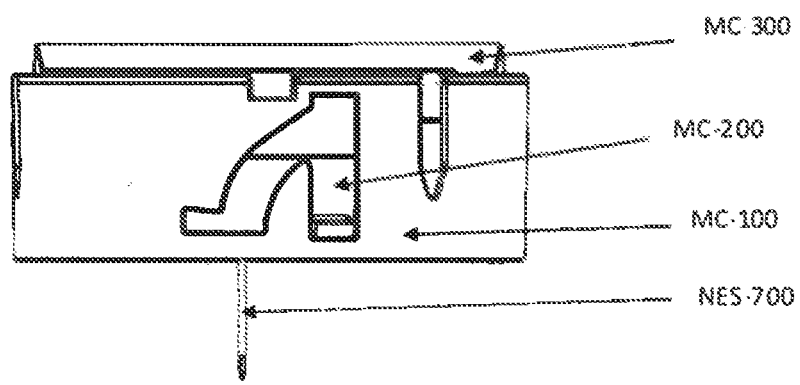
Figure 11:
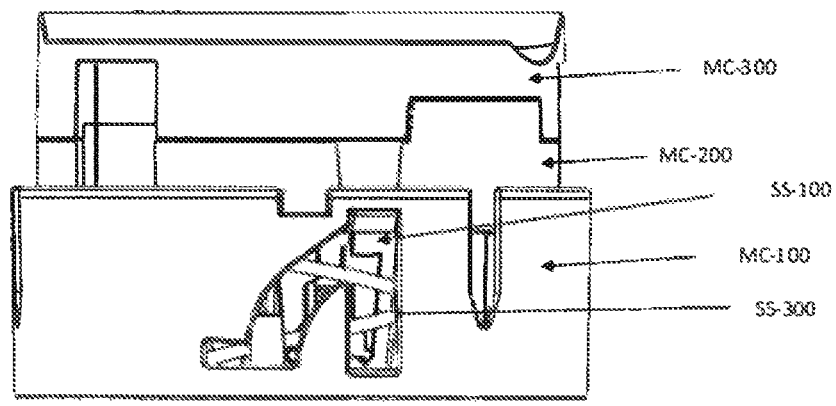
Figure 12:
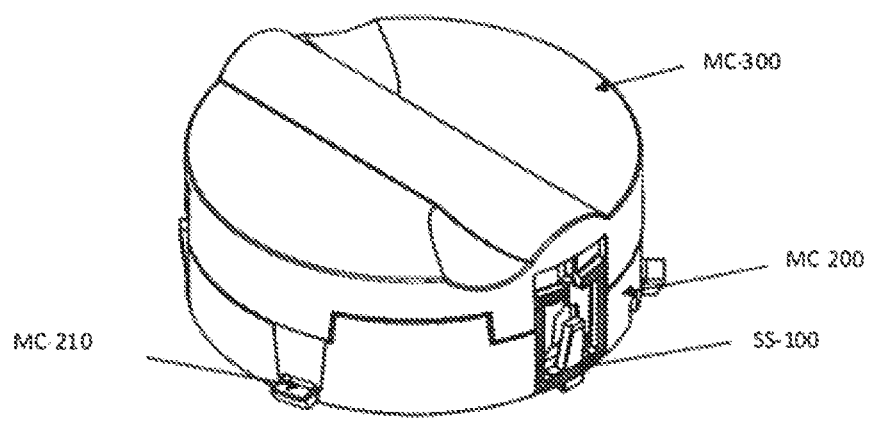
FIGS. 12-140 are schematic views of various system assemblies and components of auto-injectors, according to various embodiments.
Figure 13:
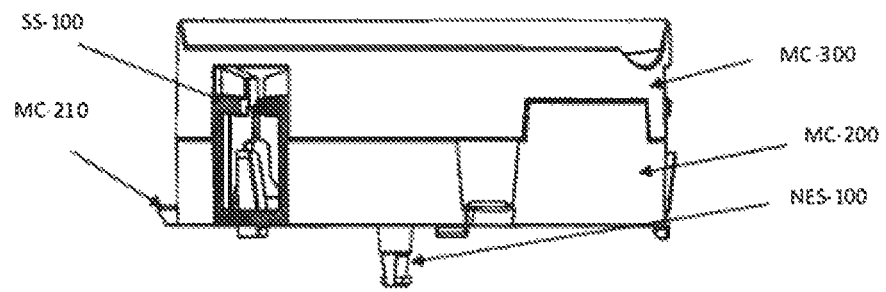
Figure 14:
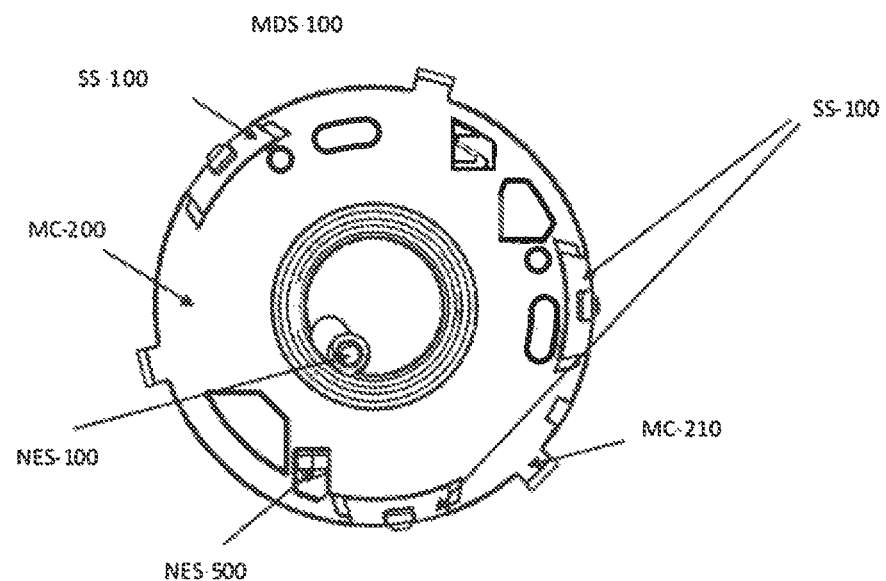

In various embodiments, in addition to the internal components discussed below, the auto-injector 1 includes two main parts, a sealed housing MC-200, MC-300 rotatably retained in a cup-shaped cover MC-100 that also forms the bottom side or injection contact surface MC-121. The sealed housing MC-200, MC-300 is made from upper MC-300 and lower MC-200 halves bonded together through the means of ultrasonic welding or alternative means that provide sufficient adhesion and strength. In some embodiments the bond between the upper MC-300 and lower MC-200 halves may be such that it is a hermetic seal. Furthermore, the housing MC-200, MC-300 or one of the subsequent halves that compose the housing MC-200, MC-300 may contain tabs MC-210 (see, e.g., FIG. 12), that are molded or formed protrusions that guide and constrain the housing MC-200, MC-300 during operation within the cover MC-100. The sealed housing MC-200, MC-300 functions as the primary interface for the user performing the subsequent injection. The two halves that form the sealed housing, are of such geometry (e.g.: MC-201, MC-202, MC-204, MC-205, MC-206, MC-207, MC-208, MC-211, MC-213, MC-214, MC-216, MC-217, MC-218, MC-304, MC-305, MC-309, MC-310, MC-311, MC-312, MC-313, MC-314, MC-316) that they may locate and secure the internal components.

The cover MC-100, provides a protective shroud around the housing MC-200, MC-300 and supports the housing for rotation. In some embodiments, the first step in performing or initiating an injection is to remove the safety mechanism SS-200. The next step can be to place the injection contact surface MC-121 of the cover MC-100 on location. As mentioned previously, the safety mechanism SS-200 may aid the user in establishing an overall orientation of the auto-injector 1; therefore, once the injection contact surface MC-121 of the cover MC-100 is exposed from its removal it may further establish this orientation. The injection contact surface MC-121 of the cover MC-100 may provide a tactile surface which can facilitate the following functionalities: provide a stabilizing base for the auto-injector 1 during injection, aid the user in establishing orientation, and/or affix the auto-injector 1 to the injection location through the means of an adhesive or other attachment means.

Figure 15:
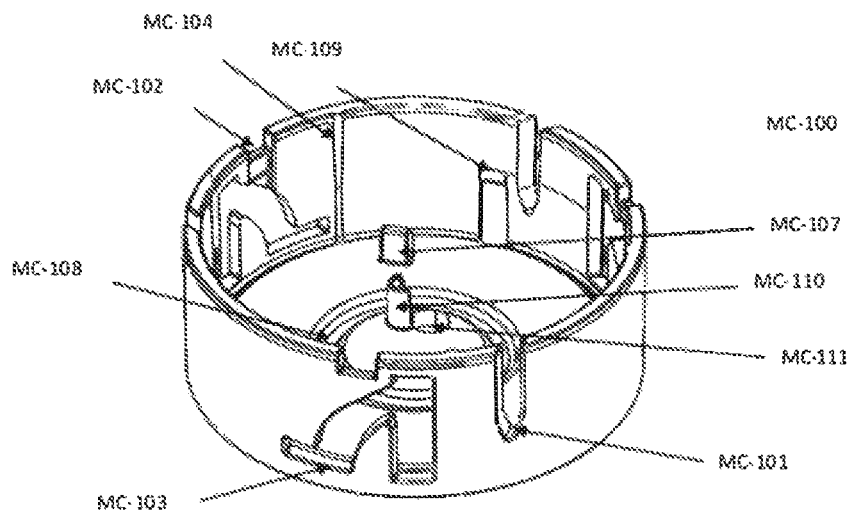
Figure 18:
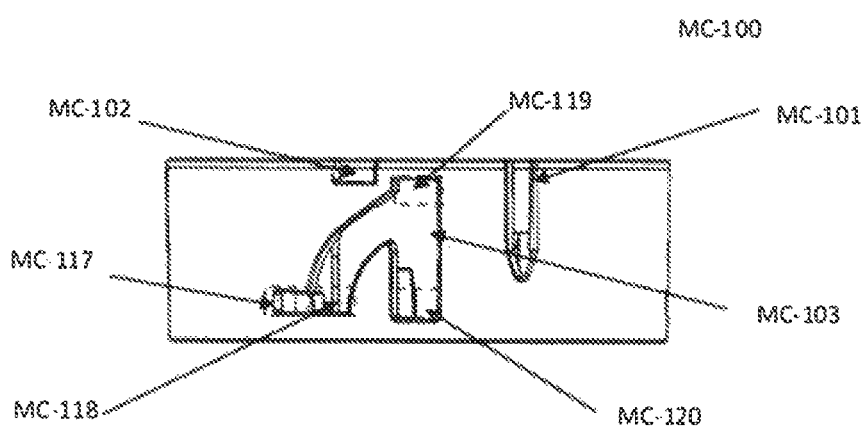
Figure 19:
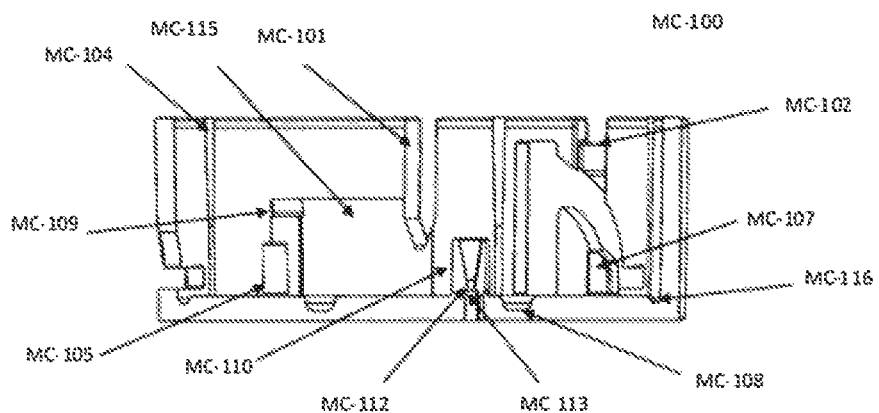
Figure 20:
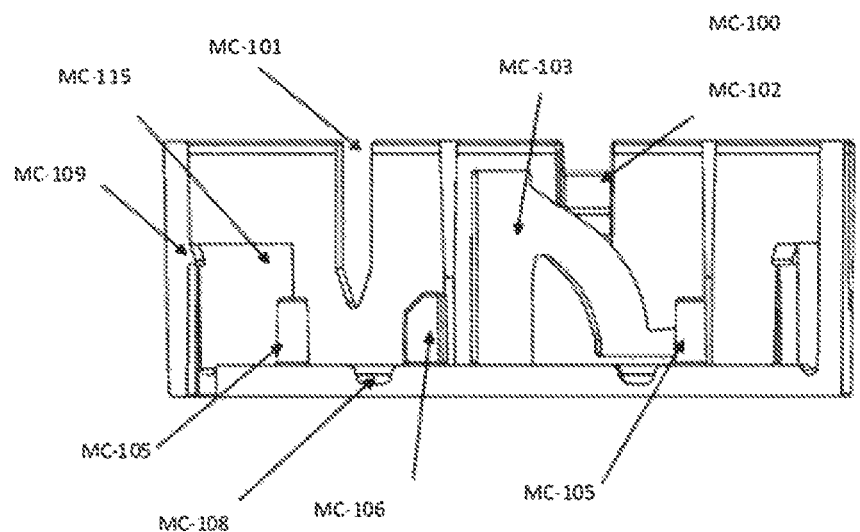
Figure 21:
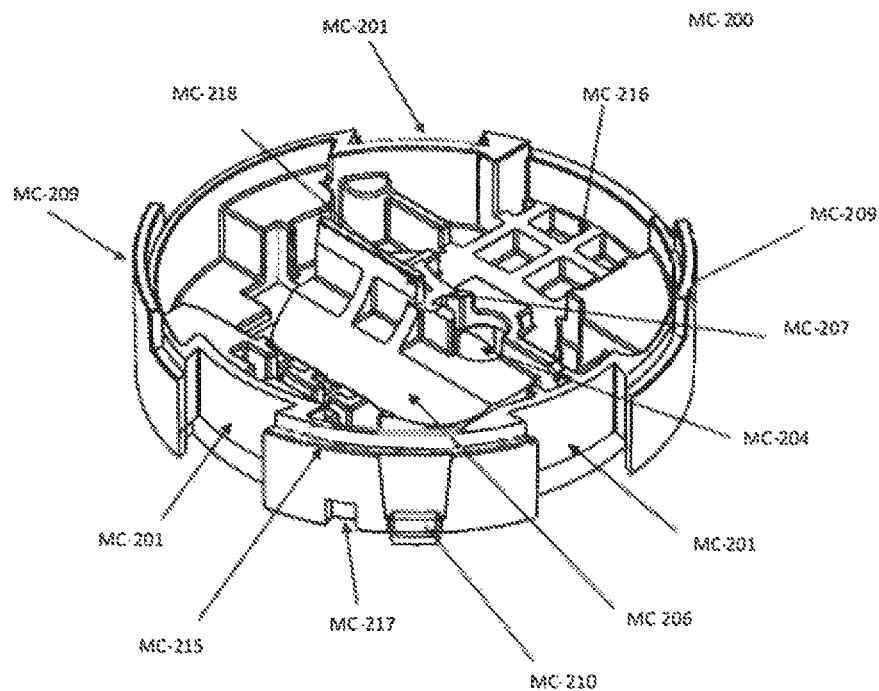
Figure 22:
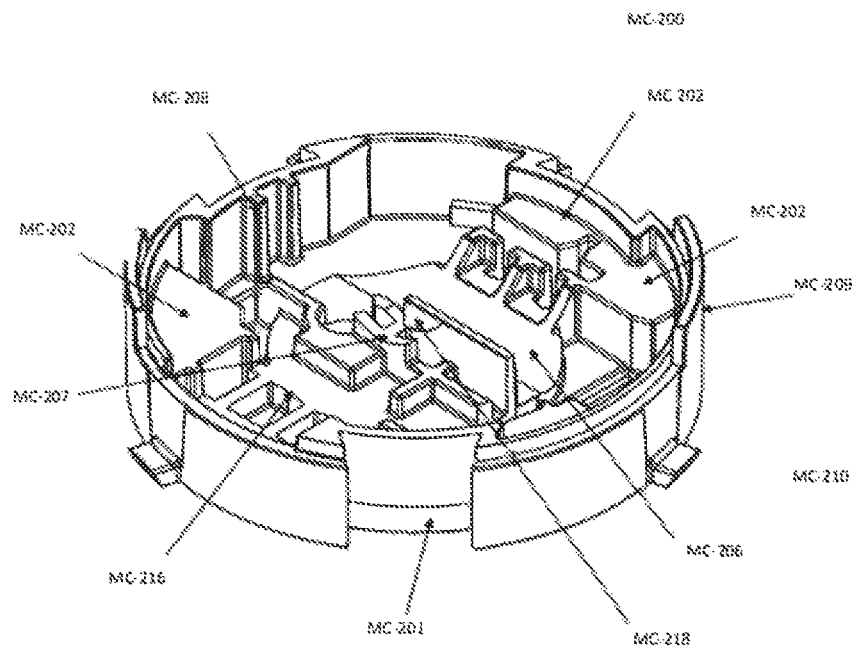

In various embodiments, the cover MC-100 has a spring SS-300 (see, e.g., FIGS. 5-6) disposed or formed therein, to bias the housing MC-200, MC-300 away from the cover MC-100 during activation, to facilitate use. A sidewall of the cover MC-100 may include channels, slots, detents, etc. MC-103 (see, e.g., FIG. 15) that correspond to different positions MC-117, MC-118, MC-119, MC-120 (see FIG. 18) or positions (e.g., locked, unlocked, armed, and injection) that cooperate with tabs or protrusions MC-210 (see FIGS. 21-22) on a sidewall of the housing MC-200, MC-300 or such components that form the housing MC-200, MC-300, to maintain alignment and control relative movement between various positions (e.g., locked, unlocked, armed, and injection). The channels, slots, detents, etc. MC-103 formed in the cover MC-100 guide the housing MC-200, MC-300 during the twisting, expanding, compressing, and subsequent expanding of the auto-injector 1 to facilitate the different phases of the injection method and use. In addition, the cover MC-100 facilitates the means of activating an interlock SS-100 (see, e.g., FIGS. 11-14) such that once the cover MC100 is in an injection position MC-120 and injection has commenced, subsequent expansion of the housing MC-200, MC-300 relative to the cover MC-100 has occurred, the auto-injector 1 may not be compressed a second time rendering the auto-injector 1 single use. The triggering mechanism MC-109 (see, e.g., FIGS. 19-20) is designed such that the interlock SS-100 will always be activated before the MDS or the NES to ensure that the sharps injury prevention feature functions, if the injection needle NES-700 is ever deployed. The cover MC-100 may also contain geometry MC-101, MC-102 or indicia, formed, molded or stamped to provide an orientation of the housing MC-200, MC-300 for either assembly of the auto-injector 1 or for operational administration.

In various embodiments, when the auto-injector 1 is in a stored position MC-117 and prior to use, the auto-injector 1 is in a locked position, in which the spring SS-300 is compressed and the auto-injector 1 is constrained. To move from the locked position MC-117 to the unlocked position MC-118, the user manually rotates the housing MC-200, MC-300 by applying an activation force to the grip surfaces MC-301 (e.g., one or more depressions, protrusions, textures, coatings, or combinations, etc.) formed on the upper surface MC-300 of the housing MC-200, MC-300. The user applied force displaces the sealed housing MC-200, MC-300 relative to the cover MC-100 from the locked position MC-117 to the unlocked position MC-118. Indicia, such as alignment marks on the sidewalls of the housing MC-200, MC-300 and the cover MC-100 may indicate the different positions (MC-117, MC-118, MC-119, MC-120) of the auto-injector 1. The alignment indicia may also be indicated using labels or other auto-injector 1 components (e.g., interlock SS-100) that are observable from the exterior surfaces. Once the housing MC-200, MC-300 is rotated from the locked position MC-117 to the unlocked position MC-118, the housing MC-200, MC-300 is biased away from the cover MC-100, and the auto-injector 1 expands to the armed position MC-119. The expansion from the unlocked position MC-118 to the armed position MC-119 is performed automatically by means of the stored potential energy in the biasing member SS-300, such that the user only needs to apply an activating force to the grip surfaces MC-301 to move the auto-injector 1 from the locked position MC-117 to the unlocked position MC-118. The automatic translation and rotation of the sealed housing MC-200, MC-300 relative to the cover MC-100 may be constrained and guided by the tabs or protrusions MC-210 on the sealed housing MC-200, MC-300 and channels, slots, detents, etc. MC-103 on the cover MC-100.

In various embodiments, once the housing MC-200, MC-300 is in the armed position MC-119, the tabs or protrusions MC-210 on the housing MC-200, MC-300, and the guides on the cover wall MC-103 prevent the housing MC-200, MC-300 from being rotated back to the unlocked position MC-118 and the locked position MC-117. In the armed position MC-119, the auto-injector 1 can only be vertically displaced towards the injection position MC-120. The orientation of the auto-injector 1 is such that the top side MC-300 is facing upwards (i.e., away from the injection location), with the flat bottom surface MC-121 of the cover MC-100 against the injection site. To inject the medicament, the user applies a normal force, perpendicular to the top side MC-300 pushing the sealed housing MC-200, MC-300 into the cover MC-100 to commence the activation sequence of the auto-injector 1 and injection of the medicament. The interlock mechanism SS-100 is activated just before the auto-injector 1 reaches the injection position MC-120, such that, once the user releases pressure, the interlock SS-100 is engaged, and a second injection cannot be attempted. To ensure complete dosing, the user maintains force on the sealed housing MC-200, MC-300 to maintain the injection position MC-120 for an allotted duration, and then releases pressure on the top side MC-300 of the auto-injector 1. The release of pressure on the sealed housing MC-200, MC-300 may permit the sealed housing MC-200, MC-300 to translate relative to the cover MC-100, by means of the biasing member SS-300, thereby retracting the needle NES-700. In various embodiments, since the interlocks SS-100 were previously activated MC-109, they will engage themselves while the sealed housing MC-200, MC-300 is translating relative to the cover MC-100. After the injection has been performed and the interlock SS-100 has engaged the triggering mechanism MC-109, a force of, at minimum, twice the injection force on the sealed housing MC-200, MC-300 will not permit exposure of the needle NES-700 from the injection contact surface MC-121 of the cover MC-100 and is able to be safely disposed of.

The following list of items (1-11) describes an example activation sequence of internal components and mechanisms of the auto-injector 1 and the individual component interactions, according to various embodiments.

1.) Before initiating an injection, the user can remove a safety mechanism SS-200 before any subsequent operations. The safety mechanism SS-200 protects the injection surface MC-121 such that upon removal, the injection surface MC-121 is exposed to the user, which may further aid in establishing proper orientation. The safety mechanism SS-200 can also provide a means (e.g., interlock SS-204) of preventing the sealed housing MC-200, MC-300 from displacing relative to the cover MC-100 prior to removal, such that the injection sequence may not commence without first removing said mechanism SS-200. The safety mechanism SS-200 may also remove a needle sheath NES-100 that protects the user from the injection needle NES-700 in the event of an accidental discharge. Additionally, the sheath NES-100 in combination with a barrier NES-600 (see, e.g., FIGS. 38-40) can cover the injection needle NES-700 and may prevent any possible contamination during storage of the injection needle NES-700. Therefore, at the time of injection, prior to the removal of the needle sheath NES-100, the injection needle NES-700 is sterile.

Figure 16:
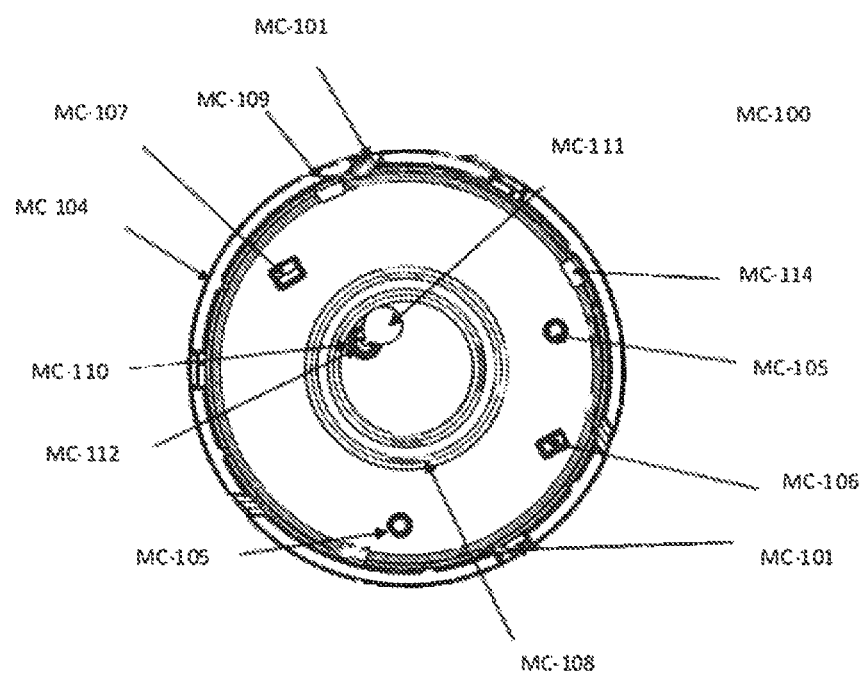
Figure 23:
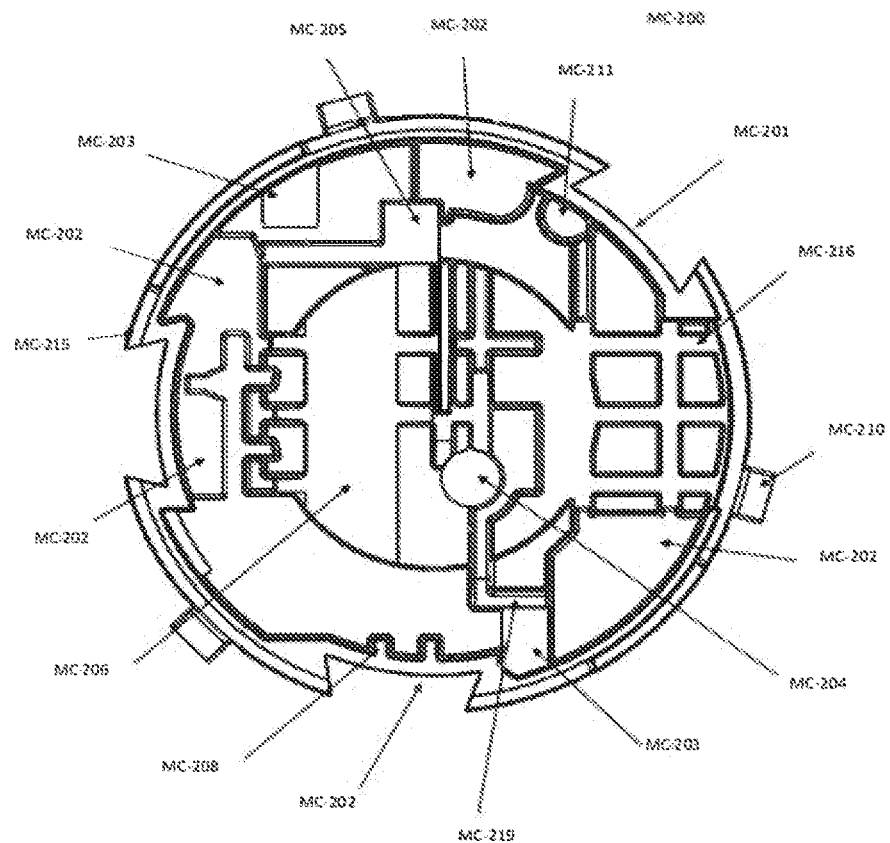
Figure 24:
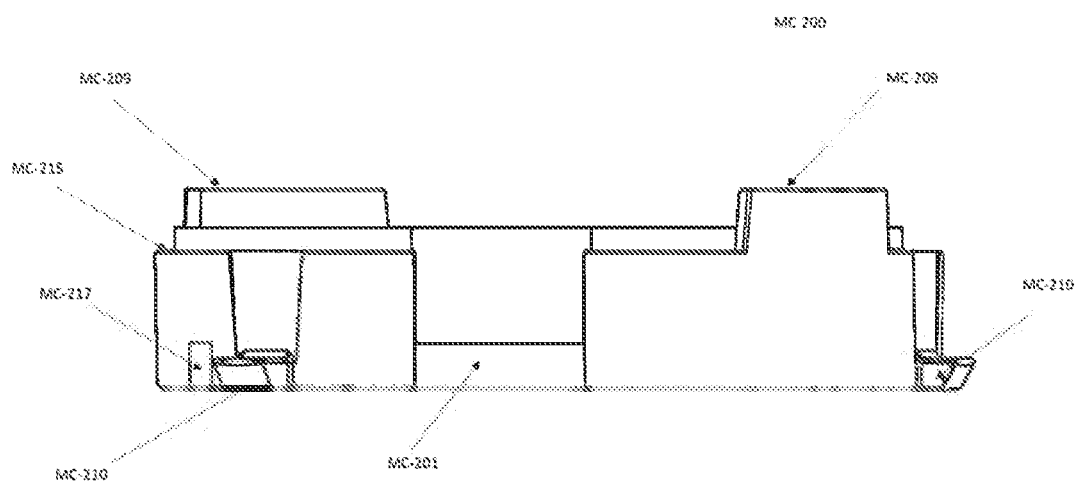
Figure 25:
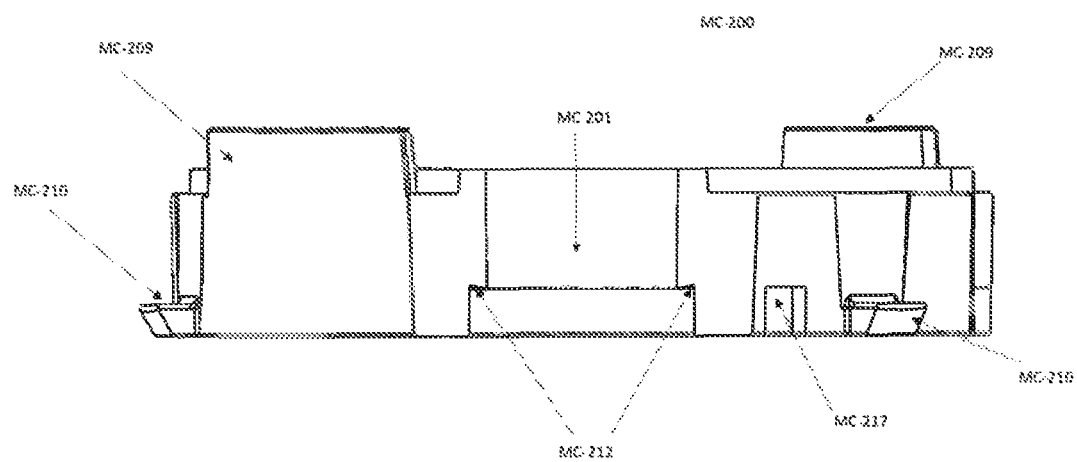

2.) Following the removal of the safety mechanism SS-200, the user can rotate the sealed housing MC-200, MC-300 from the locked position MC-117 to the unlocked position MC-118, whereupon the sealed housing MC-200, MC-300 is automatically moved to the armed position MC-119 by a biasing member SS-300. As a result, the housing MC-200, MC-300 translates and rotates a certain constrained distance and angle. When the user applies a force and transitions the sealed housing MC-200, MC-300 from the armed position MC-119 to the injection position MC-120, the mechanisms that initiate the internal activation sequences inside the sealed housing MC-200, MC-300 are triggers or protrusions MC-106, MC-107 (see, e.g., FIGS. 15-16). The activation triggers or protrusions MC-106, MC-107 can be molded or formed on a surface of the cover MC-100. Cavities MC-202 (see, e.g., FIGS. 22-23) are molded or formed into the lower half MC-200 of the sealed housing MC-200, MC-300 to allow the sealed housing MC-200, MC-300 and the cover MC-100 to rotate and translate relative to one another without interfering with or damaging the activation mechanism MC-106, MC-107 or alignment mechanism MC-105 (see, e.g., FIGS. 19-20). During the assembly, activation, and injection, the protrusions or tabs MC-210, molded or formed on the sealed housing MC-200, MC-300 and corresponding channels, slots, detents, etc. MC-103 on the cover MC-100, may interface to provide sufficient clearance and alignment to prevent damage of the protrusions or triggers on the cover MC-105, MC-106, MC-107. The cover MC-100 may also have alignment posts or protrusions MC-105, that interface with corresponding cavities MC-211 (see, e.g., FIG. 23) in the sealed housing MC-200, MC-300 at the time of injection (e.g., when the auto-injector 1 is in position MC-120) such that they may aid in the alignment of the sealed housing MC-200, MC-300 and cover MC-100 to orient the triggers MC-106, MC-107 on the cover MC-100 with the corresponding locking mechanisms NES-500 (see, e.g., FIGS. 38-41), MDS-100 (see, e.g., FIGS. 69-73) disposed in the sealed housing MC-200, MC-300. In some embodiments, the cover MC-100 and/or sealed housing MC-200, MC-300 may contain additional features (e.g., MC-103, MC-104, MC-109, MC-115, MC-210, SS-102) that aid in maintaining alignment between the sealed housing MC-200, MC-300 and the cover MC-100 during relative movement.

Figure 98:
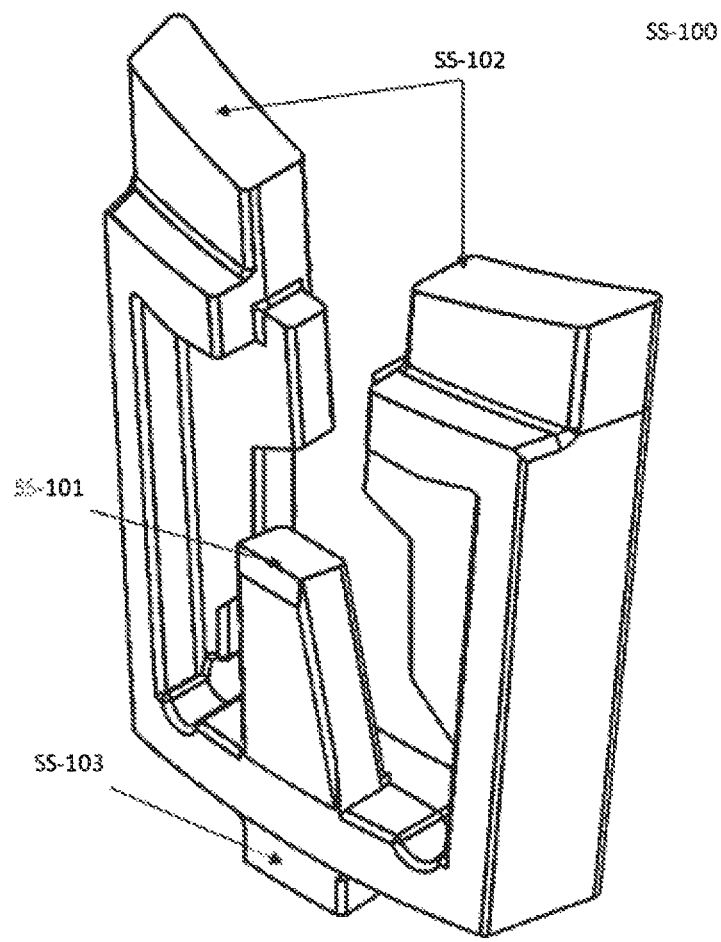
Figure 99:
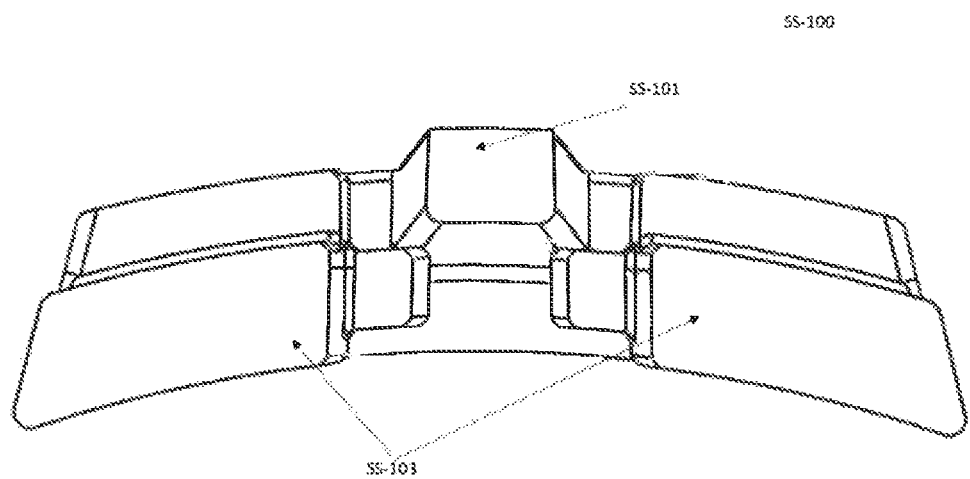
Figure 100:
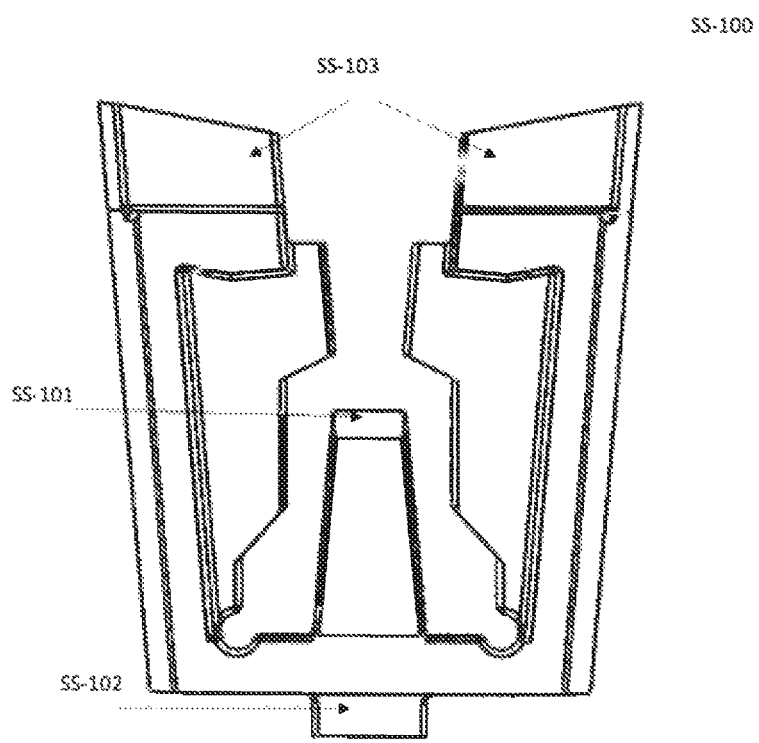
Figure 103:
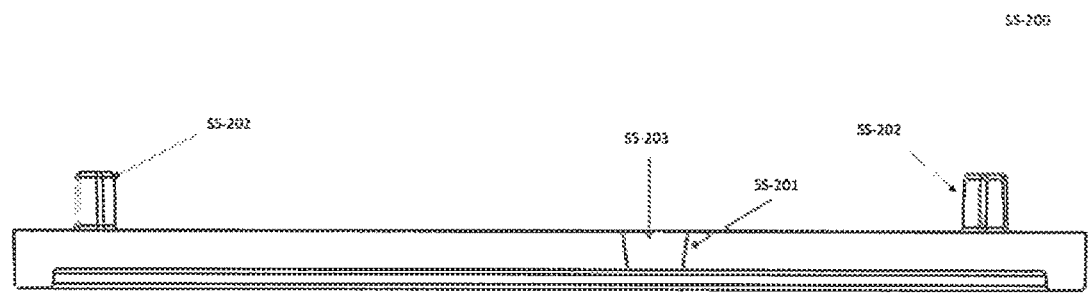
Figure 104:
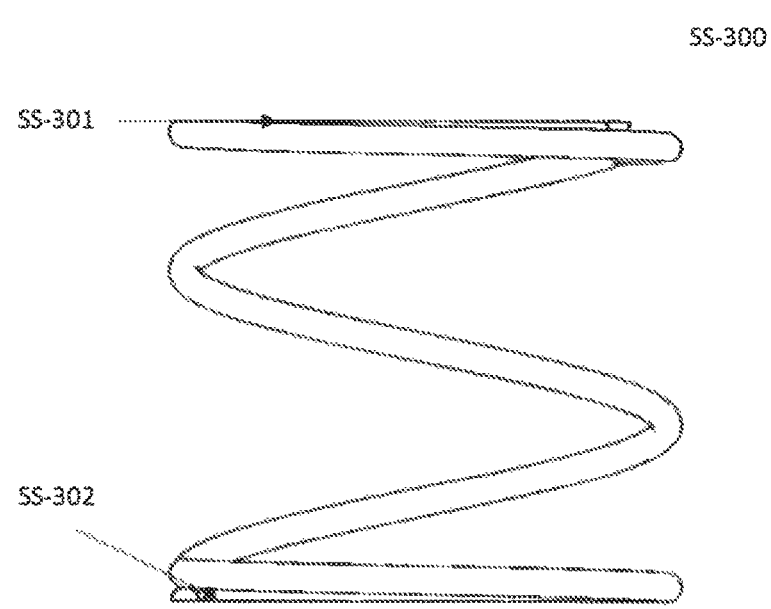

3.) When the user applies a force to the top surface MC-300 of the sealed housing MC-200, MC-300 to compresses the sealed housing MC-200, MC-300 into the cover MC-100 to perform the injection, the first system to be activated may be the interlock system SS-100. Activating the interlock system SS-100 first, ensures that when the user deploys the needle extension system (NES), the interlock system SS-100 will always engage the triggering mechanism MC-109. In some embodiments, the interlocks SS-100 are activated by an interference fit between the cover MC-109 and interlock SS-101 (see, e.g., FIGS. 98-100) when the sealed housing MC-200, MC-300 is compressed during injection. Following the injection, and the release of pressure on the sealed housing MC-200, MC-300, the sealed housing MC-200, MC-300 may be automatically displaced relative to the cover MC-100, and the interlocks SS-100 are deployed or engaged. Prior to activation, the interlocks SS-100 can be held in a stored state in cavities MC-201 (see, e.g., FIG. 103), MC-314 (see, e.g., 29-34) in the sealed housing MC-200, MC-300.

Figure 31:
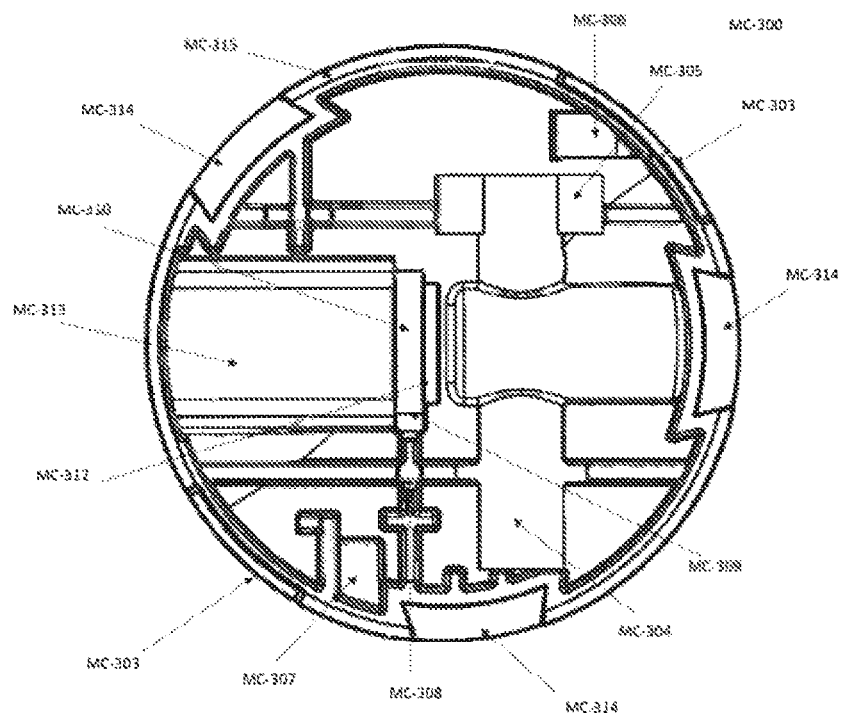
Figure 32:
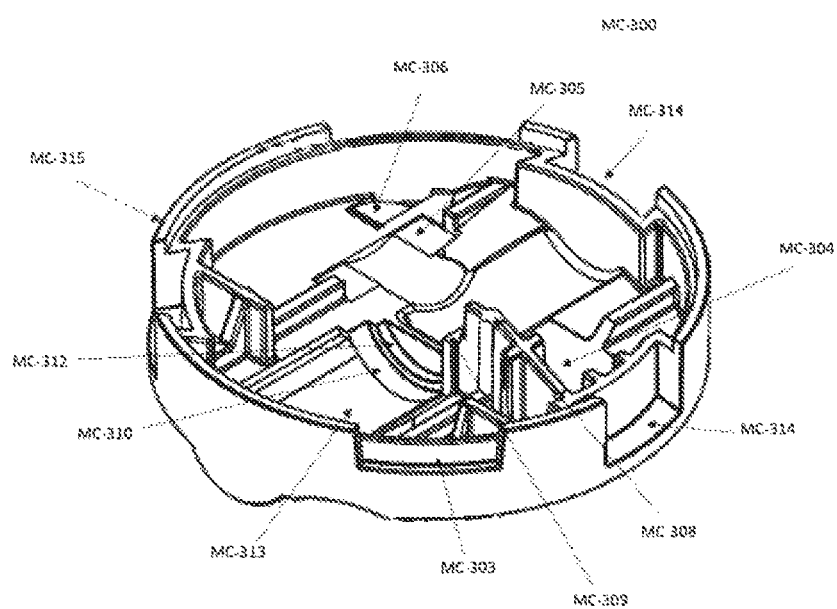
Figure 33:
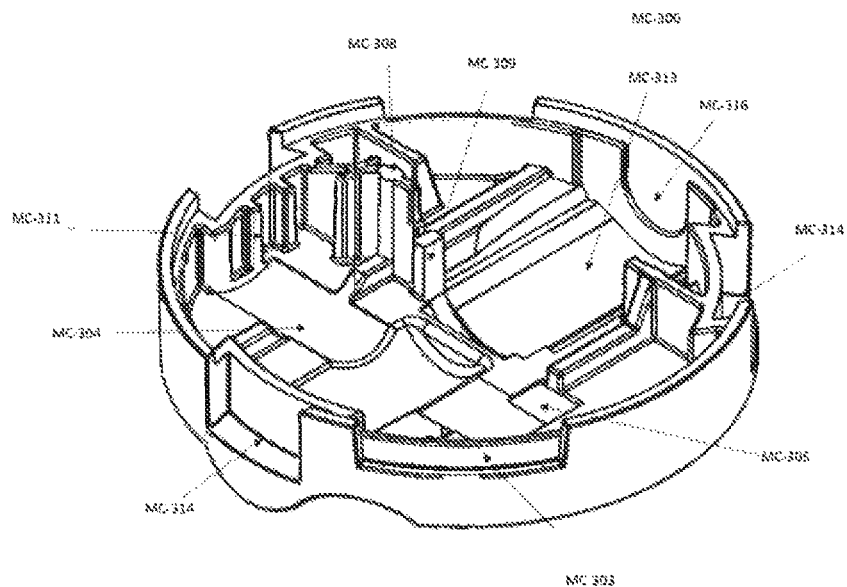
Figure 34:
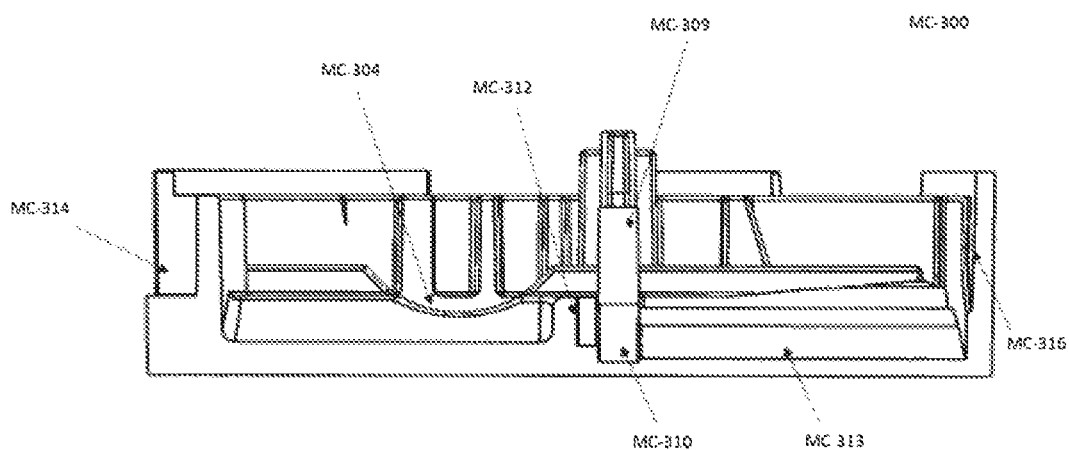
Figure 35:
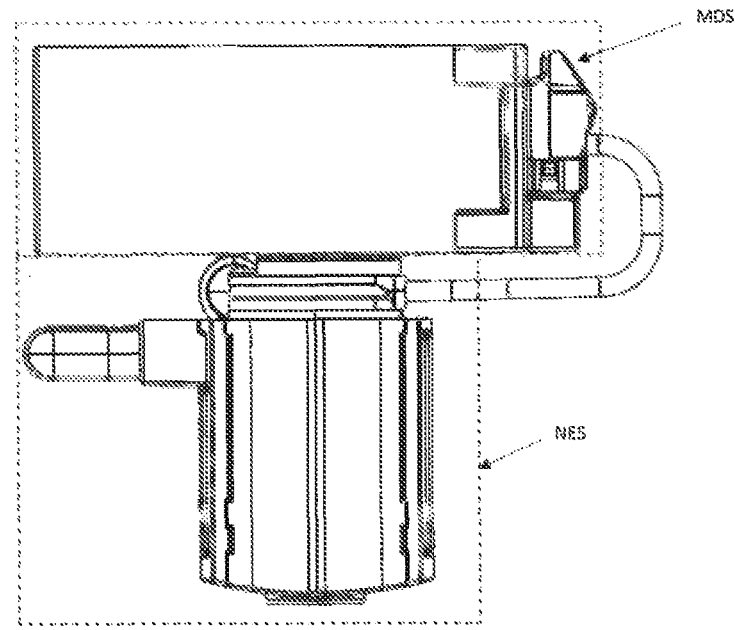
Figure 36:
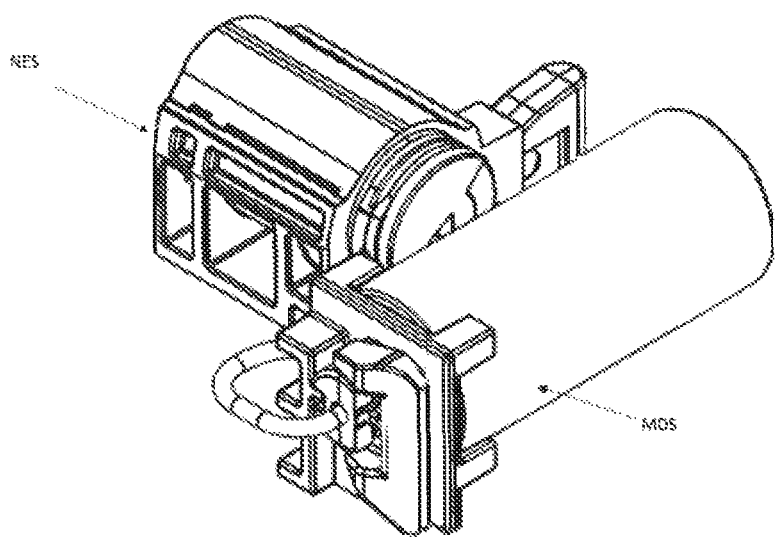
Figure 37:
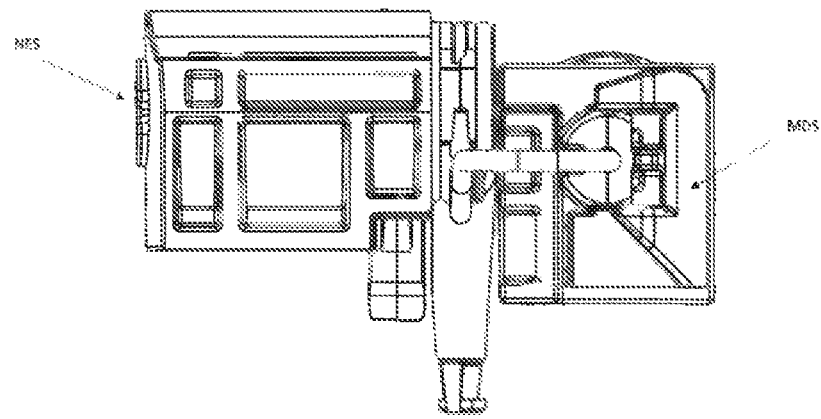
Figure 47:
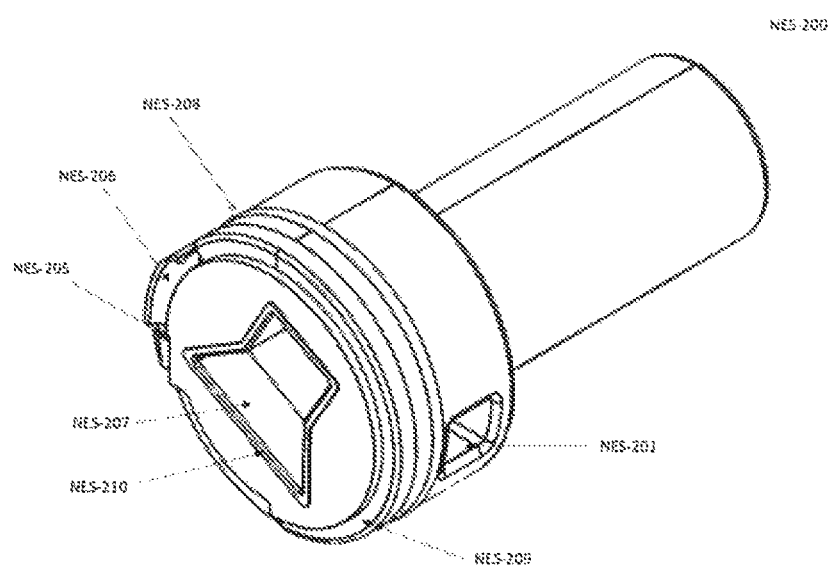
Figure 48:
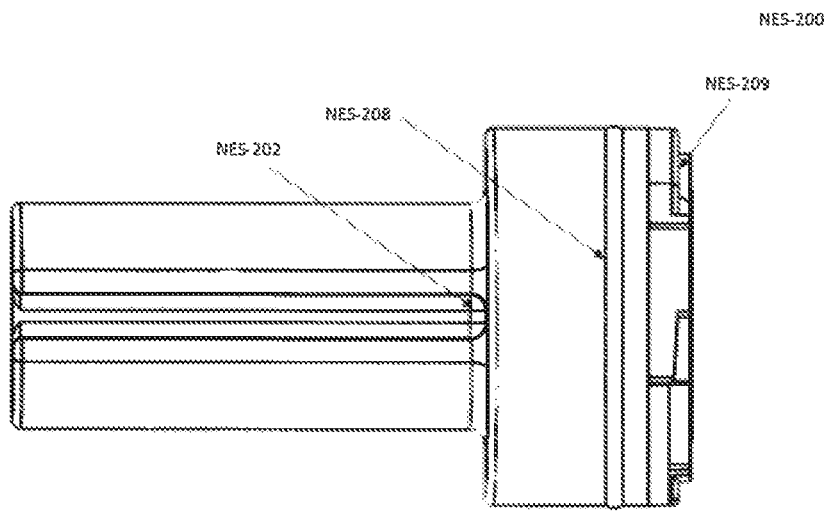
Figure 49:
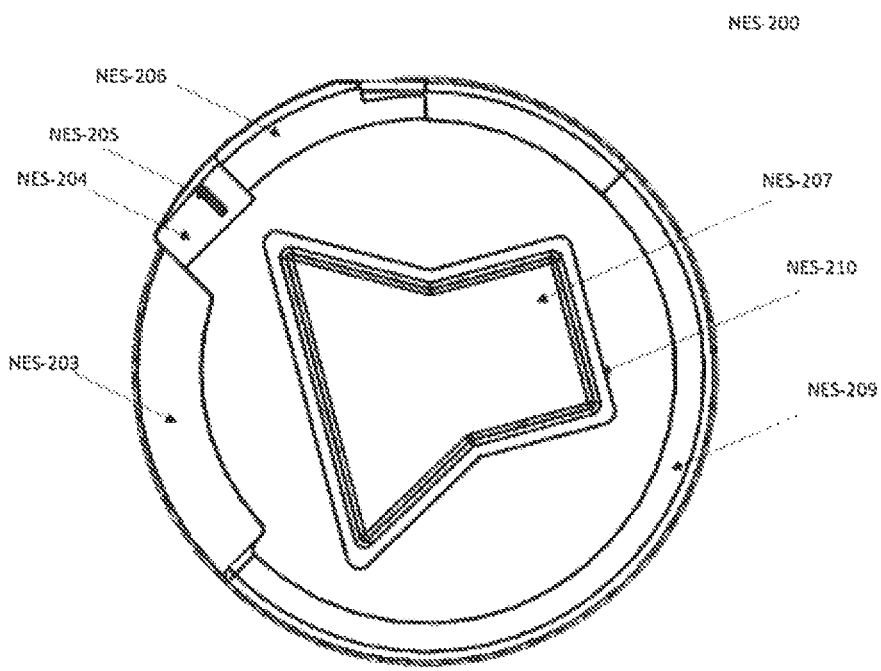
Figure 50:
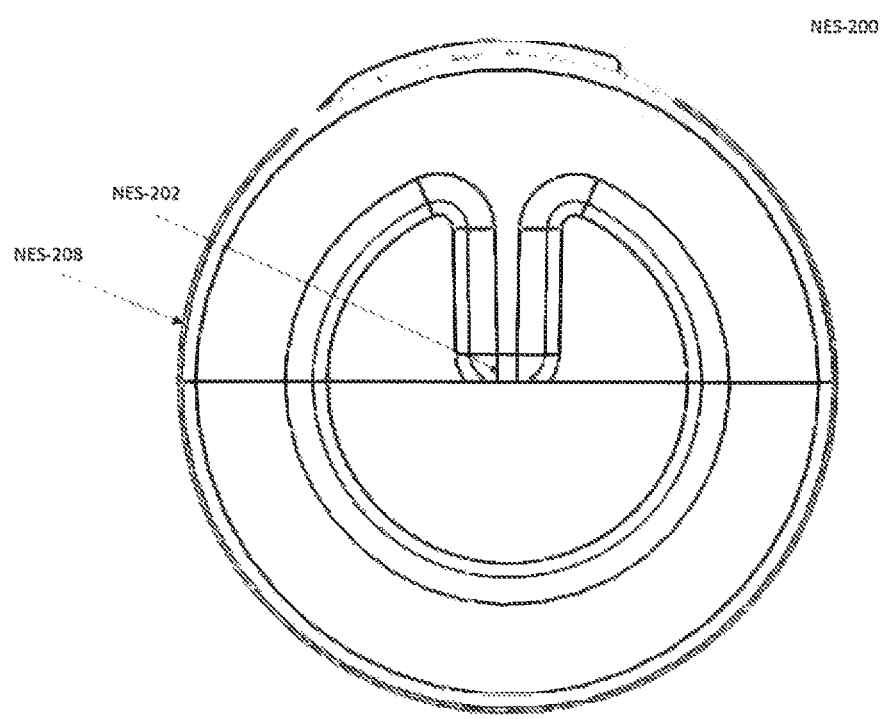
Figure 60:
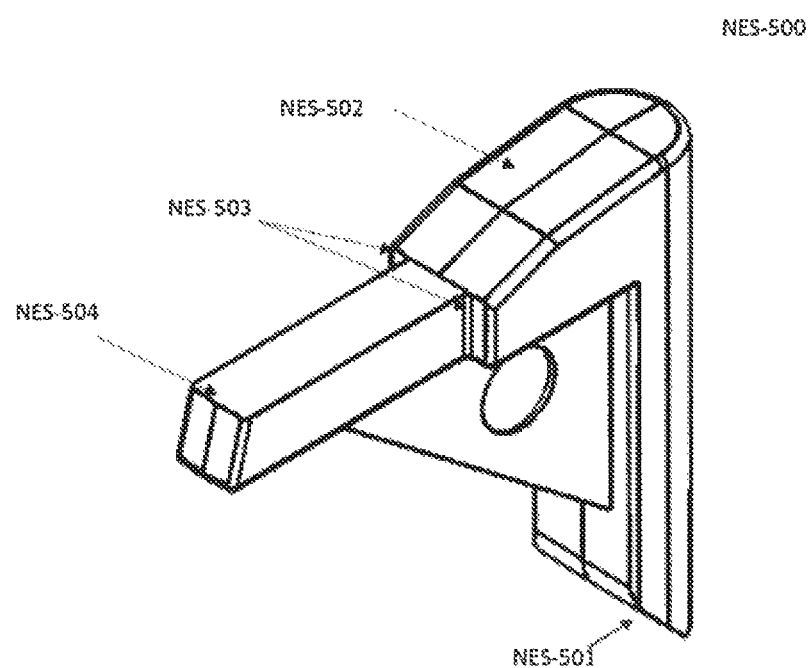
Figure 61:
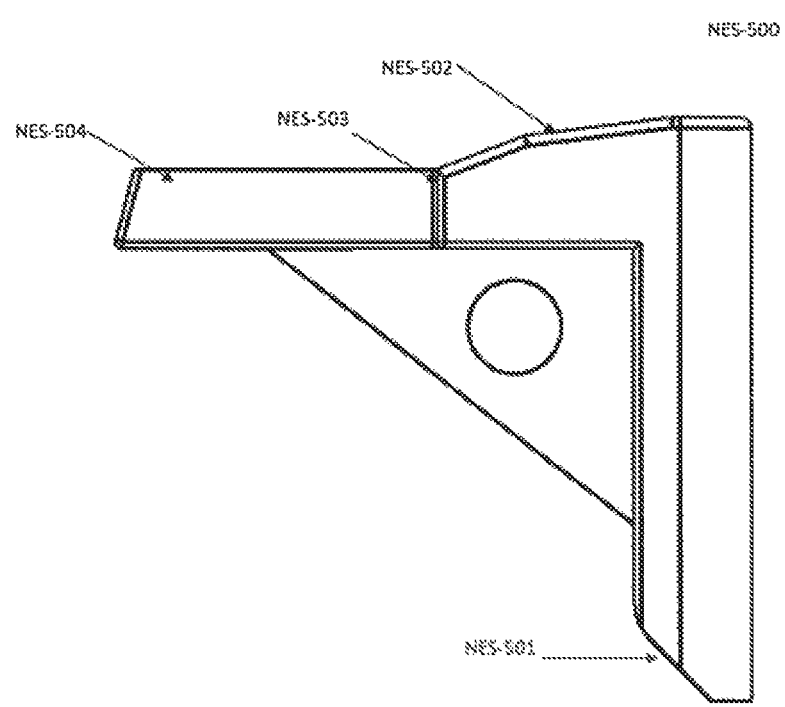
Figure 62:
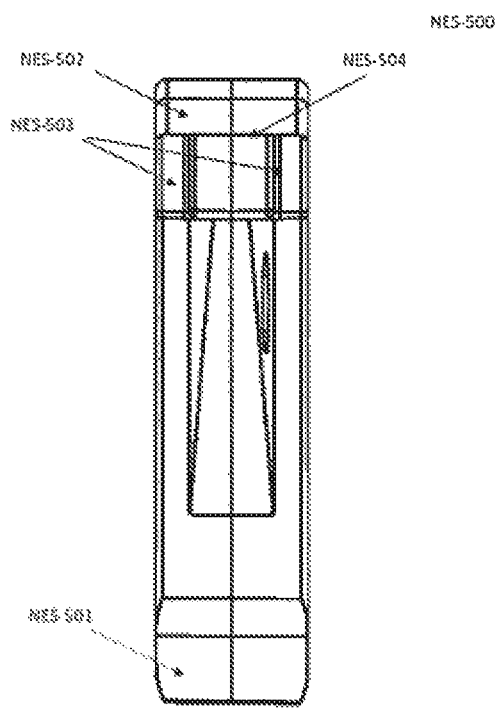
Figure 63:
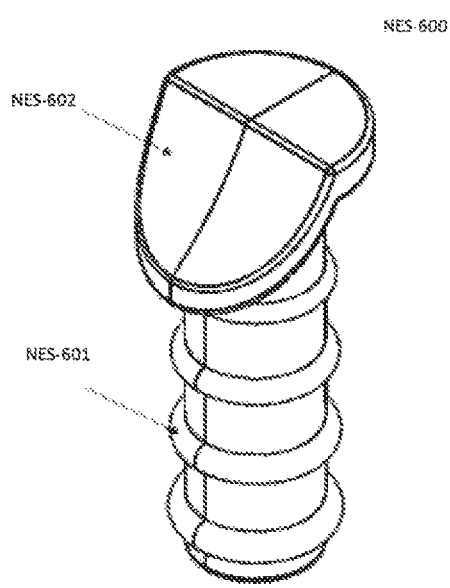
Figure 64:
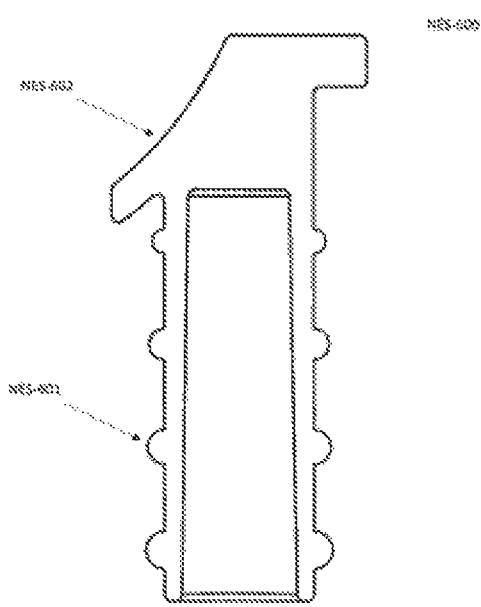
Figure 67:
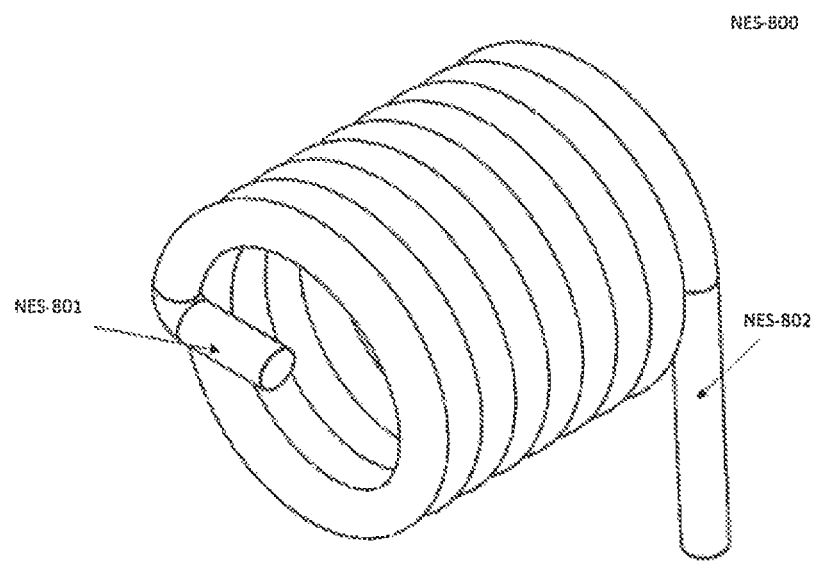
Figure 68:
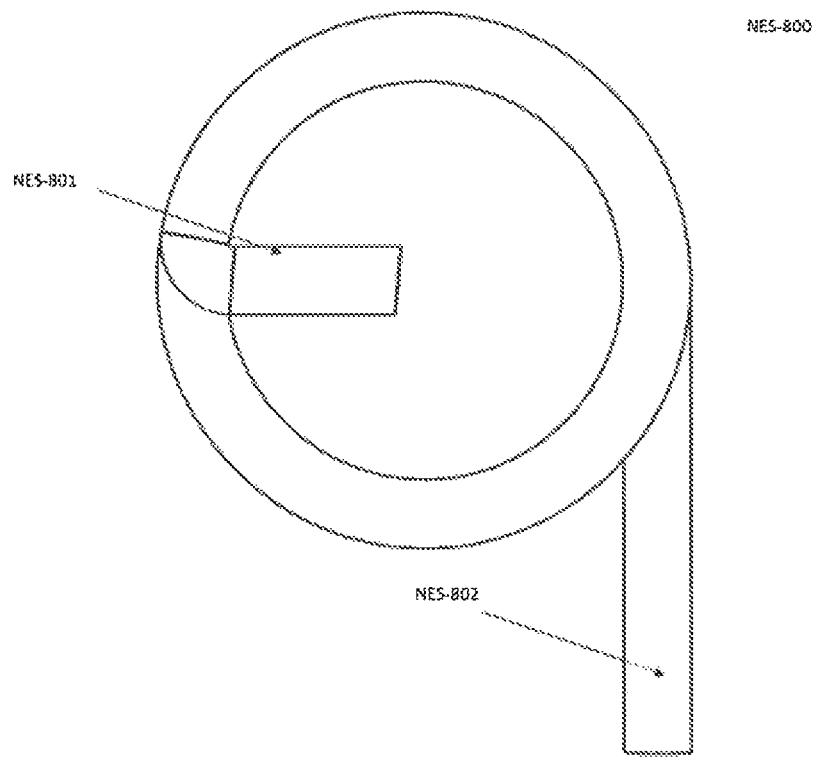
Figure 69:
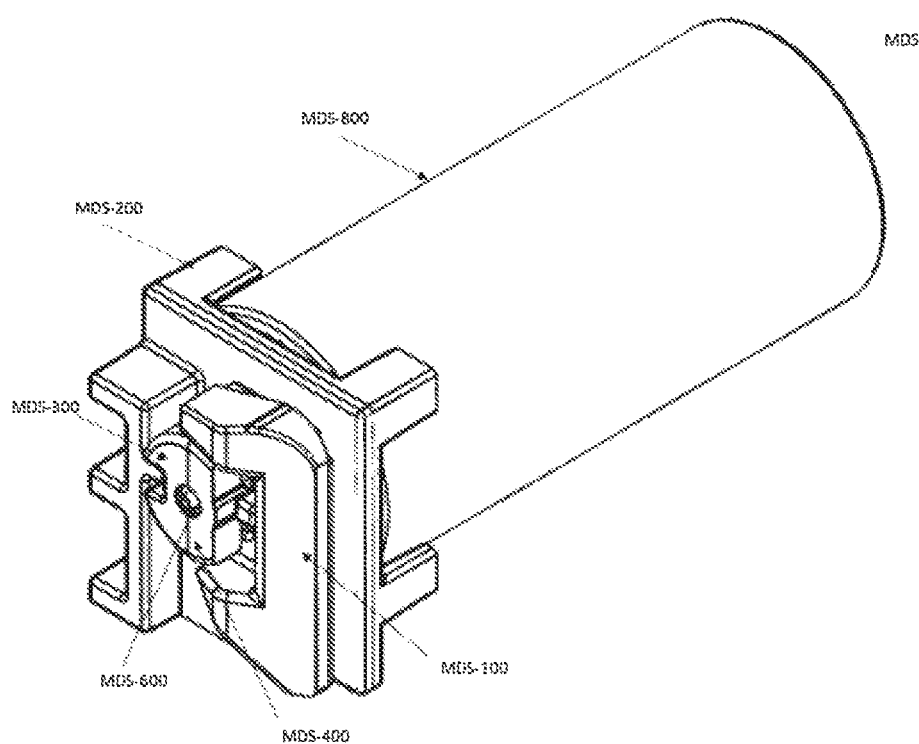
Figure 70:
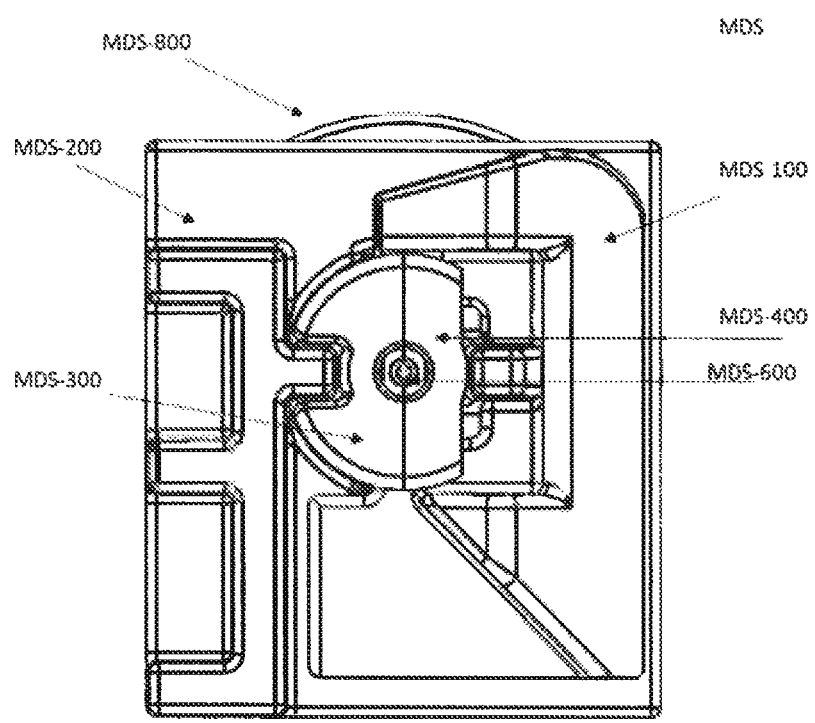
Figure 71:
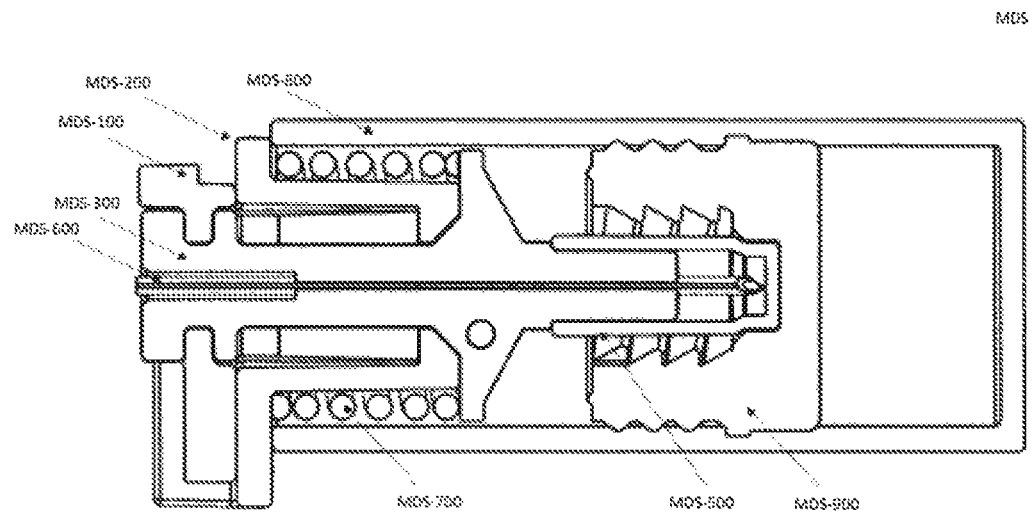
Figure 72:
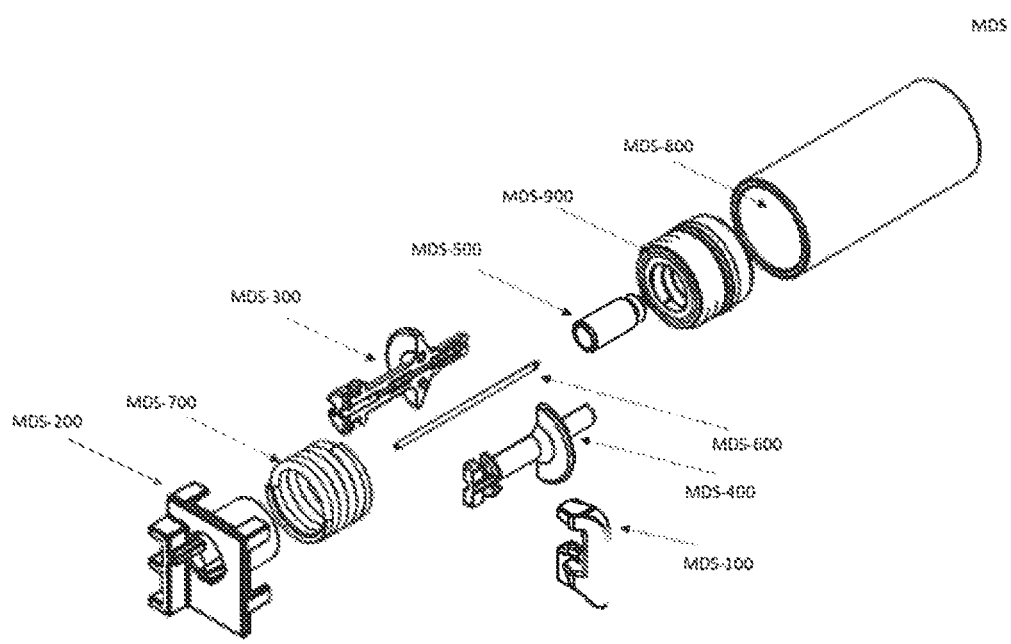
Figure 73:
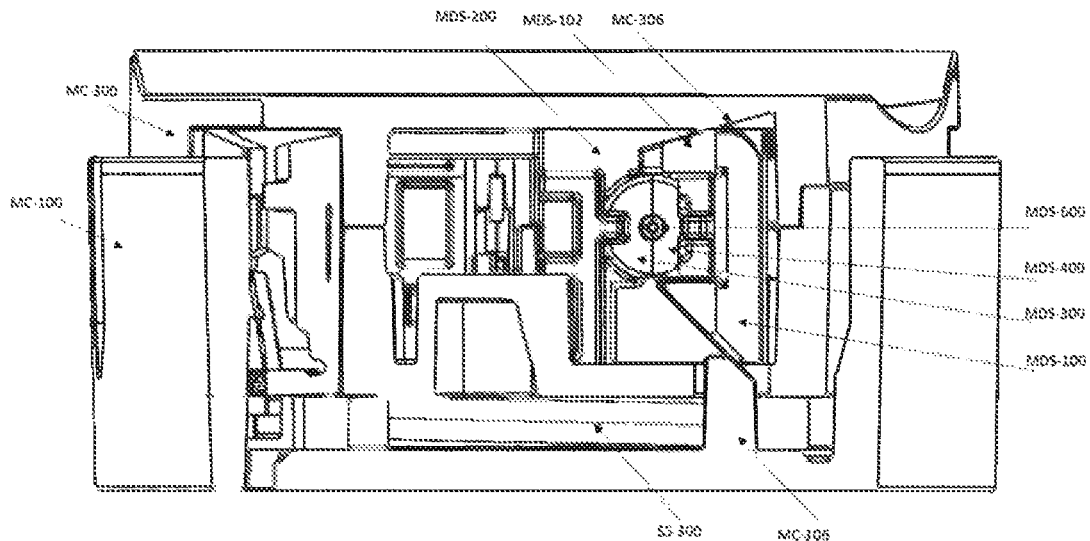

4.) Following the activation of the interlocks SS-100, the needle extension system (NES) can be activated. The corresponding needle extension trigger or protrusion MC-107 on the cover MC-100 breaks the plane of the sealed housing MC-200, MC-300 in a predetermined location MC-203 (see, e.g., FIG. 23) and contacts the fixture or locking mechanism NES-500 of the NES. The fixture or locking mechanism NES-500 of the NES can preserve the potential energy of a biasing member NES-800 (see, e.g., FIGS. 67-68). The biasing member NES-800 may be coupled to the needle barrel NES-200 (see, e.g., FIGS. 46-50) at a specified contact point NES-202 (see, e.g., 48-50). In one embodiment the biasing member NES-800 is a torsion spring which rotates the needle barrel NES-200. The fixture or locking mechanism NES-500 may maintain the potential energy of the torsion spring NES-800 by an interference portion NES-201 (see, e.g., FIG. 47) with the needle barrel NES-200. The contact portion NES-501 (see, e.g., FIGS. 60-62) between the needle extension trigger or protrusion MC-107 on the cover MC-100 and the fixture or locking mechanism NES-500 disengages the locking mechanism NES-500, releasing the potential energy stored in the torsion spring NES-800. The release of the torsion spring NES-800 rotates the needle barrel NES-200 and deploys the curved injection needle NES-700. The housing may have an internal geometric portion MC-307 (see, e.g., FIG. 31) to facilitate the disengagement of the locking mechanism NES-500 at the time of injection.

Figure 51:
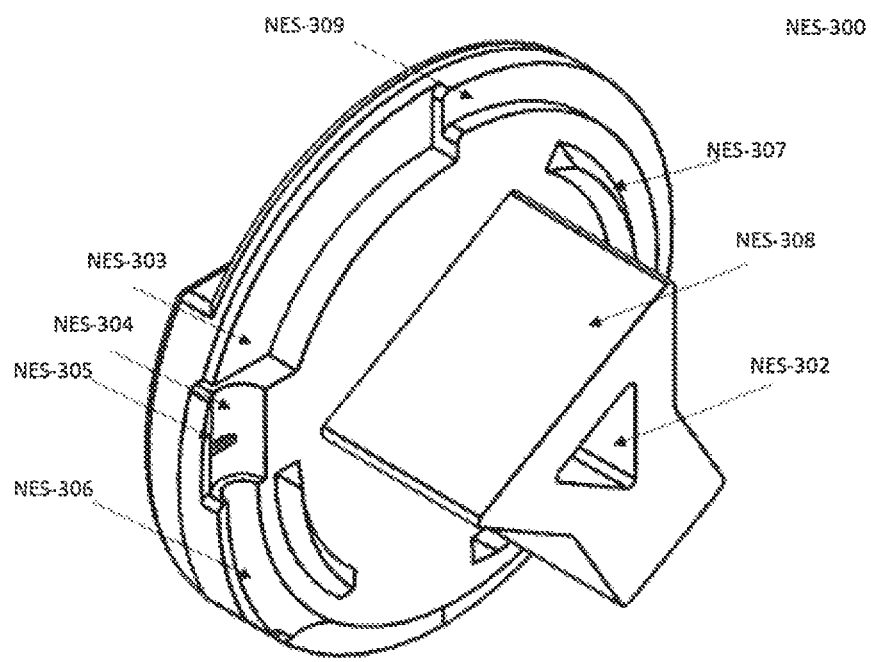
Figure 52:
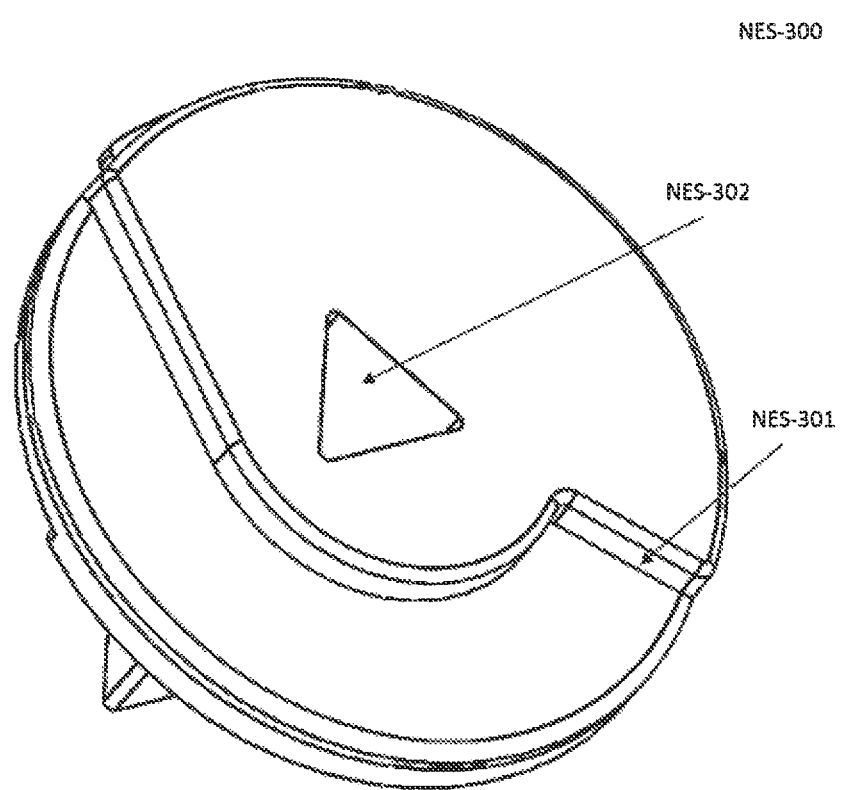
Figure 53:
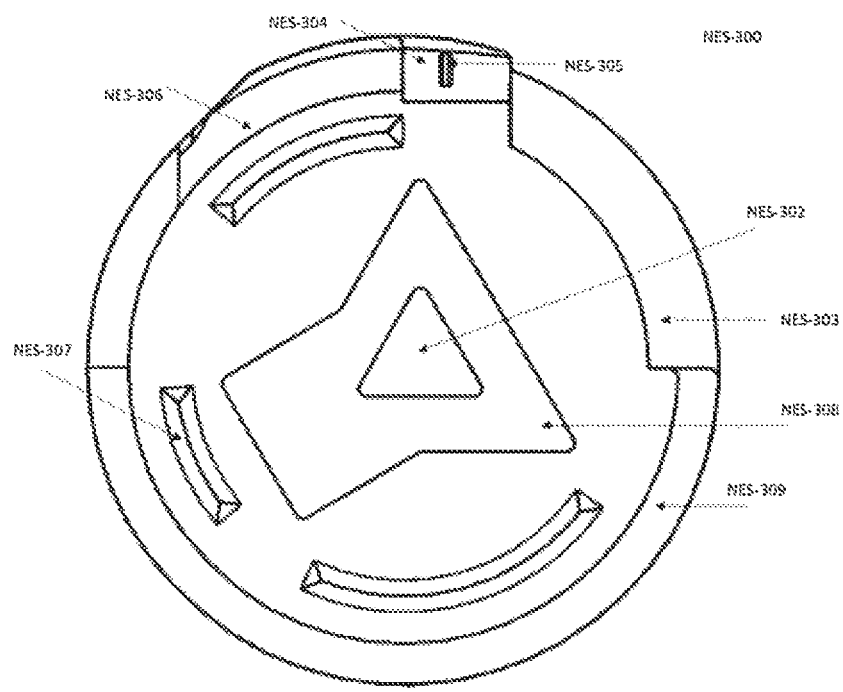
Figure 54:
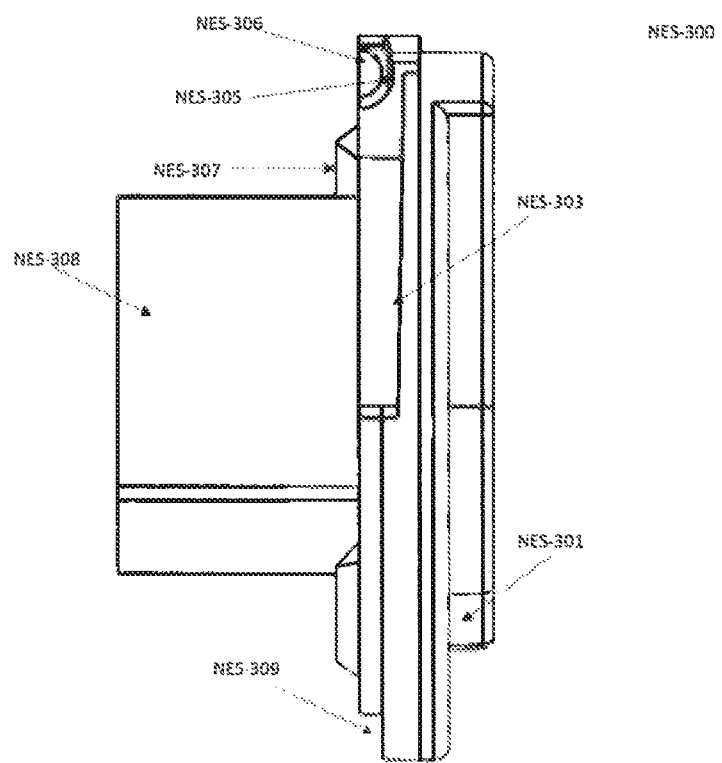
Figure 55:
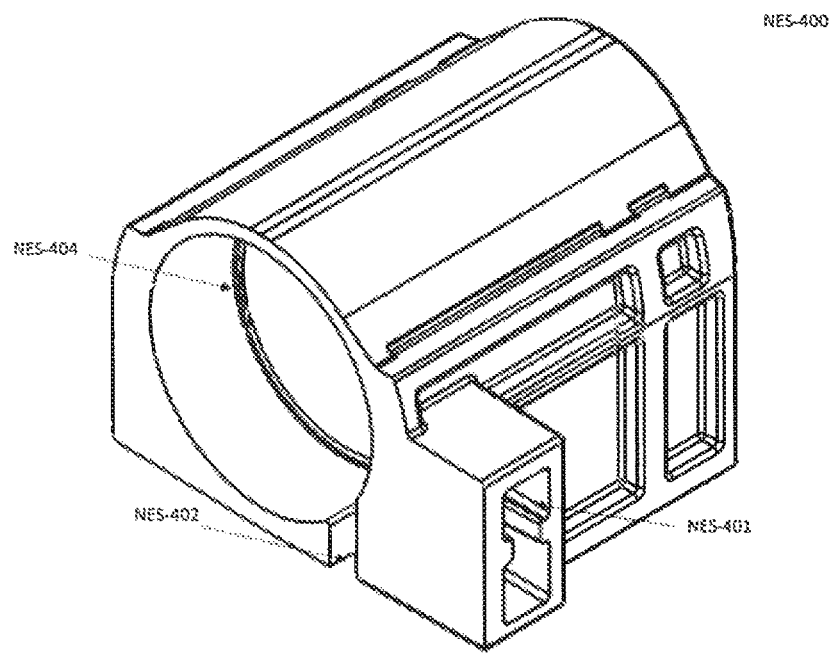
Figure 56:
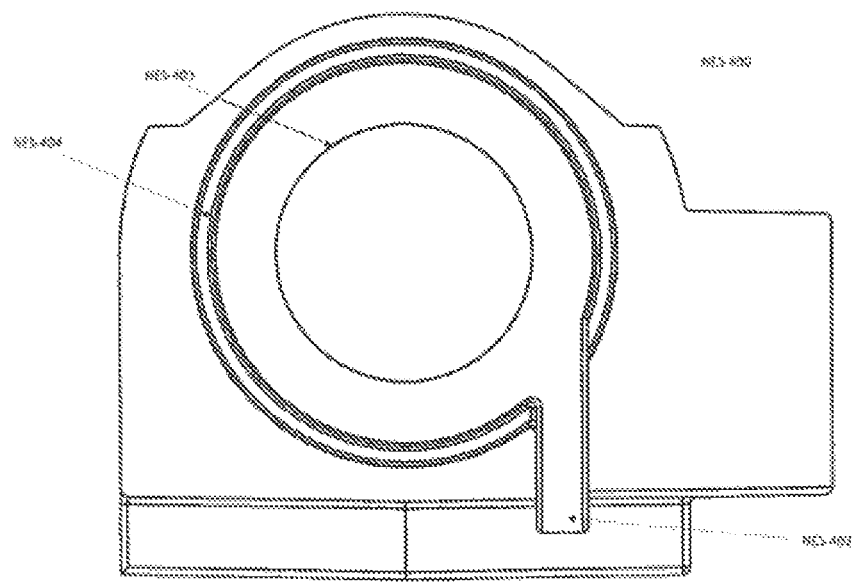
Figure 57:
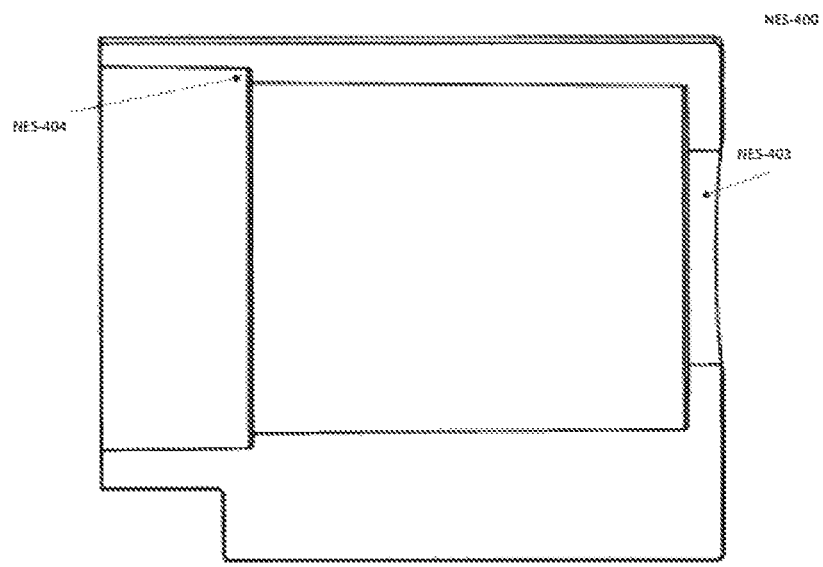
Figure 58:
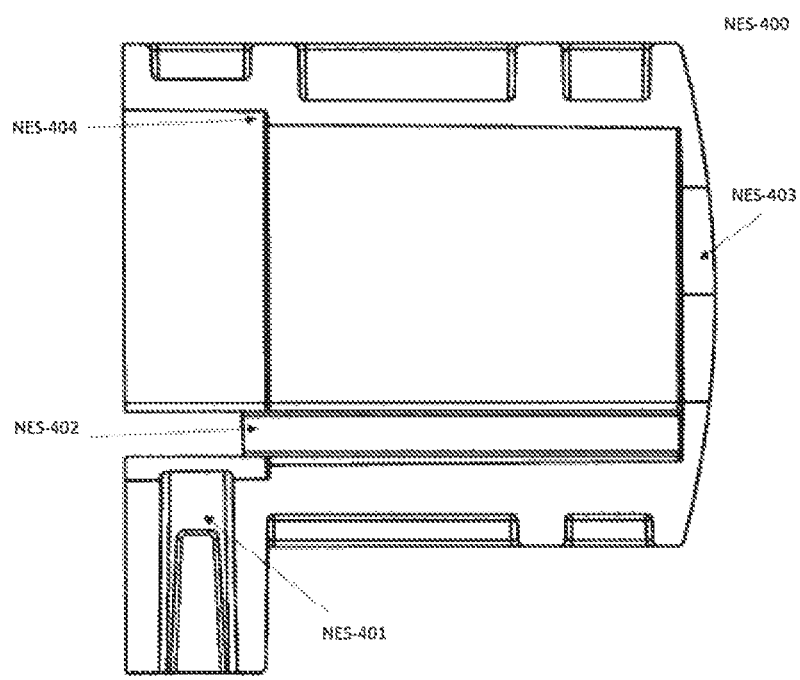
Figure 59:
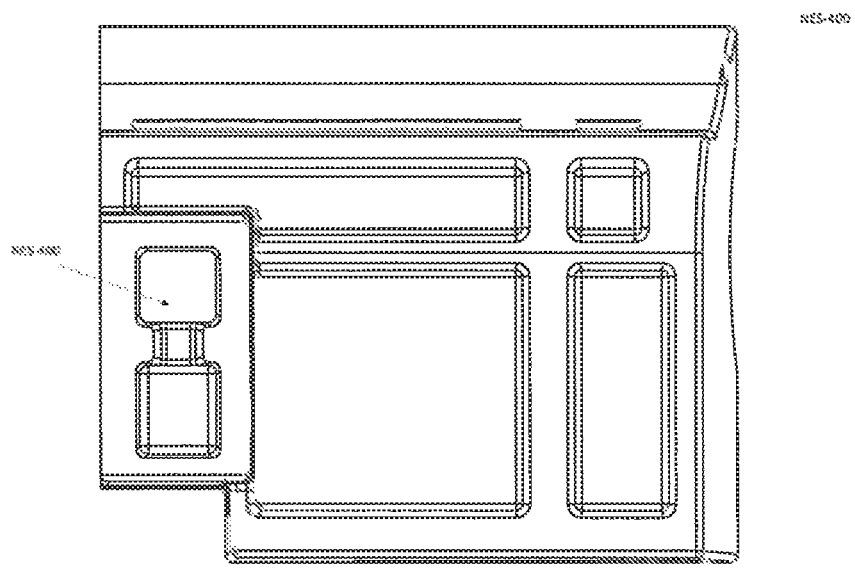

5.) Once the locking mechanism NES-500 is disengaged from the needle barrel NES-200, the torsion spring NES-800 may rotate the needle barrel NES-200. The injection needle NES-700 may be fixed to and retained in the needle barrel NES-200 by a needle barrel cap NES-300 (see, e.g., FIGS. 51-54) that mates element NES-308 (see, e.g., FIGS. 53-54) with a corresponding recess NES-207 formed in the needle barrel NES-200. The needle barrel cap NES-300 may secure the injection needle NES-700 to the needle barrel NES-200 through a friction fit between elements NES-306 (see, e.g., FIGS. 53-54), NES-206 (see, e.g., FIGS. 46-47). In addition, the barrel cap NES-300 may secure a flexible tubing NES-900 (see FIG. 40) to the injection needle NES-700 through a friction or compression fitting formed by elements NES-304 (see FIG. 51), NES-305 (see FIG. 51), NES-204 (see FIG. 49), NES-205 (see FIG. 49). Furthermore, the needle barrel cap NES-300 provides a contact surface NES-301 (see FIG. 52) for limiting the needle barrel's NES-200 rotation to a specific angle. In various embodiments, the bottom half MC-200 of the sealed housing MC-200, MC-300 provides an interface MC-218 (see, e.g., FIGS. 21-22) which contacts the needle barrel cap NES-300 during rotation to limit the angular displacement of the barrel NES-200 to the desired rotation angle, proportional to the desired injection depth. The barrel cap NES-300 and the bottom half MC-200 of the sealed housing MC-200, MC-300 work together to prevent the injection needle NES-700 from over rotating and ensure that the proper injection depth is achieved. The needle barrel NES-200 maintains alignment along its rotational axis during rotation through guides (e.g., NES-203 (see FIG. 46), NES-303 (see FIG. 51), NES-208 (see FIG. 48)) formed in the sealed housing MC-200, MC-300 halves (e.g., MC-207, MC-312, MC-316, MC-302, MC-310, MC-309, MC-216) as well as a needle barrel guide NES-400 (see FIGS. 55-59). These guides may maintain axial alignment and prevent the needle barrel NES-200 and injection needle NES-700 from translating relative to the sealed housing MC-200, MC-300 during injection. The needle barrel guide NES-400 may also provide a channel NES-401 (see FIG. 55) to brace and guide the NES locking mechanism NES-500 (see, e.g., FIGS. 60-62) during auto-injector 1 storage and injection. In some embodiments the needle barrel cap NES-300 can be ultrasonically welded (see welds NES-210 (FIG. 49), NES-307 (FIG. 51) or utilize another means of joining the two components together. Additionally, the NES components of the system can be integrated independent of the housing MC-200, MC-300, during assembly.

Figure 66:
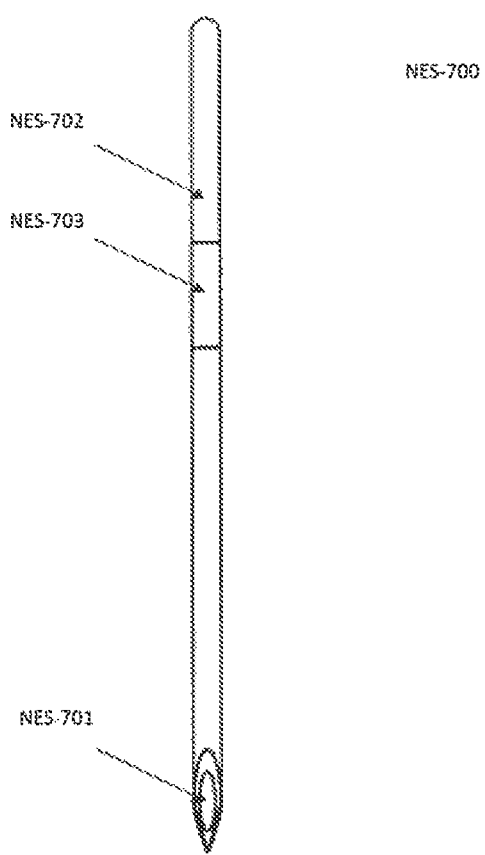

6.) Upon rotation of the injection needle NES-700, the distal end NES-701 (see FIGS. 65-66) of the curved injection needle passes through an aperture MC-204 (see FIG. 23) formed in the lower half MC-200 of the sealed housing MC-200, MC-300 and makes contact with a needle guide MC-110 (see FIG. 19) on the cover MC-100, such that a portion of the curved injection needle NES-700 is straightened during uncoiling. The location where the injection needle NES-700 contacts the surface MC-112, MC-113 (see FIG. 19) on the needle guide MC-110 may be such that the distal end NES-701 (e.g., a lancet) is not in contact with the guide MC-110 to mitigate the chance of scoring or scraping the needle guide MC-110, and to mitigate the chance of producing debris. In addition to the needle guide MC-110, the sealed housing MC-200, MC-300 may provide a brace MC-309 (see FIGS. 31-34) to further limit possible radial (with respect to the needle axis) deflections during injection.

Figure 74:
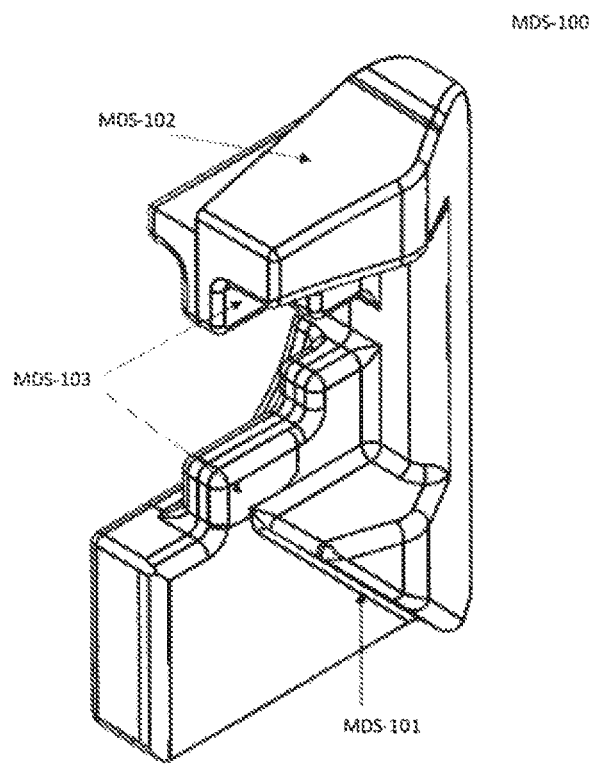
Figure 75:
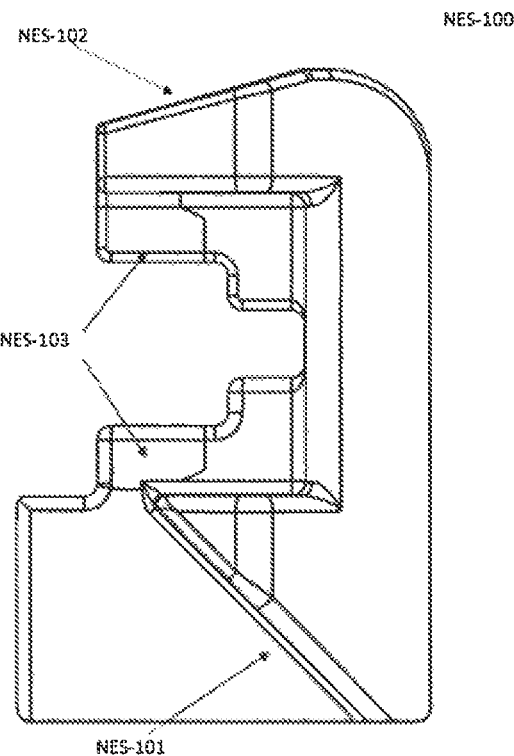
Figure 76:
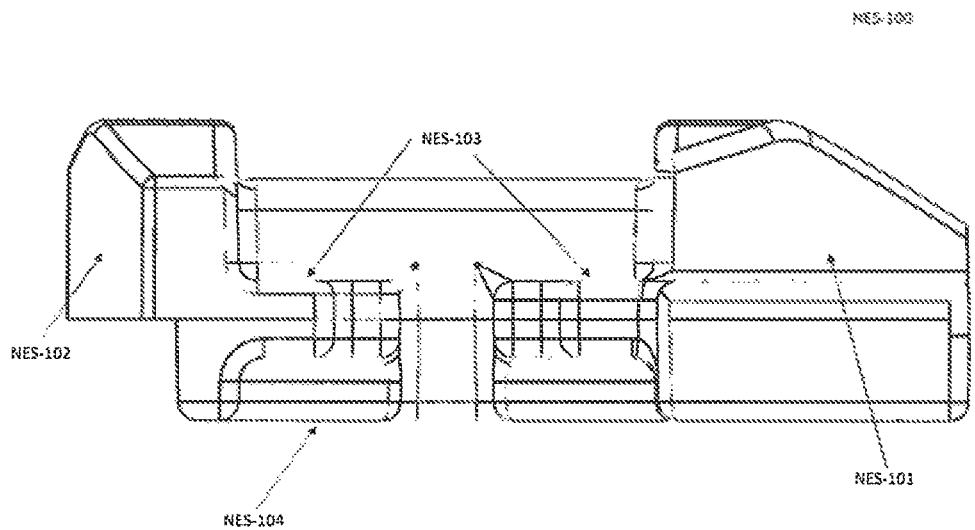
Figure 77:
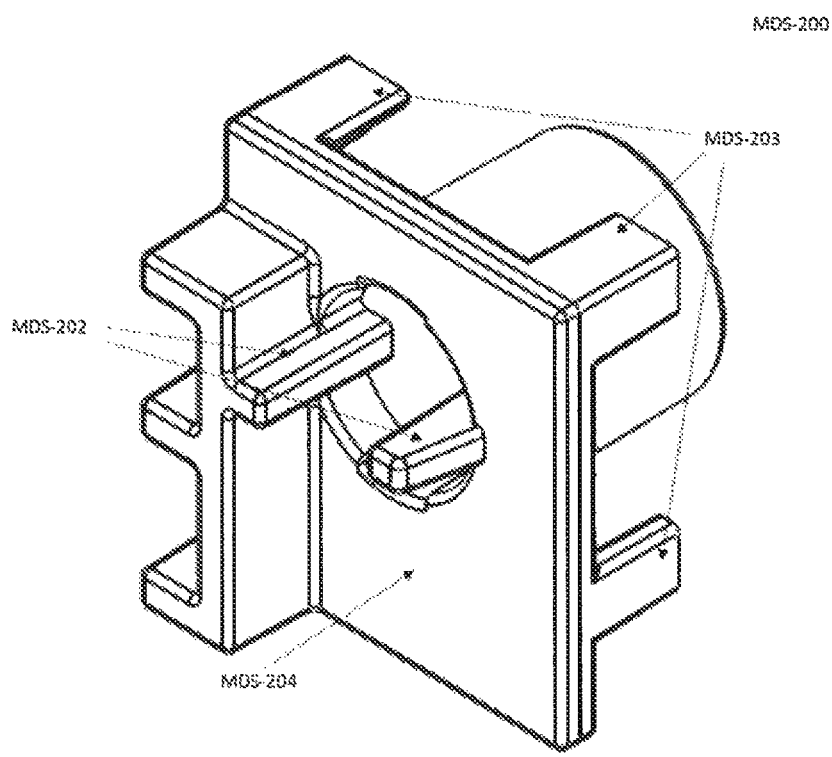
Figure 78:
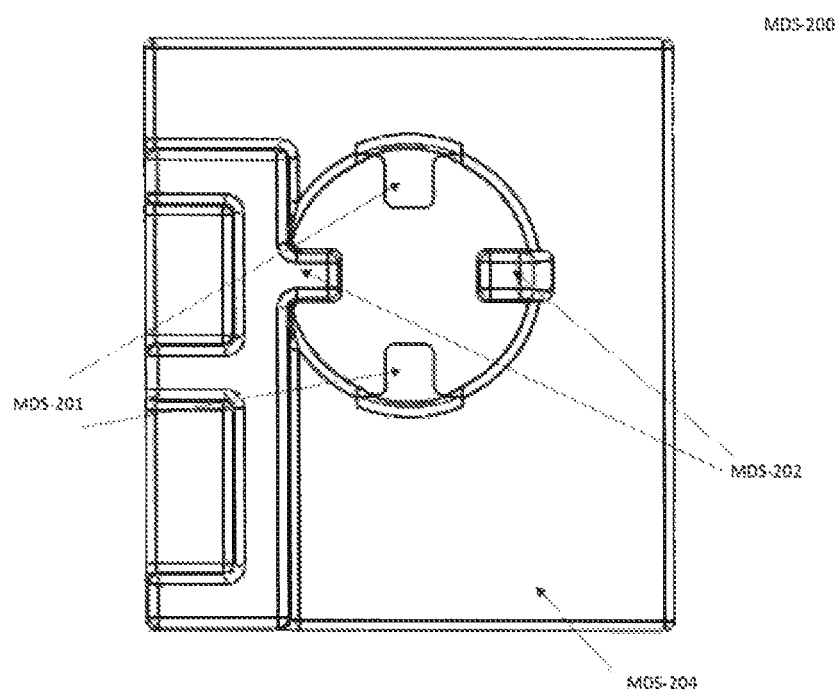
Figure 79:
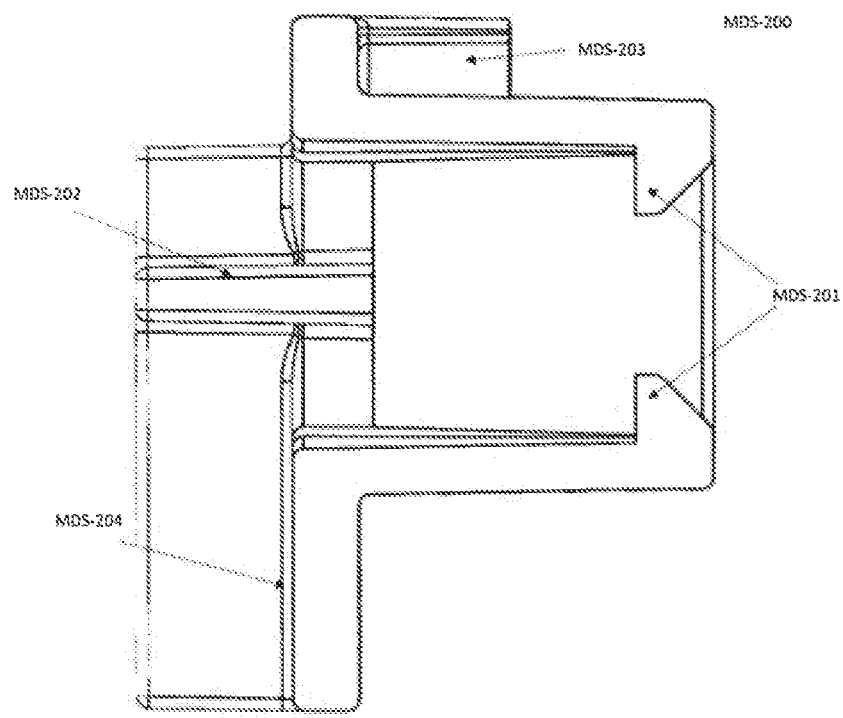
Figure 80:
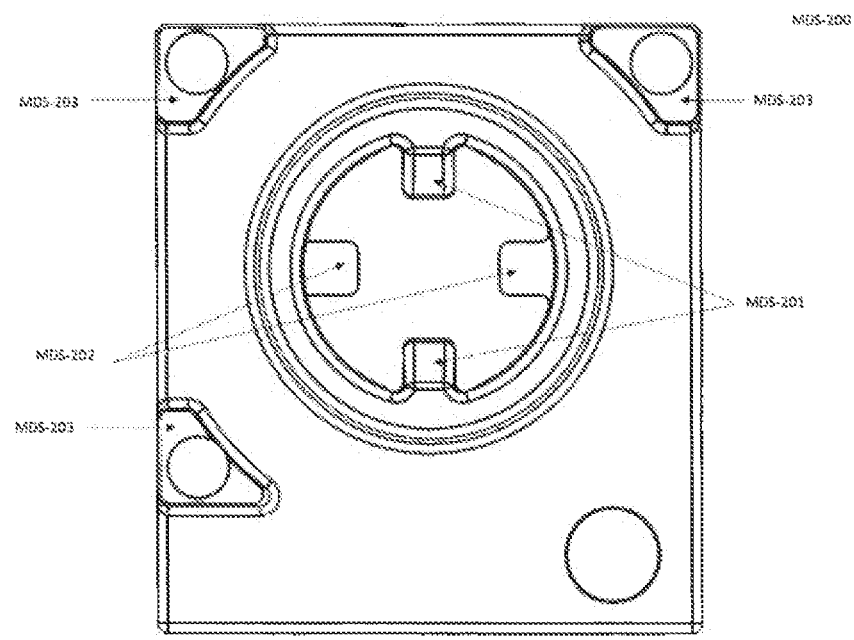
Figure 81:
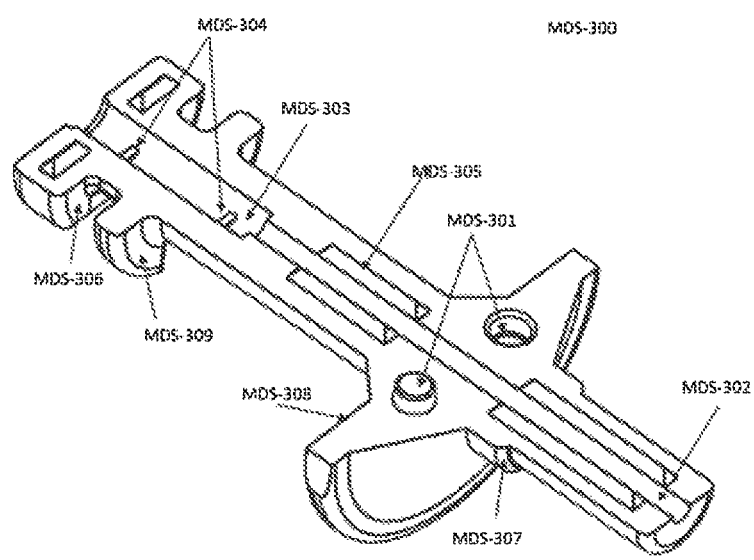
Figure 82:
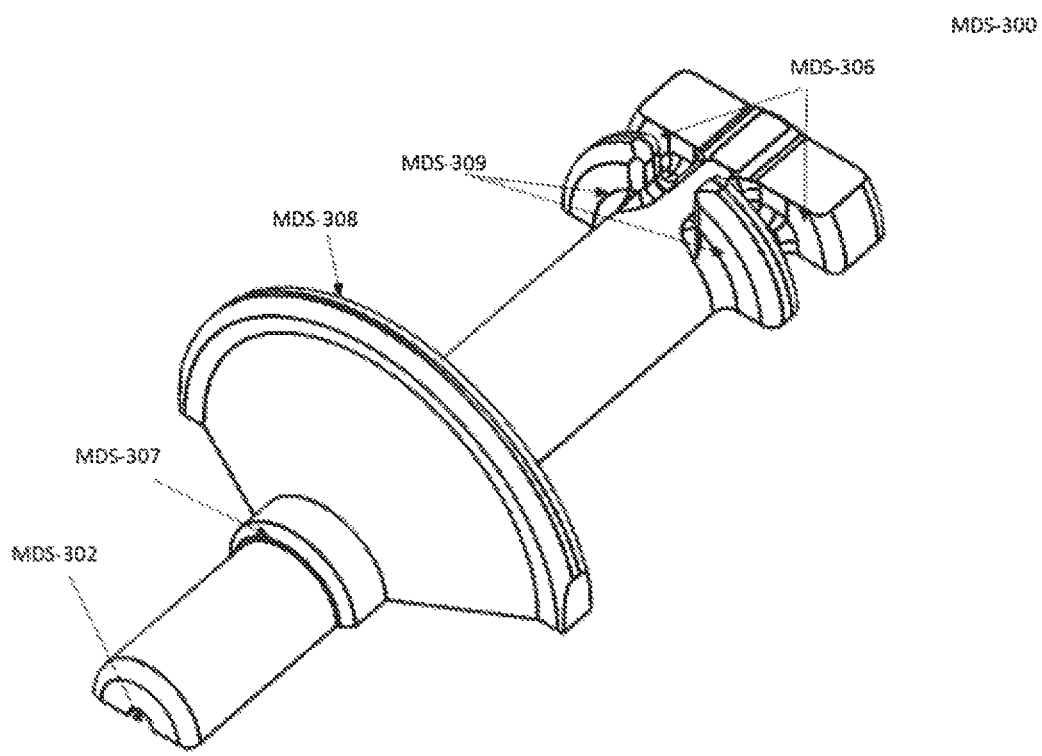
Figure 83:
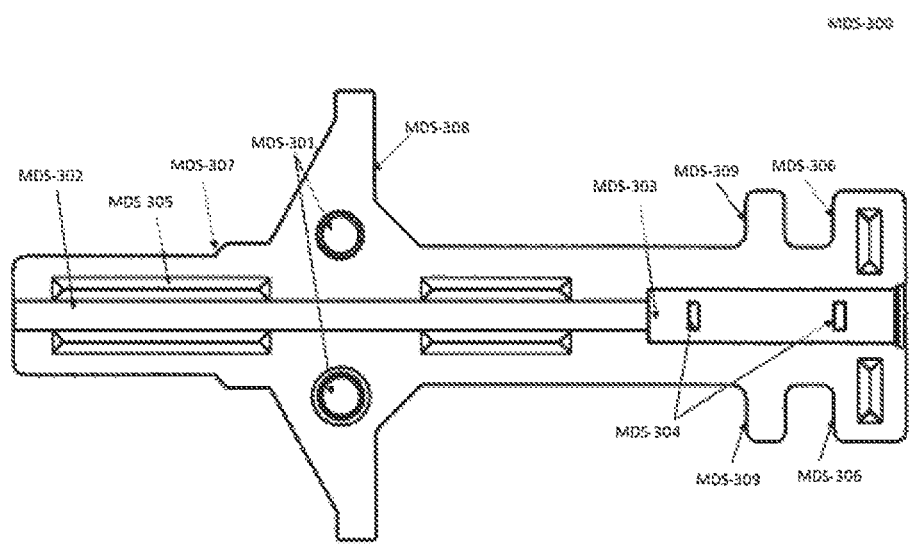
Figure 84:
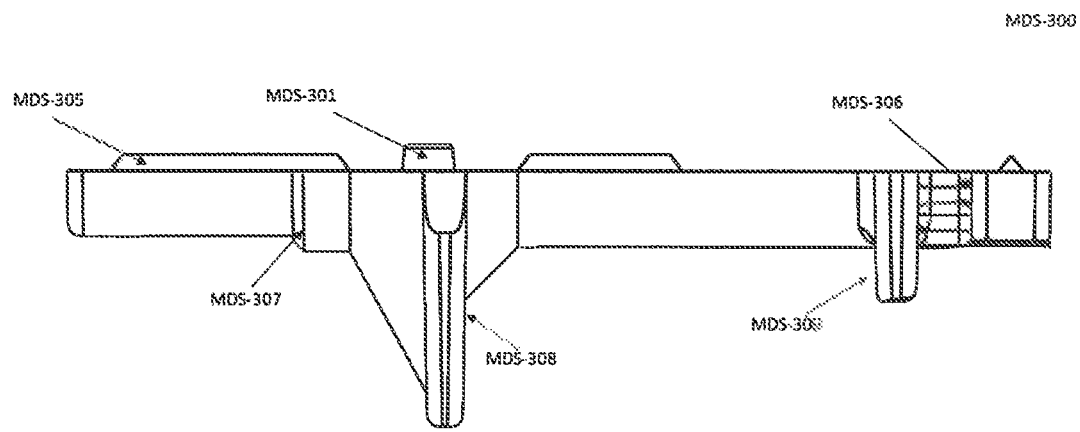
Figure 85:
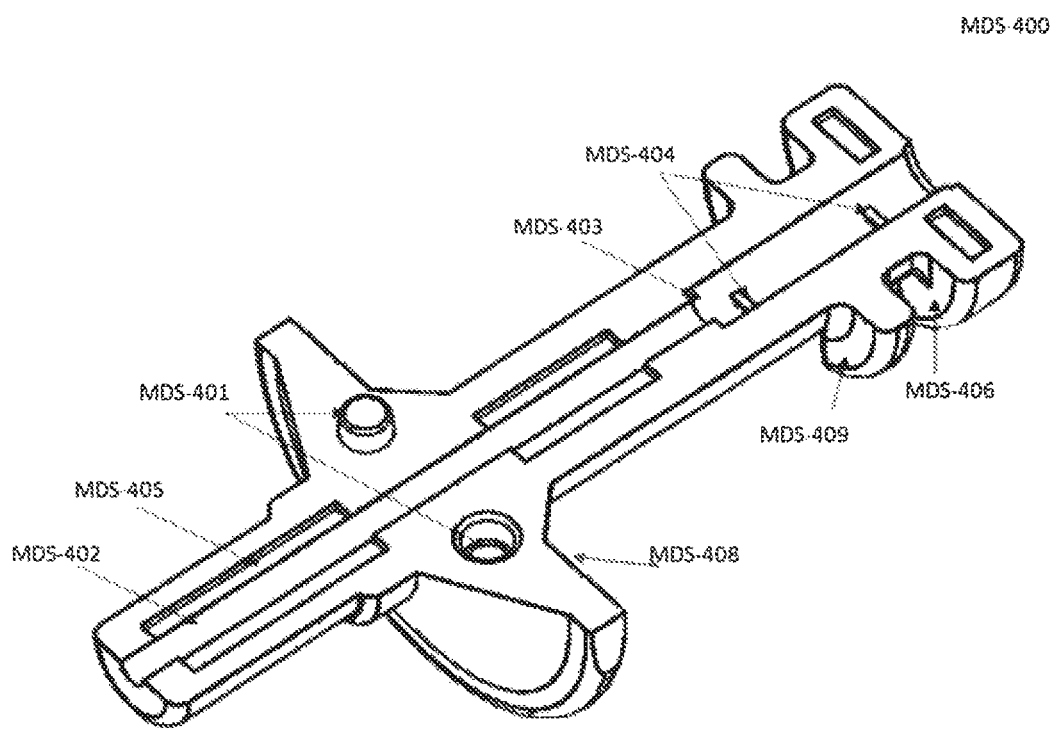
Figure 86:
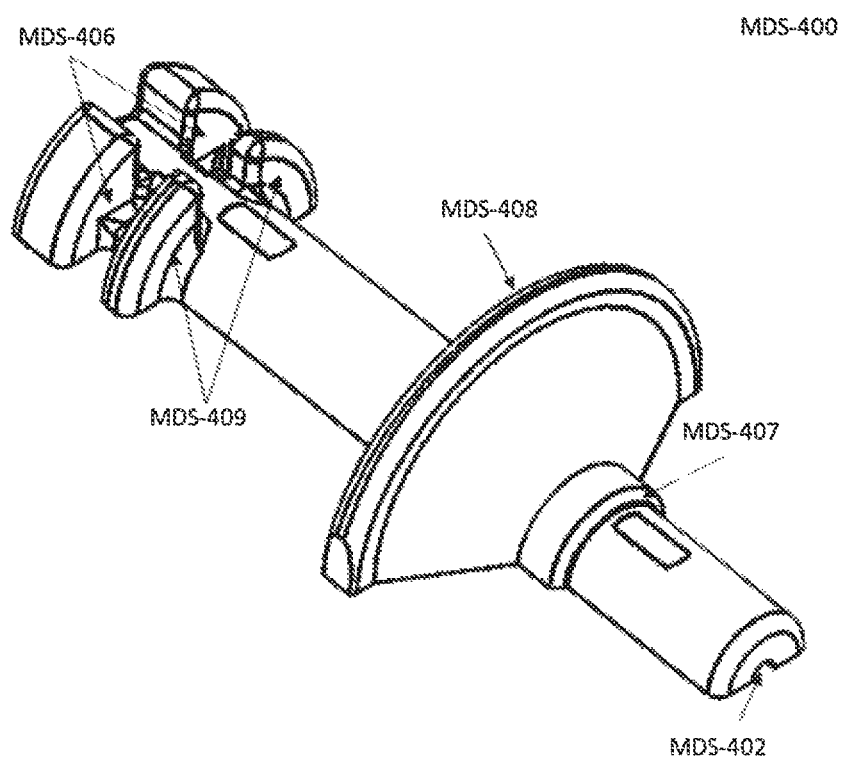
Figure 87:
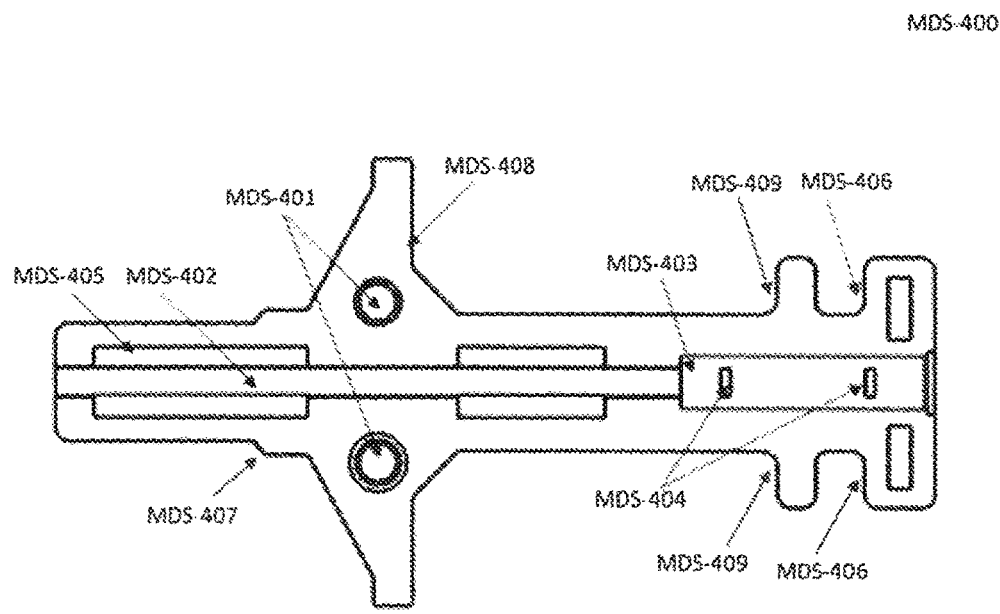
Figure 88:
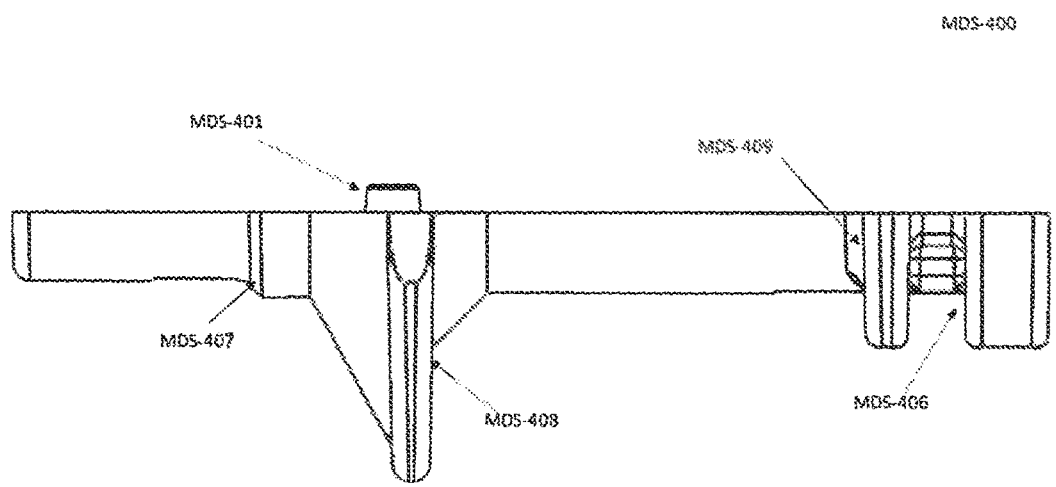
Figure 94:
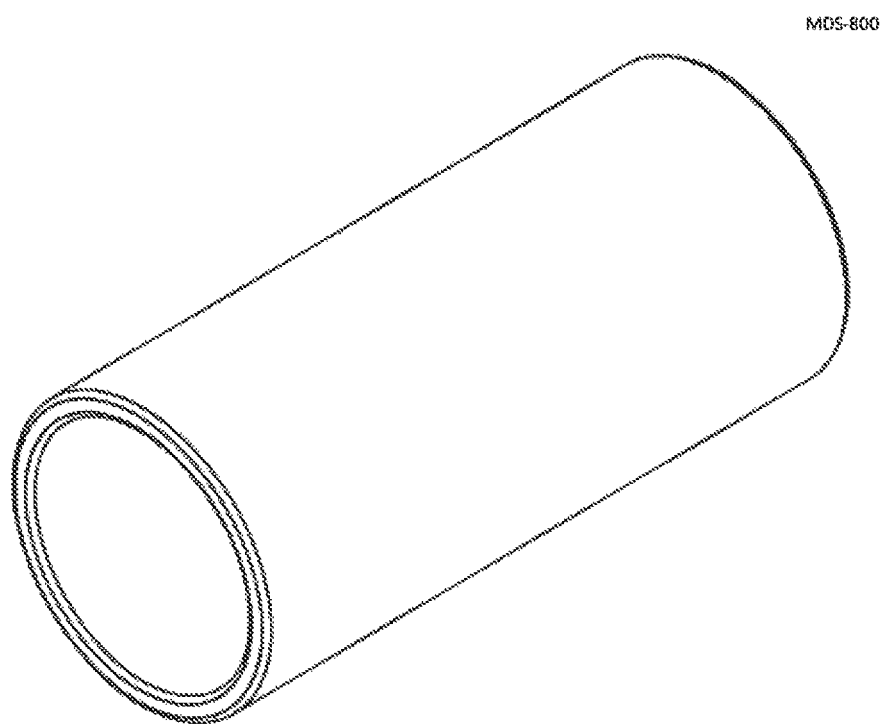
Figure 95:
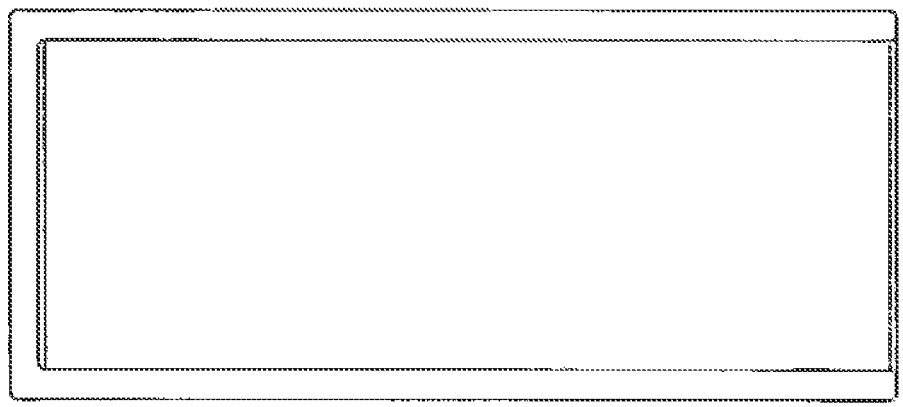
Figure 96:
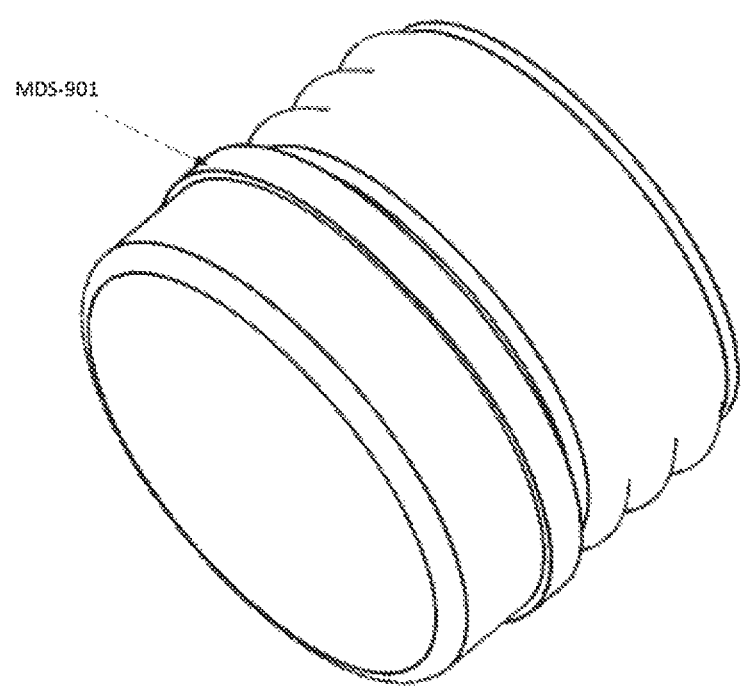
Figure 97:
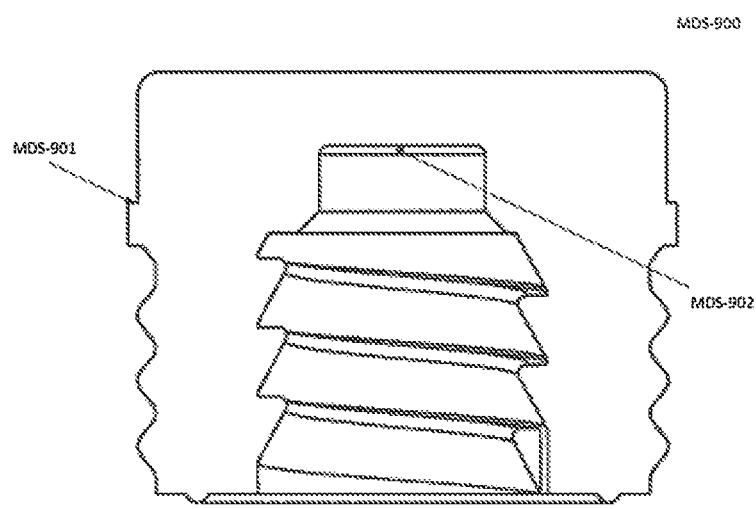

7.) After the needle barrel locking mechanism NES-500 has been disengaged by the first trigger MC-107, further compression of the housing MC-200, MC-300 into the cover MC-100, allows the second trigger MC-106 to initiate release of the medicament dispensing system (MDS) and deliver the medicament. Similar to the NES, the medicament dispensing trigger MC-106 makes contact MDS-101 with a corresponding fixture or locking mechanism MDS-100 and releases said locking mechanism MDS-100. The trigger MC-106 makes contact at an interface portion MDS-101 (see FIG. 74) when the fixture or locking mechanism MDS-100 is in a predetermined location MC-203. The fixture or locking mechanism MDS-100 maintains the stored potential energy of a biasing member MDS-700 (see FIG. 72). In one embodiment, the biasing member MDS-700 is a compression spring that is bounded by a retainer MDS-400, MDS-300 (see FIGS. 72-73) and a keeper MDS-200 (see FIGS. 72-73). The release of the fixture or locking mechanism MDS-100 allows the retainer MDS-300, MDS-400 to displace relative to the keeper MDS-200 to make contact with a plunger MDS-900 (see FIG. 72). After contacting the plunger MDS-900, the retainer MDS-300, MDS-400 and plunger MDS-900 displace together. The total displacement of the retainer MDS-300, MDS-400, and concomitantly the plunger MDS-900, is determined by the keeper MDS-200 which may provide an interference or another feature MDS-201 (see FIGS. 78-80), MDS-309 (see FIGS. 81-84), MDS-409 (see FIGS. 85-88) to restrict the retainer's MDS-300, MDS-400 movement. As such, the displacement of the retainer MDS-300, MDS-400 relative to the keeper MDS-200 can be proportional to the amount of medicament expelled from the reservoir MDS-800 (see FIGS. 94-95). Furthermore, the housing MC-200, MC-300 may have sufficient internal geometry MC-306 (see FIG. 31) to assist in the disengagement of the fixture or locking mechanism MDS-100 during injection.

Figure 89:
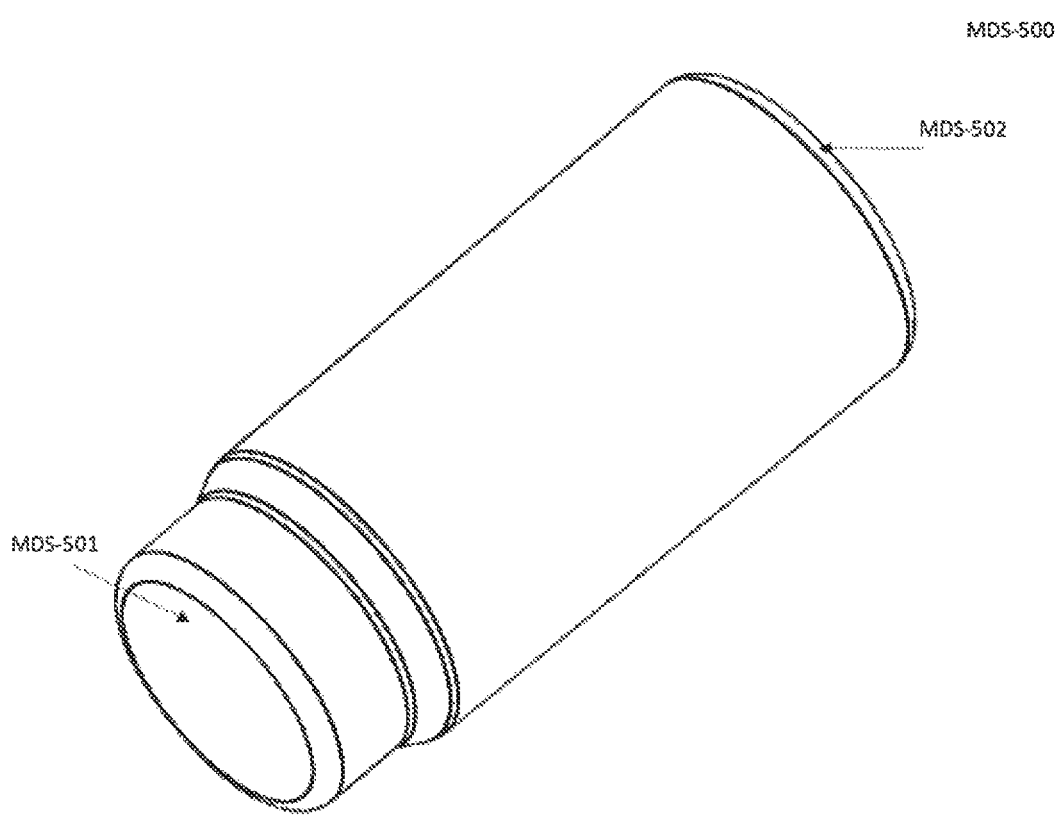
Figure 90:
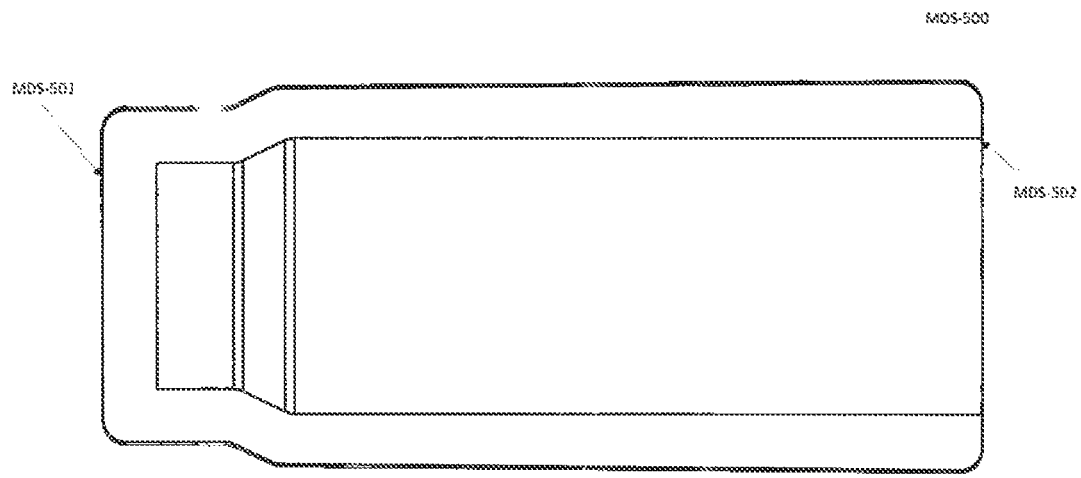
Figure 91:
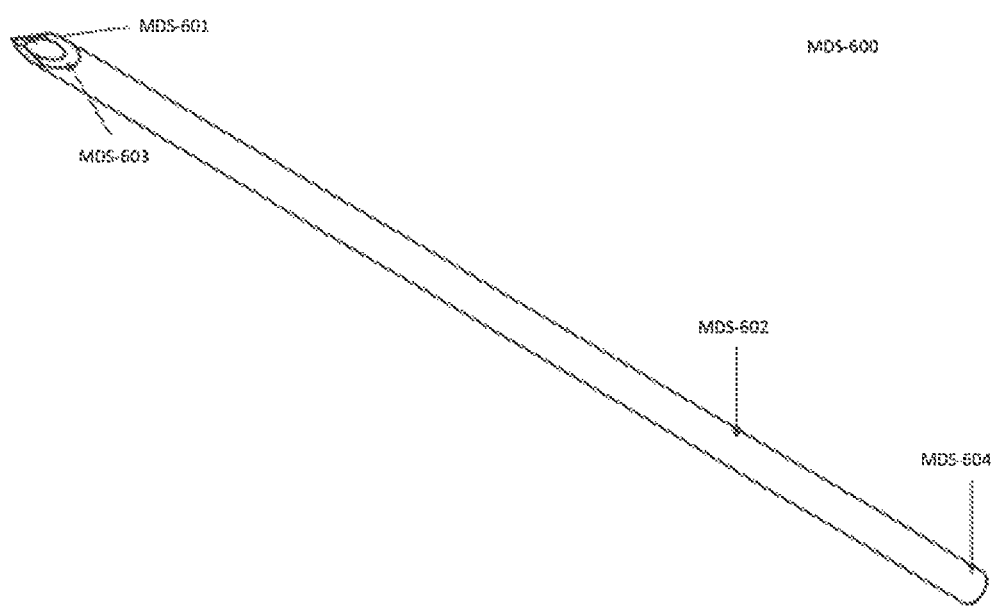
Figure 92:
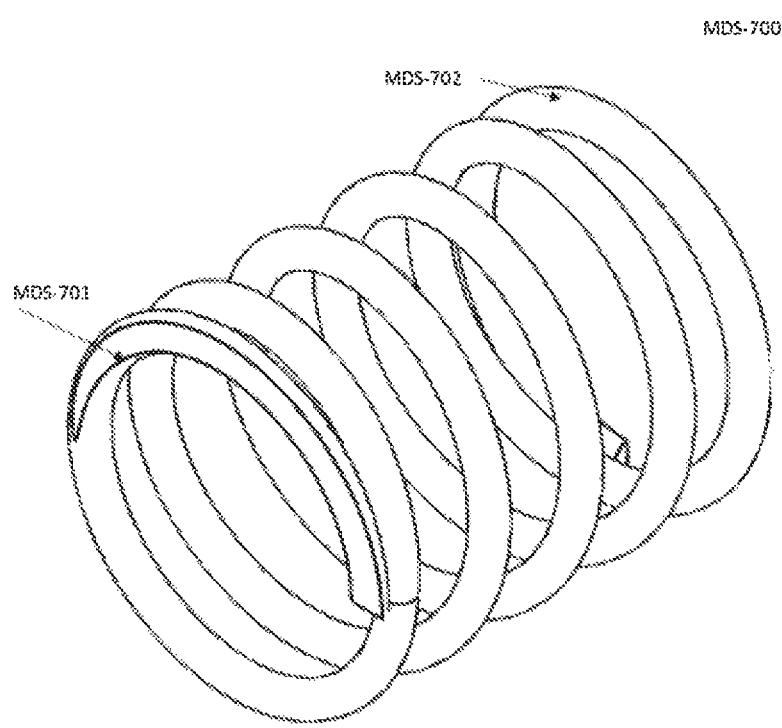
Figure 93:
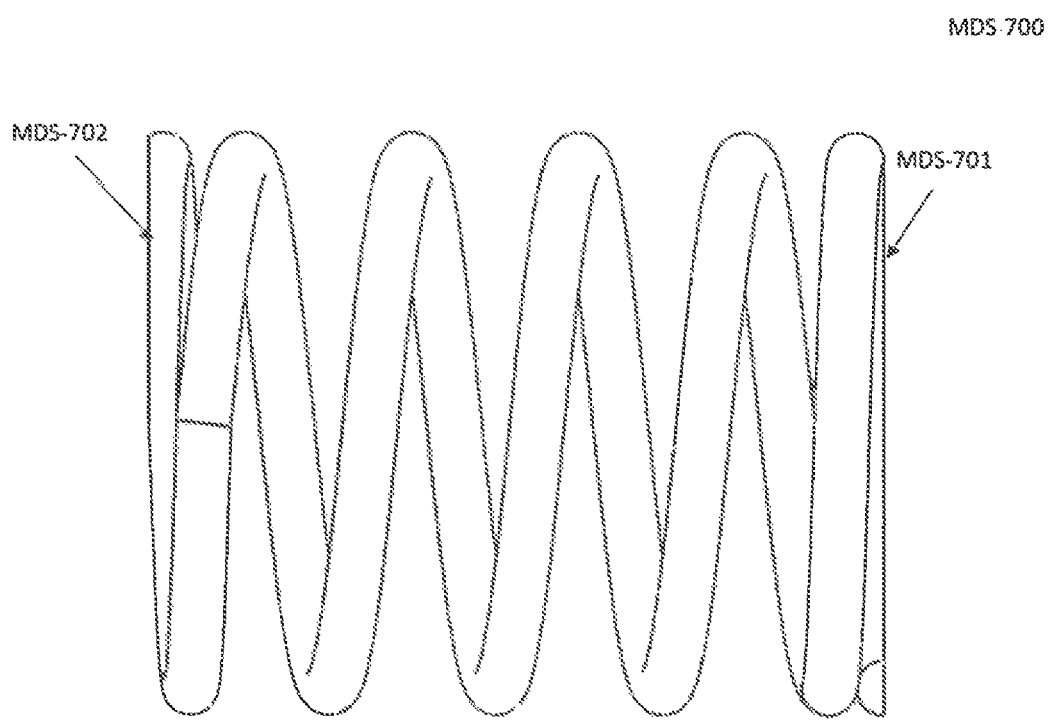

8.) Upon release of the MDS fixture or locking mechanism MDS-100 (see FIG. 74), the retainer MDS-300, MDS-400 can be displaced due to the stored potential energy of the compression spring MDS-700 and contact plunger MDS-900. A dispensing needle MDS-600 can be coupled to the retainer MDS-300, MDS-400 and in fluidic contact with the injection needle NES-700 through a flexible tubing NES-900. Furthermore, the dispensing needle MDS-600 like the injection needle NES-700 is protected with a protective barrier MDS-500 to prevent any contamination prior to injection MC-120. Therefore, the release of the compression spring MDS-700 causes the retainer MDS-300, MDS-400 to contact the plunger MDS-900, forcing the dispensing needle MDS-600 to pierce both the protective barrier MDS-500 and the plunger MDS-900. The medicament is dispensed from the reservoir MDS-800 out of the dispensing needle MDS-600 (see FIG. 91) in the opposite direction of the movement of the plunger MDS-900. In various embodiments, the retainer MDS-300, MDS-400 is composed of two halves (e.g., MDS-300, MDS-400) that are ultrasonically welded (e.g., with welds MDS-405, MDS-305 (see FIGS. 84,85)) together or by an alternative means that provides sufficient adhesion and strength. The retainer halves MDS-300, MDS-400 may secure the dispensing needle MDS-600 through a friction fit (MDS-602, MDS-302, MDS-402 (see FIGS. 82, 84, 91)). In addition, the retainer halves MDS-300, MDS-400 may secure the flexible tubing NES-900 to the dispensing needle MDS-600 through a friction or compression fitting MDS-303, MDS-304, MDS-403, MDS-404 (see FIGS. 83-85) to prevent any possible disengagement during dispensing. When fitted together, each half of the retainer MDS-300, MDS-400 may have orienting features MDS-301, MDS-401 (see FIGS. 83-85) that force the proper alignment of the two halves MDS-300, MDS-400 during assembly, which also act to maintain the dispensing needle MDS-600 and tubing NES-900 in proper alignment. To maintain a sealed reservoir MDS-800 and to not contaminate the medicament, the dispensing needle MDS-600 may only penetrate the protective barrier MDS-500 (see FIGS. 89-90) and plunger MDS-900 at the time of injection.

Figure 26:
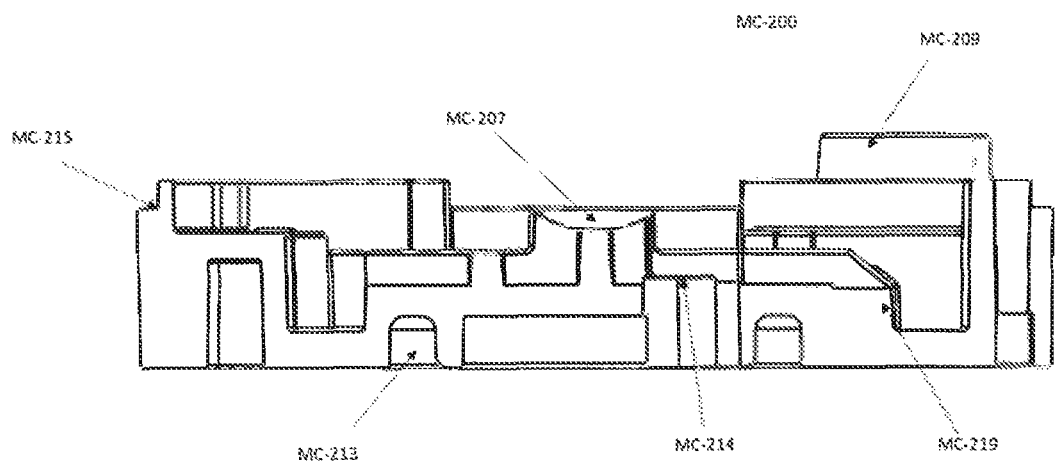
Figure 27:
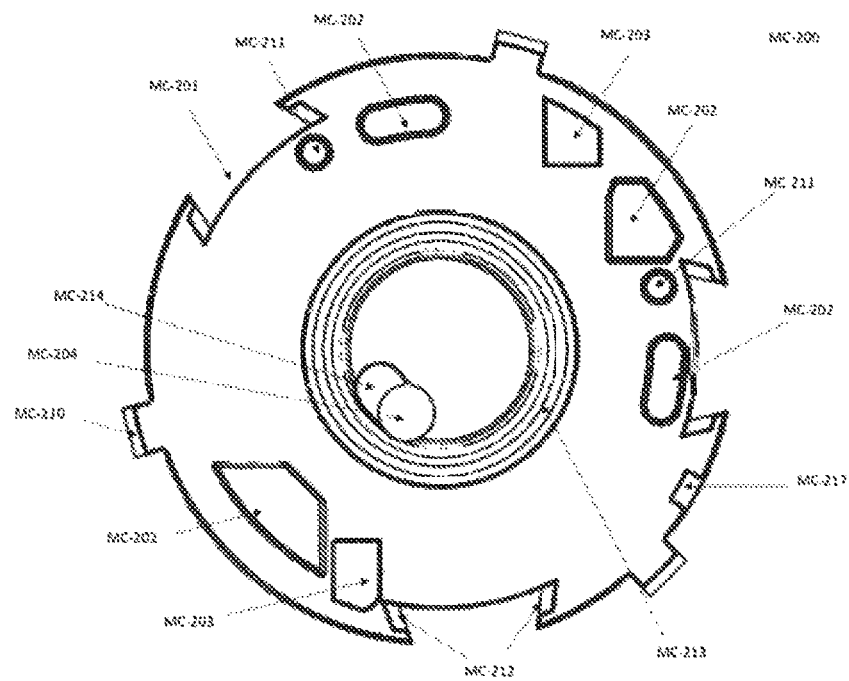
Figure 28:
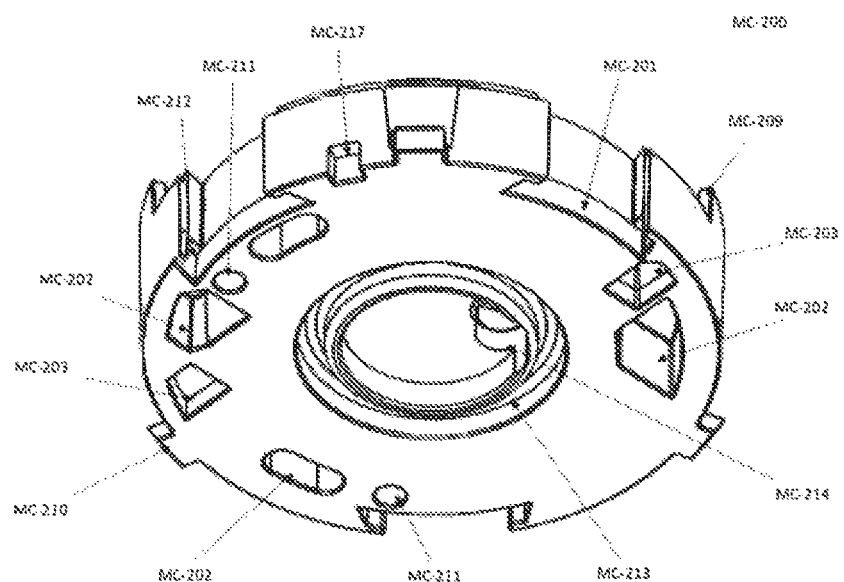

9.) Both the needle extension and drug dispensing triggers MC-106, MC-107, which activate the NES and MDS respectively, may have complimentary contoured surfaces to their respective locking mechanisms NES-501 (see FIGS. 60-62), MDS-101 (see FIG. 74) at the point of contact to reduce the force required to disengage and limit the induced stresses in the triggers MC-106, MC-107. Additionally, via the predetermined interaction location MC-203, the housings MC-200, MC-300 may provide bracing MC-219 (see FIG. 26) to limit any possible deflections in the triggers MC-106, MC-107, induced by the disengagement forces.

10.) The proximal end MDS-604 (see FIG. 91) of the dispensing needle MDS-600 may be fluidically connected to a proximal end NES-703 (see FIG. 65) of the injection needle NES-700 by a length of flexible hose or tubing NES-900. The timing of the activation of the NES and MDS can be such that the injection needle NES-700 is embedded into tissue and the drug is dispensed within a designated, or predetermined time frame.

11.) After the injection, and the release of pressure on the sealed housing MC-200, MC-300 by the user, the sealed housing MC-200, MC-300 may automatically translate relative to the cover MC-100 due to the biasing member SS-300. In some embodiments, the biasing member is a compression spring SS-300. During the subsequent expansion of the sealed housing MC-200, MC-300 the interlocks SS-100 are removed from their cavities MC-201, MC-314 and restrict any relative motion between the sealed housing MC-200, MC-300 and cover MC-100. The interlocks SS-100 prevent the auto-injector 1 from being collapsed, thereby preventing subsequent extension of the distal end NES-701 of the injection needle NES-700 from the cover MC-100. The expansion of the sealed housing MC-200, MC-300 relative to cover MC-100 can be sufficient to fully withdraw and conceal the injection needle NES-700 in the auto-injector 1. Additionally, the channels, slots, detents, etc. MC-103 in the cover MC-100 and the molded or formed tabs or protrusions MC-210 on the sealed housing MC-200, MC-300 may prevent any rotation of either the cover MC-100 or the sealed housing MC-200, MC-300 relative to one another. The interlocks SS-100 which prevent subsequent collapse of the auto-injector 1 and the inability to rotate the cover MC-100 or housing MC-200, MC-300 allow for a safe means of disposal, preventing accidental needle exposure NES-700.

The following paragraphs describe another embodiment of the auto-injector 1, including alternate or complimentary configurations and activation sequences of the auto-injector 1.

In this embodiment, the auto-injector 1 may have an internal power source to allow certain functionalities of the auto-injector 1 during storage, during injection, and post injection. The auto-injector 1 may provide audible instructions for performing an injection. Additionally, connectivity of the auto-injector 1 to everyday smart devices allows for additional functionality. The connected smart device may display visual and/or auditory instructions for performing an injection. Certain embodiments may allow for the user to monitor the temperature, and location of the auto-injector 1. Additionally, the connected device may allow the user to see if other auto-injectors 1 are nearby. Additional embodiments may allow the smart device to contact emergency responders or next of kin once an injection has been initiated. Furthermore, information about the auto-injector 1 may be monitored remotely by the manufacturer.

Figure 115:
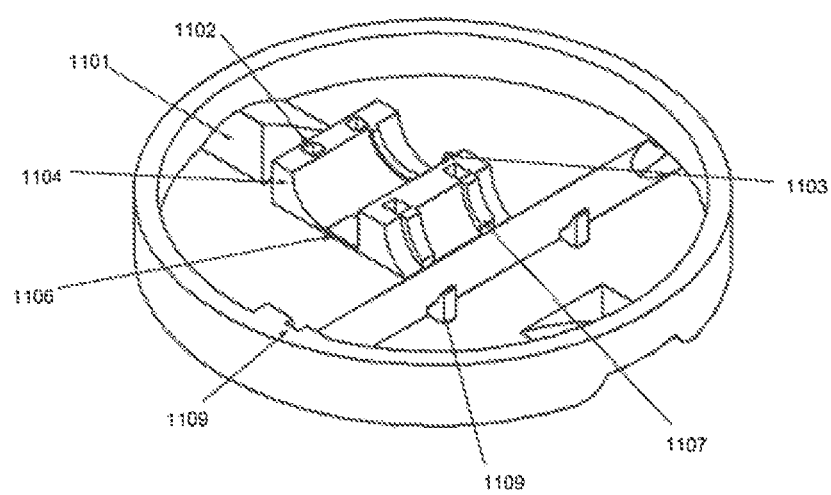

Similar to the embodiment described above, this embodiments can establish an orientation of the auto-injector 1 prior to performing any injection, through proper human factor engineering principles. The auto-injector 1 may present the user with an intuitive interface, leveraging existing mental models from everyday applications. In regard to the user interface, additional or alternative embodiments will provide the same benefits with possible variations of the following aspects: geometry or element 1101 (see FIG. 115), tactile surfaces, indicia, labeling, and/or coloring, that may aid the user in establishing an orientation prior to performing an injection.

Figure 110:
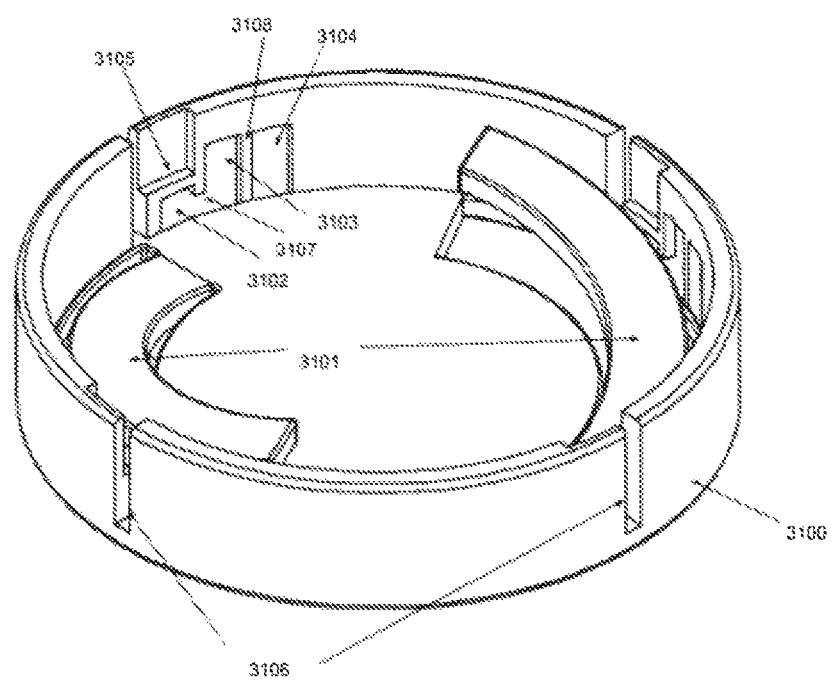
Figure 111:
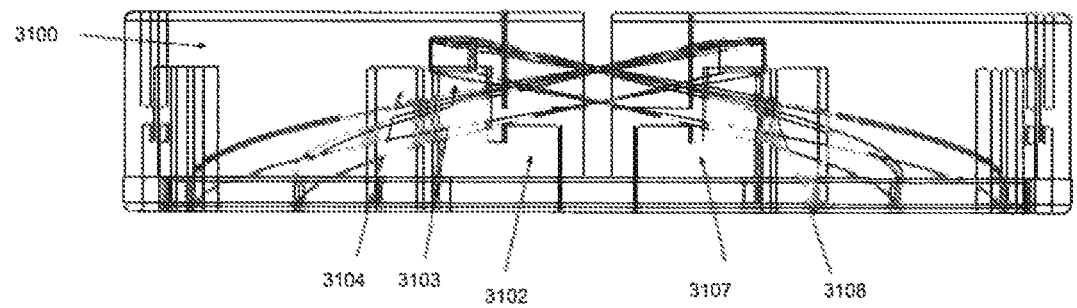
Figure 122:
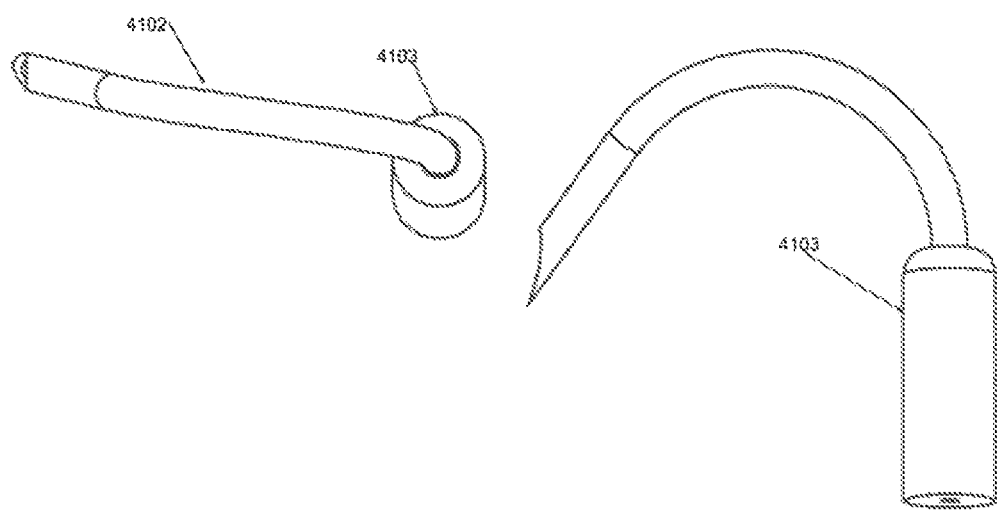
Figure 123:
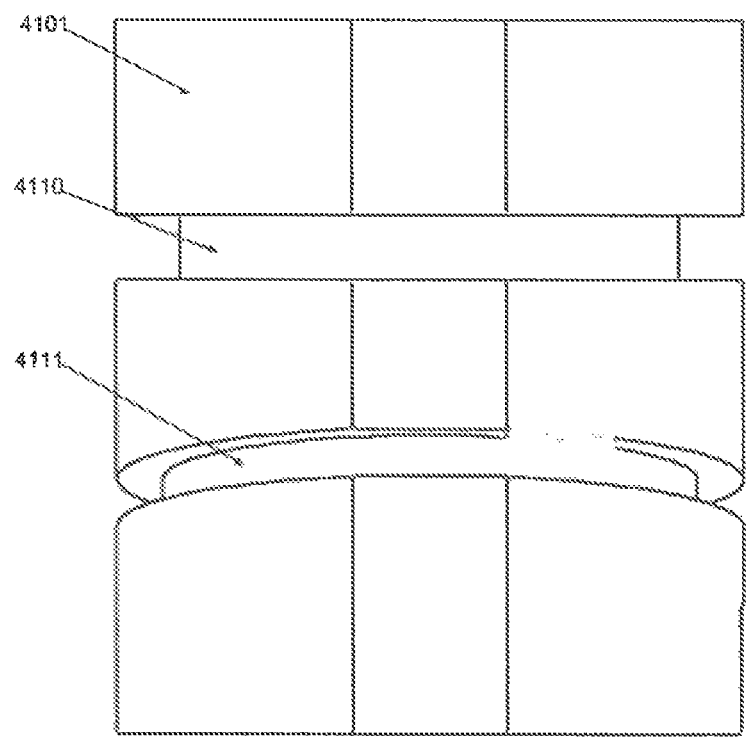
Figure 124:
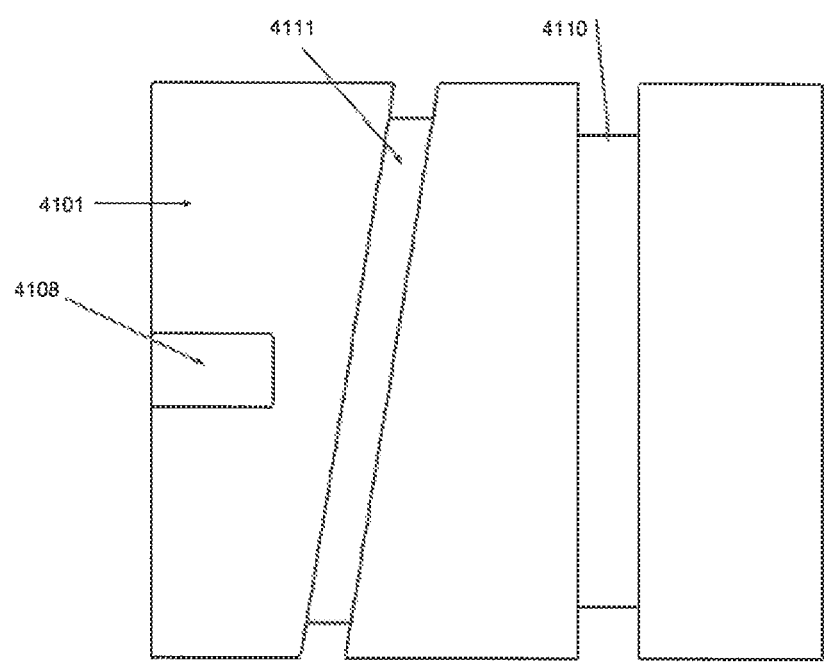
Figure 125:
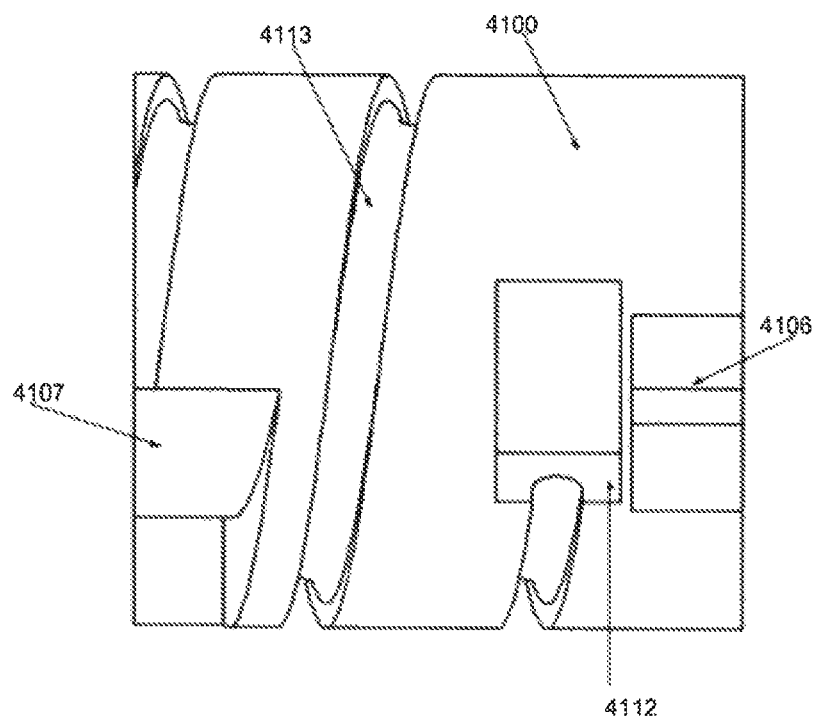
Figure 126:
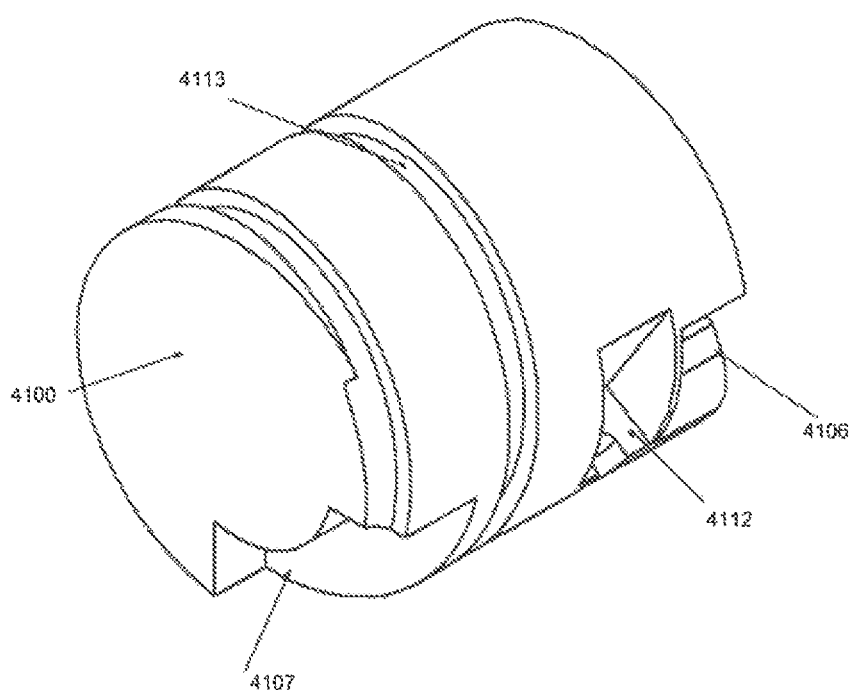
Figure 127:
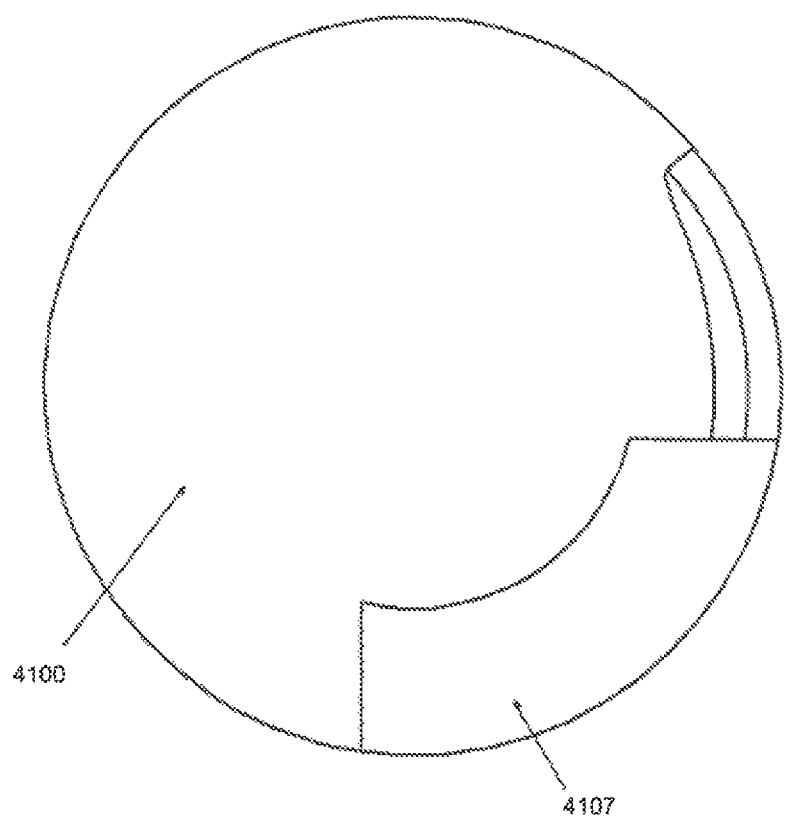
Figure 128:
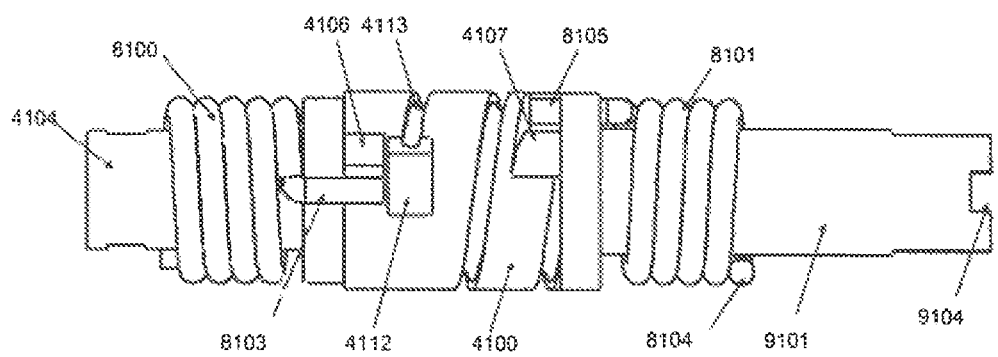
Figure 129:
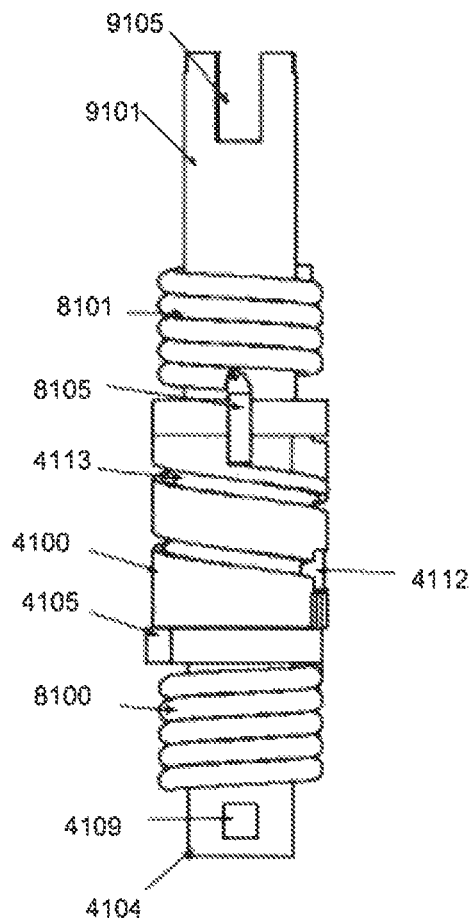
Figure 130:
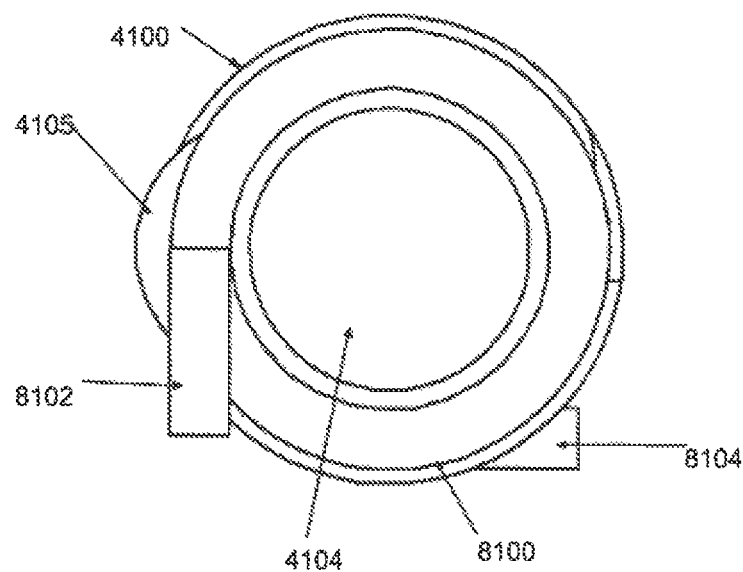

In certain embodiments, the auto-injector 1 includes a safety mechanism SS-200 to be removed before any subsequent operations. The injection surface MC-121 may be exposed to the user once the safety mechanism SS-200 has been removed, further aiding in establishing the proper orientation. The safety mechanism SS-200 may also provide a means of preventing the auto-injector 1 from moving from a locked position 3102 (see FIGS. 110-111) to an unlocked position 3103, 3104 (see FIGS. 110-111) prior to removal, such that the injection sequence may not commence without first removing the safety mechanism SS-200. Alternatively, or additionally, the safety mechanism SS-200 may protect the user from an injection needle 4102 (see FIG. 122) if an accidental discharge were to happen, or remove a protective shroud or sheath NES-100 that can facilitate similar functionality. Therefore, the removal of the safety mechanism SS-200 may provide or facilitate the following functionalities, for example: establish orientation of the auto-injector 1, provide an interlock SS-204 to prevent rotation of the sealed housing prior to removal, protect the user from the injection needle 4102, remove a conjoined or coupled component NES-100 that further protects the injection needle 4102 or a user from the injection needle 4102, and protect a tactile coating or surface on the injection contact surface MC-121 of a cover 3100 (see FIGS. 110-111).

Figure 105:
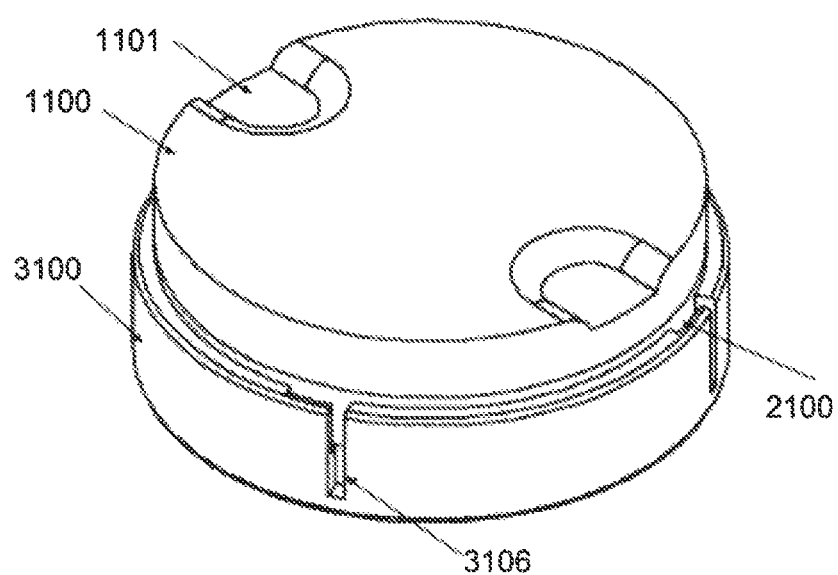
Figure 106:
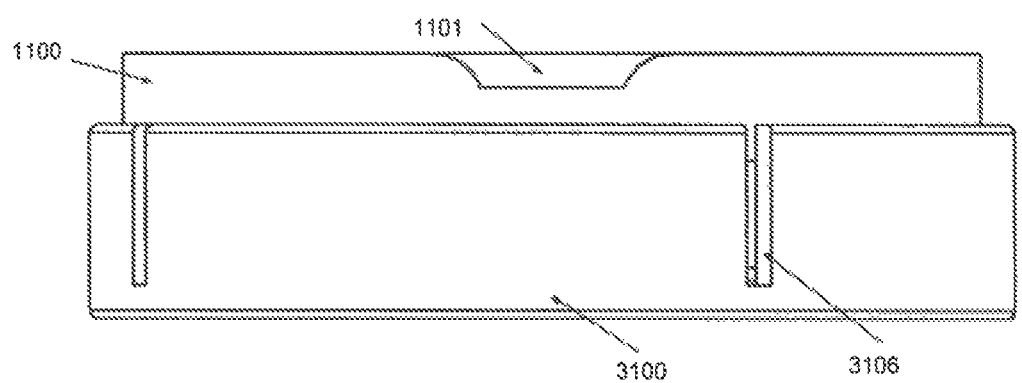
Figure 107:
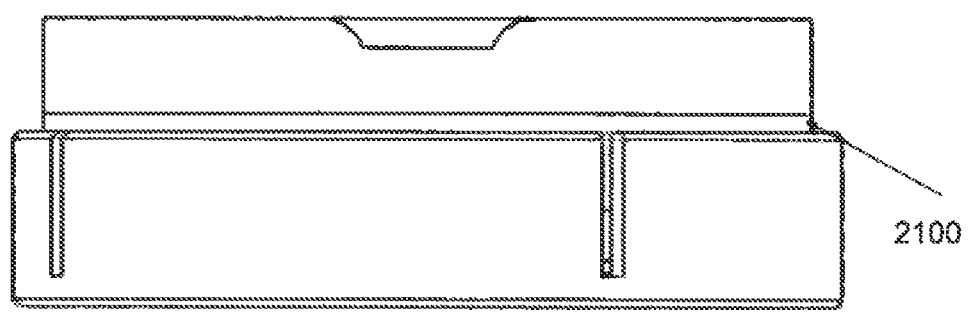
Figure 108:
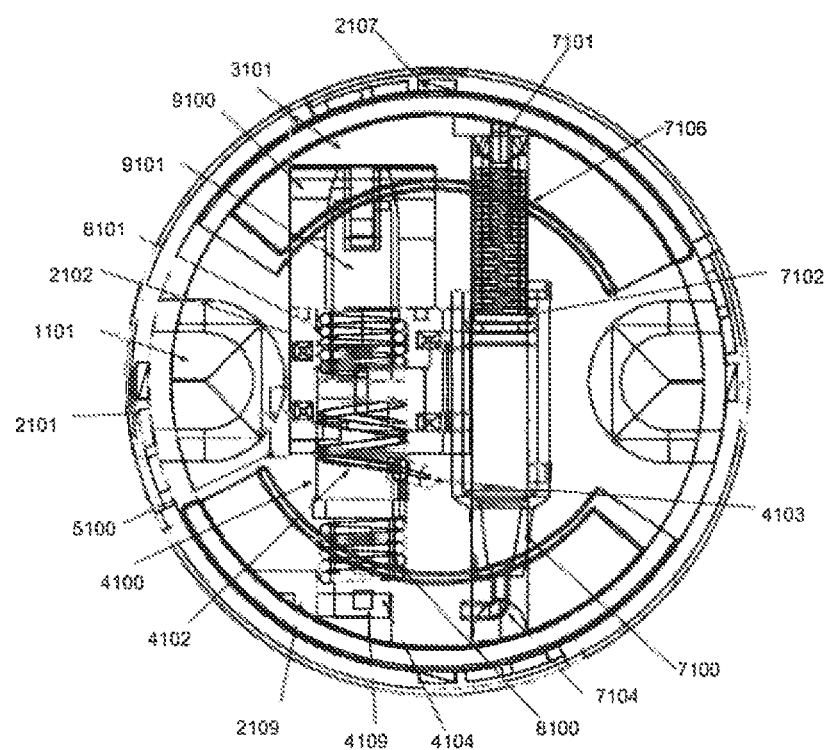
Figure 109:
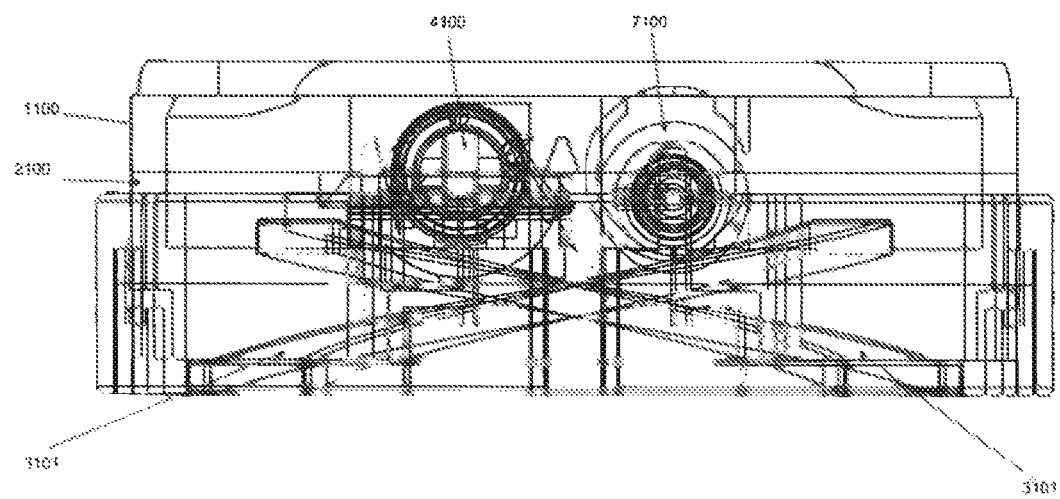
Figure 112:
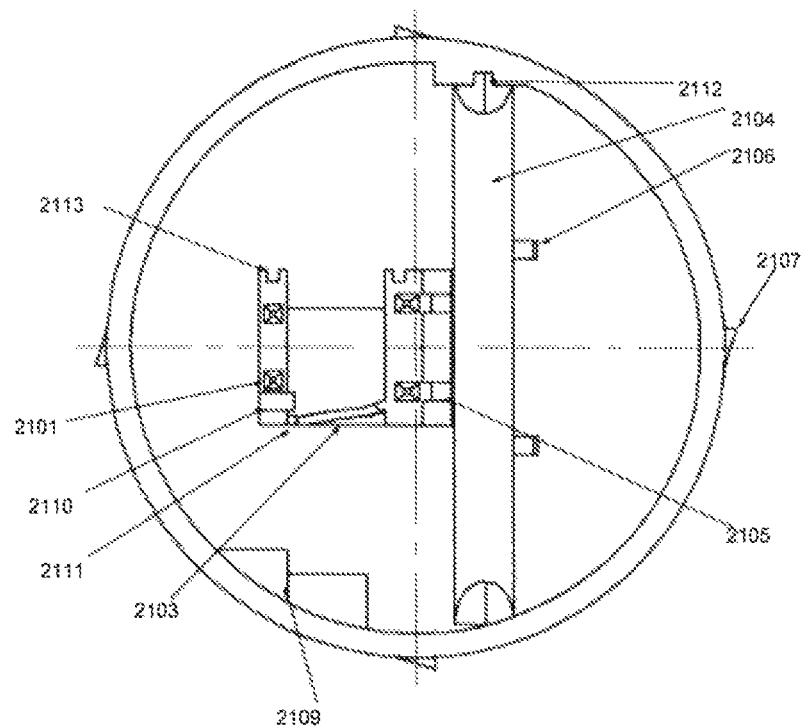
Figure 113:
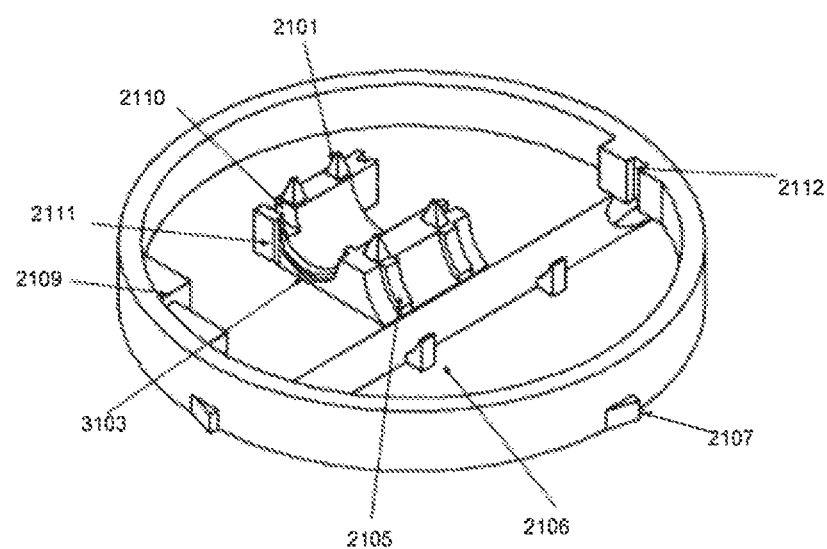

In addition to the internal components discussed below, the auto-injector 1 can include two main parts, a sealed housing 1100, 2100 (see FIGS. 105-107) rotatably retained in the cup-shaped cover 3100 that may also form the bottom side or injection contact surface MC-121. The sealed housing can be made from upper half 1100 and lower half 2100 bonded together through the means of ultrasonic welding or alternative means that provide sufficient adhesion and joint strength. In some embodiments the bond between the upper half 1100 and the lower half 2100 may form a hermetic seal. In some cases, the housing 1100, 2100 or one of the subsequent halves 1100, 2100 that compose the housing 1100, 2100 contain molded or formed protrusions 2107 (see FIGS. 112-113) that guide and constrain the housing 1100, 2100 during operation within the cover 3100. The sealed housing 1100, 2100 can function as the primary interface for the user performing the injection. In addition to the housing 1100, 2100 being possibly hermetically sealed, the sealed housing 1100, 2100 may contain additional sealing components MC-215 (see FIG. 26), MC-315 (see FIGS. 31-32) or compounds to completely enclose the internal chamber of the housing. This sealed chamber may perform the following functionalities, for example: provide and maintain internal desired cleanliness criteria, provide a water-resistant enclosure, and allow for a pressure differential between the internal and external environments. Some embodiments of the auto-injector 1 may preserve the desired internal conditions until the time of injection. The two halves 1100, 2100 that form the sealed housing, can have a geometry and/or components (e.g., 1102, 1103, 1104, 1105, 1106, 1107, 1108, 1109, 2101, 2102, 2103, 2104, 2105, 2106, 2108, 2109, 2110, 2112, 2113) that may locate and secure the internal components.

The following list of items (1-14) describes another example activation sequence of internal components and mechanisms of the auto-injector 1 and the individual component interactions, according to various embodiments.

Figure 116:
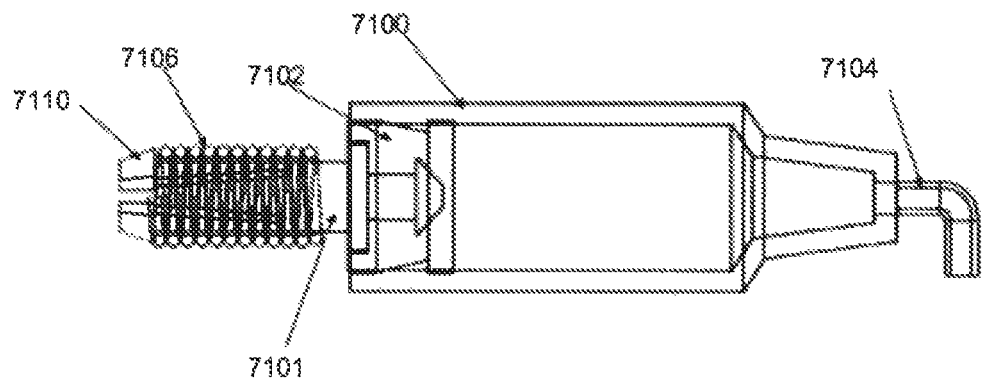
Figure 117:
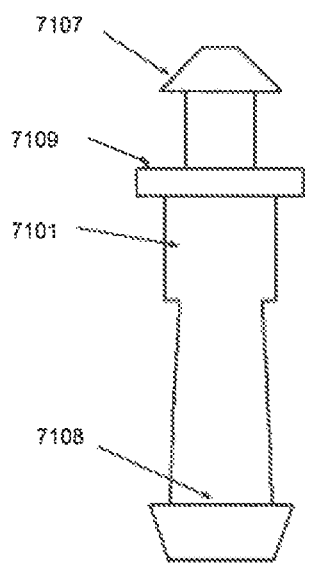
Figure 118:
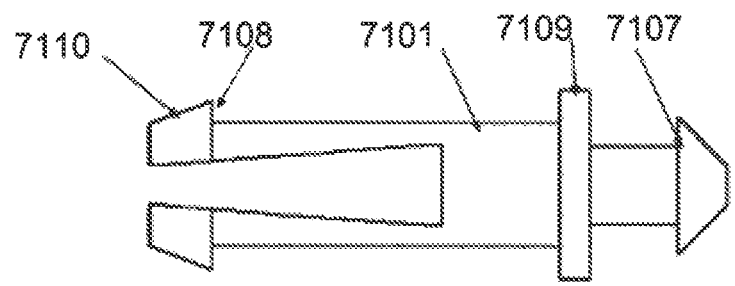
Figure 119:
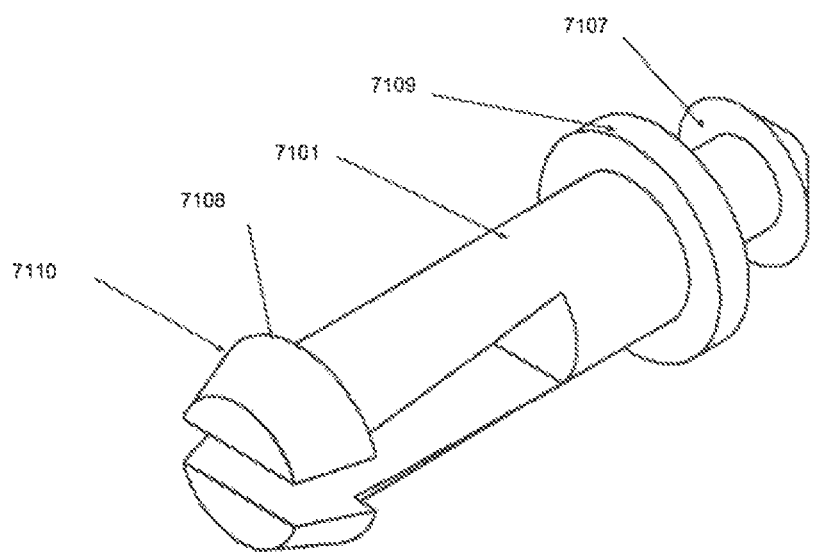
Figure 120:
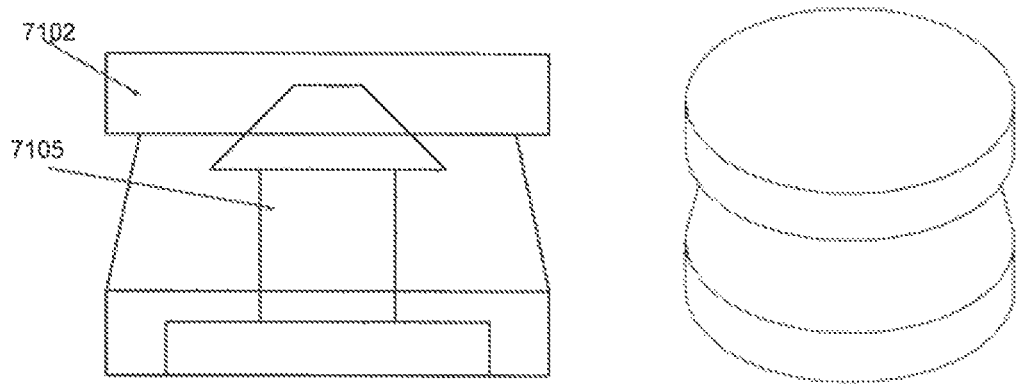
Figure 121:
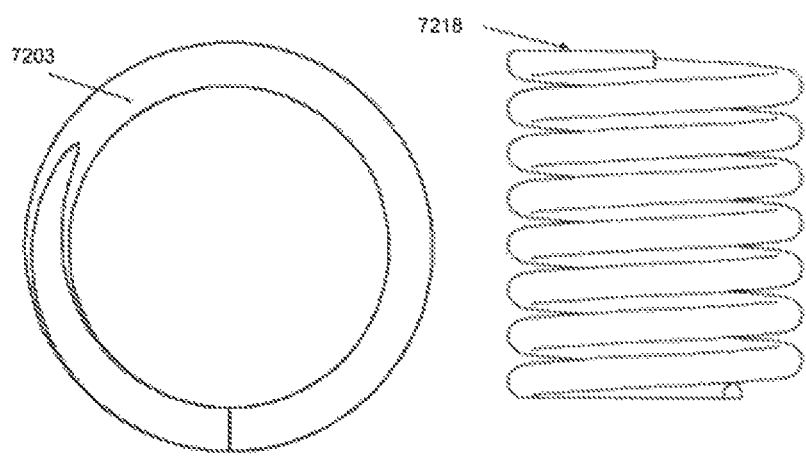
Figure 136:
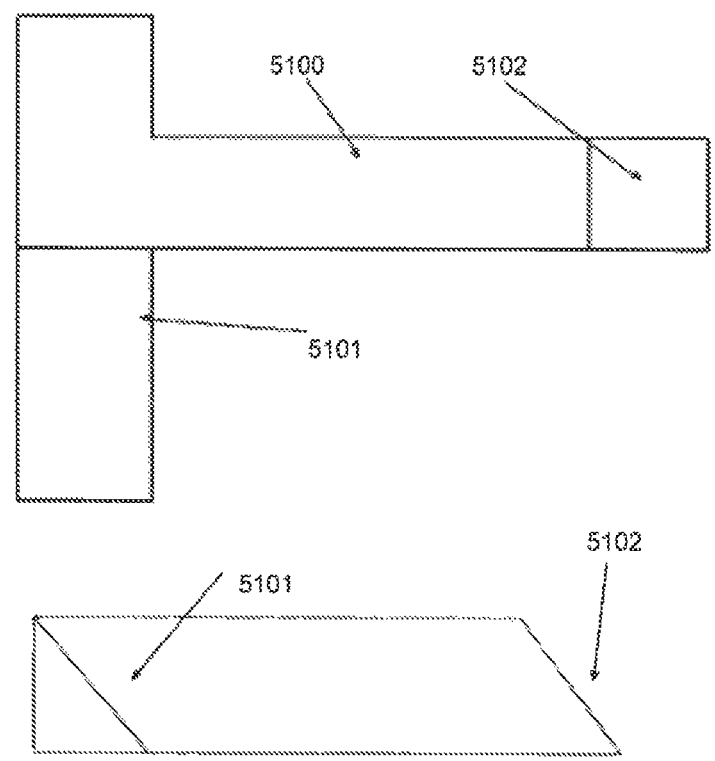

1.) When the user unlocks the housing 1100, 2100 from the cover 3100, the housing 1100, 2100 automatically moves to an armed position 3103 (see FIGS. 110-111). The housing 1100, 2100 translates and rotates a certain constrained distance and degree. The mechanisms that activate the internal activation sequences inside the sealed housing are triggers or protrusions MC-106, MC-107 which are molded or formed on a surface of the cover 3100. Cavities MC-202, MC-211 are molded or formed into the lower half 2100 of the sealed housing 1100, 2100 to allow the sealed housing and the cover 2100 to rotate and translate relative to one another without interfering with or damaging the activation or alignment mechanisms. During the assembly (see position 3105), activation (see positions 3102, 3103), and injection (see position 3104), the protrusions or tabs 2107, molded or formed on the sealed housing 1100, 2100 and corresponding channels, slots, detents, etc. 3106, 3108, 3107 (see FIG. 110) on the cover 3100, interface to provide sufficient clearance and alignment to prevent damage of the protrusions or triggers MC-106, MC-107 on the cover 3100. Furthermore, the cover 3100 can have alignment posts or protrusions MC-105, that interface with corresponding cavities MC-211 in the sealed housing 1100, 2100 at the time of injection such that they may aid in the alignment of the sealed housing 1100, 2100 and cover 3100 to orient the triggers MC-106, MC-107 on the cover 3100 with the corresponding locking mechanisms 5100 (see FIG. 136), 7110 (see FIG. 116) disposed in the sealed housing 1100, 2100. Additionally, the cover 3100 and/or sealed housing 1100, 2100 may contain additional features that aid in maintaining alignment between the sealed housing 1100, 2100 and the cover 3100 during relative movement. The automatic expansion may occur due to a spring 3101 (see FIGS. 108-111) disposed or formed therein, to bias the housing 1100, 2100 away from the cover 3100 during activation, to facilitate use. In certain embodiments the housing 1100, 2100 can be returned to the locked position 3102 and maintain the internal sealed nature of the sealed housing. To return to the locked position 3103, 3104, the user compresses the housing 1100, 2100 into the cover 3100 and rotates the housing 1100, 2100 in the opposite direction.

2.) In certain embodiments the internal injection needle 4102 is not aligned with the needle aperture MC-112 formed in the bottom side of the cover 3100. Therefore, if the injection needle 4102 were to inadvertently misfire, the sharp distal end of the needle NES-701 would not penetrate through the bottom side of the cover MC-121. The user may verify the positioning of the housing 1100, 2100 relative to the cover 3100 by means of indicia and labeling present on the auto-injector 1.

3.) Once the auto-injector 1 is in the unlocked position MC-118 and has transitioned to the activated position 3103, 3104, the housing 1100, 2100 can rotate freely without interference with the triggers MC-106, MC-107. Preceding the manual compression of the auto-injector 1 to facilitate an injection, the housing 1100, 2100 can be reset or returned to the locked position 3102, if accidental movement to the activated position 3103 has taken place.

4.) When the housing 1100, 2100 is compressed into the cover 3100, transitioning from the armed position 3104 to the injection position MC-120, the triggers or protrusions MC-106, MC-107 on the cover 3100 pierce the designated locations MC-203 on the housing 2100, making contact with the corresponding locks 5100, 7110, and starting the injection sequence. To allow the triggers MC-106, MC-107 to penetrate through the bottom side of the lower housing half 2100 without causing any loose breakage or compromising the structure of the triggers MC-106, MC-107. Therefore, the areas MC-203 where the triggers MC-106, MC-107 penetrate may contain perforations or other aids MC-219 (e.g., different material, etc.).

5.) When the user compresses the auto-injector 1 to perform the injection, the first trigger MC-107 pierces the lower housing half 2100 and initiates the uncoiling of the curved injection needle 4102. The uncoiling is initiated by the first trigger MC-107 disengaging the locking mechanism 5100. The first trigger MC-107 pierces the housing and contacts the uncoiling locking mechanism 5100. The uncoiling locking mechanism 5100 is disengaged by being retracted from the needle barrel 4100 (see FIGS. 125-130) where it sits during the stored, active, and armed positions 3102, 3103, 3104. The housing 1100, 2100 may have sufficient internal geometry (see elements MC-306, MC-307 (see FIG. 31)) to assist in the disengagement of the locking mechanisms 5100, 7110 during the time of injection. Prior to engagement with the first trigger MC-307, the uncoiling of the injection needle 4102 may be prevented by the uncoiling locking mechanism 5100, inhibiting the needle barrel 4100 from rotating. Therefore, the corresponding torsion spring 8100 remains wound and under load. In this embodiment, a portion of the injection needle 4102 has a helical shape prior to injection and a straightened out shape at the time of injection. The helical shape of the injection needle 4102 allows the auto-injector 1 to maintain a low profile and high aspect ratio. Additionally, the needle 4102 can be of such material that it will not be compromised during manufacturing or uncoiling during injection.

Figure 114:
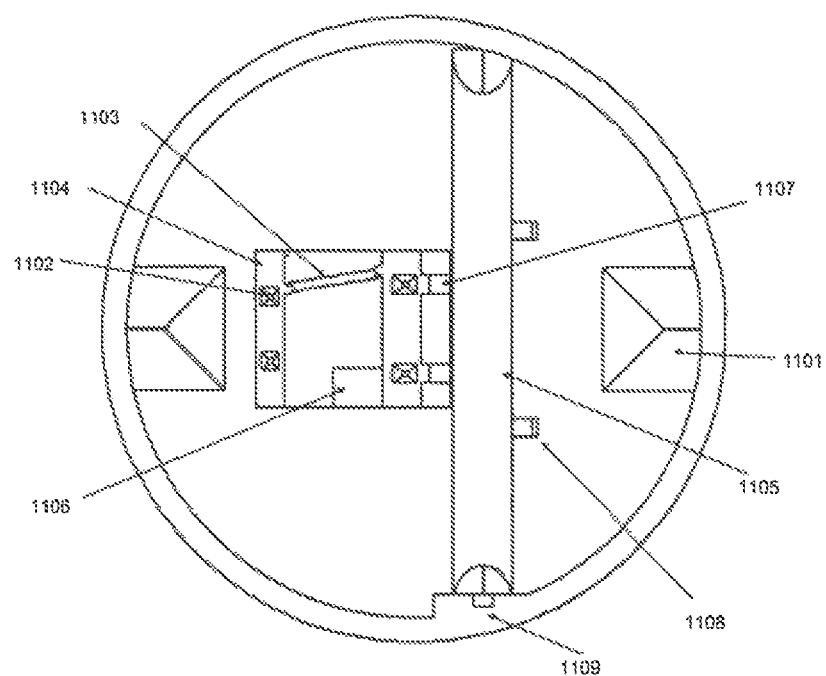

6.) Once the locking mechanism 5100 is disengaged from the needle barrel 4100, the torsion spring 8100 is free to rotate the needle barrel 4100 a set angle. The injection needle 4102 can be fixed to a retainer 4103 (see FIG. 122) that mates with a corresponding recess 4112 (see FIGS. 125-126) formed in the needle barrel 4100. When the needle barrel 4100 rotates, a portion of the helical injection needle 4102 is uncoiled. In this embodiment, a portion of the needle 4102 that was curved before injection, can be straightened and embedded in tissue during the injection. A pair of opposing ribs 2102 (see FIG. 108), 1104 (see FIGS. 114-115) molded in the upper half 1100 and the lower half 2100 of the housing keep the needle barrel 4100 in place and properly aligned during rotation while both uncoiling and recoiling. In addition, the ribs or housing 4113 (see FIGS. 125-126), 1104, 2102 that aligns and guides the needle barrel 4100 may be formed or have such geometry (see elements 1103 (see FIGS. 114-115), 2103 (see FIG. 112)) that guides and allows the injection needle 4102 to disengage from the needle barrel 4100.

7.) The distal end NES-701 of the helical injection needle 4102 passes through an aperture 2111 (see FIGS. 112-113) of similar size to the injection needle 4102 formed in the lower housing half 2100, so that the injection needle 4102 is straightened during uncoiling by the aperture 2111. Controlling the needle barrel's 4100 rotation by an interference element 4107 (see FIGS. 125-127) ensures the barrel 4100 is rotated the desired predetermined number of degrees, ensuring that the distal end NES-701 of the needle 4102 is stopped at the desired injection depth.

8.) In addition, when the distal end NES-701 of the needle 4102 exits the lower housing half 2100, it may pass through and pierce a seal covering the aperture 2111. The seal acts as the barrier between the internals of the housing 1100, 2100 and the outside environment. This seal may by an adhesively adhered thin TPE membrane (e.g., Santoprene® material) that keeps the housing 1100, 2100 hermetically sealed. In addition, this type of seal allows the distal end NES-701 of the needle 4102 to pass through, without removing any material, avoiding a corking effect and partial or complete blocking of the internal lumen or bore of the needle 4102 during injection. The seal may also ensure that the sterile internal environment of the housing is maintained.

Figure 137:
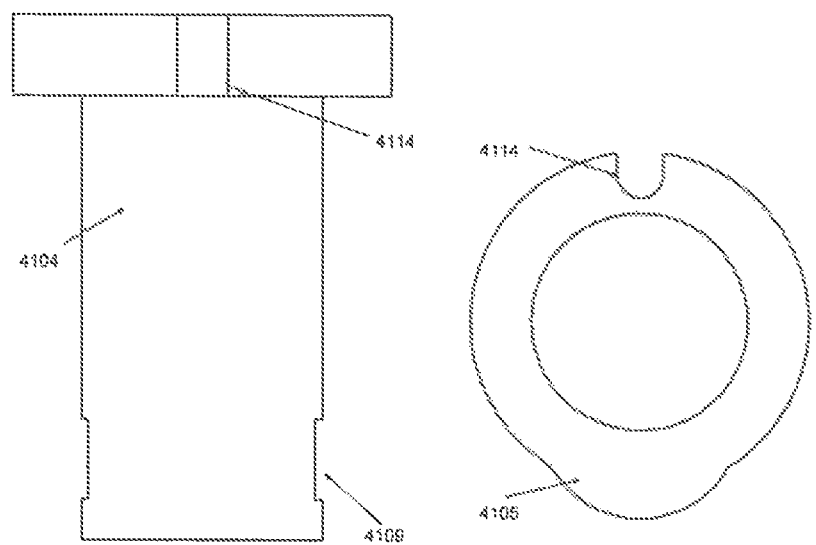
Figure 138:
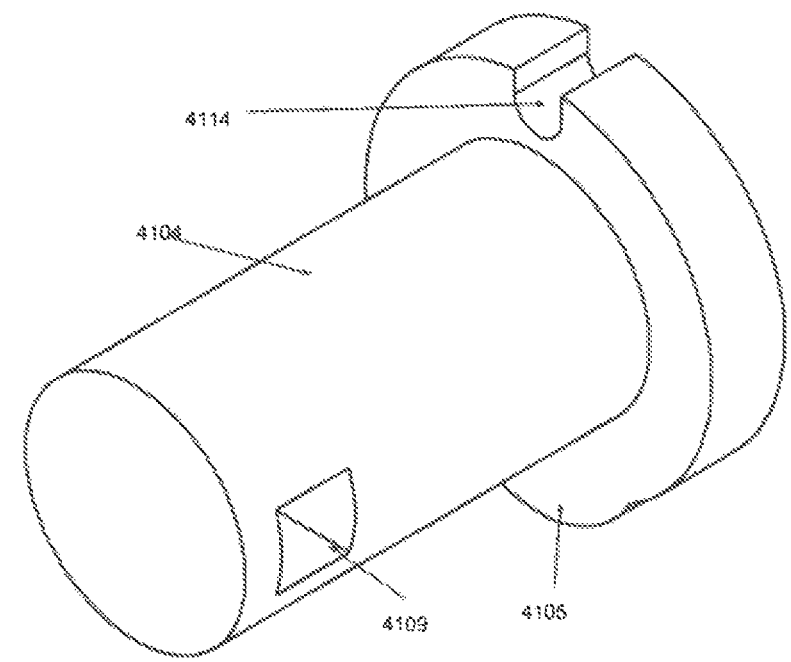
Figure 139:
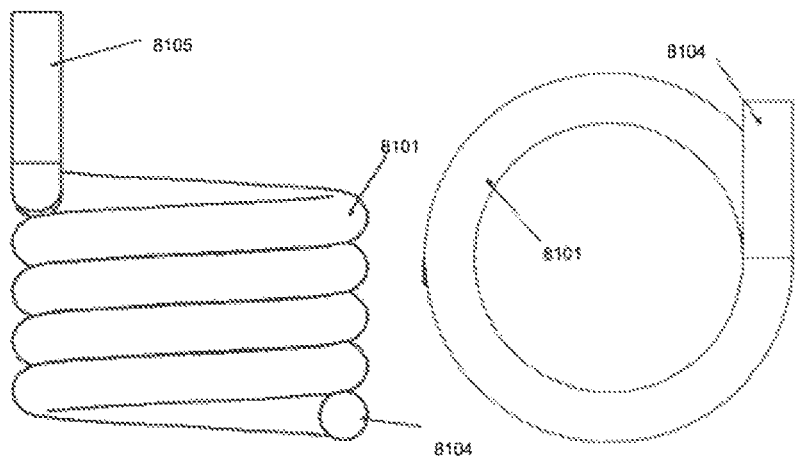
Figure 140:
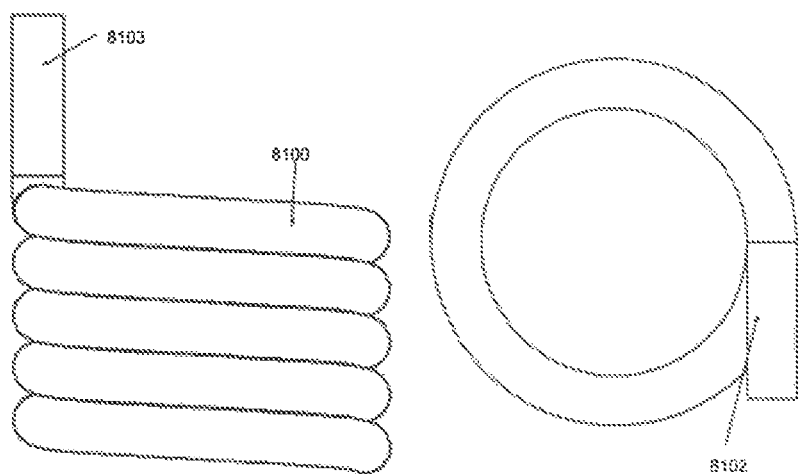

9.) Once the needle barrel 4100 uncoiling rotation is complete, the torsion spring 8100 can disengage from the needle barrel 4100. The torsion spring 8100 can disengage from the needle barrel 4100 because an uncoiling spring tensioner 4104 (see FIG. 128) which is in contact with both the needle barrel 4100 and the torsion spring 8100 includes a torsion spring contact point 4106 (see FIG. 128) and collared surface 4105 (see FIGS. 129-130) that has a non-circular shape. In one embodiment, the torsion spring contact surface 4114 (see FIGS. 137-138) causes an axial deflection of the torsion spring 8100, due to the non-circular collar 4105, allowing the proximal end 8103 (see FIG. 140) of the torsion spring 8100 to raise up and out of contact point 4106 on the barrel 4100 and disengage from the needle barrel 4100. Disengagement can occur, so that the recoil torsion spring 8101 that performs the recoiling of the injection needle 4102 onto the barrel 4100 does not have to rewind the uncoiling torsion spring 8100.

10.) After the needle barrel locking mechanism 5100 has been disengaged by the first trigger MC-107, further compression of the housing 1100, 2100 into the cover 3100 allows the second trigger MC-106 to initiate dispensing of the medicament. A plunger 7102 associated with a reservoir or vial 7100 containing the medicament is propelled or driven forward by a compression spring 7106, which in turn dispenses the medicament. The compression spring 7106 is actuated when the second trigger MC-106 released a retainer 7101 that bounds and retains the spring 7106 in a stored position. The compression spring 7106 drives the retainer 7101 and in turn the plunger 7102 into the vial 7100, to force the medicament out of the vial 7100, through the dispensing port 7104.

11.) The proximal end NES-703 of the injection needle 4102 is fluidically connected to the dispensing port 7104 by a length of flexible hose or tubing NES-900. The timing of the uncoiling NES and medicament administration MDS is such that the injection NES and medicament MDS delivery occur within a short designated time window (e.g., a few seconds after compression).

Figure 133:
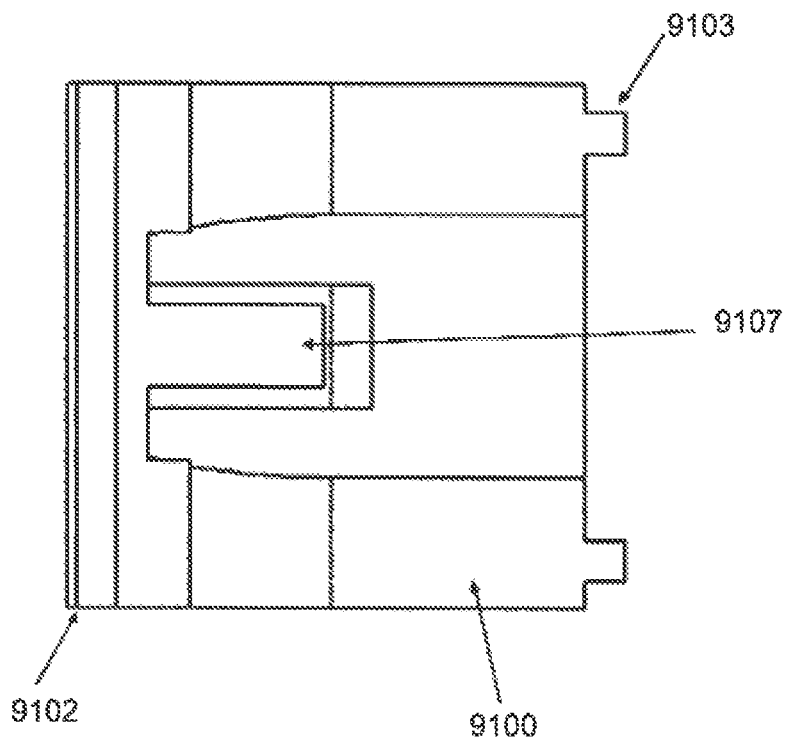
Figure 134:
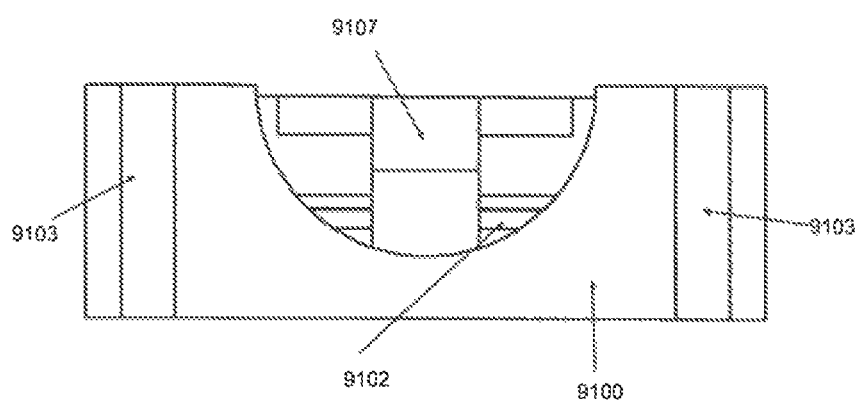
Figure 135:
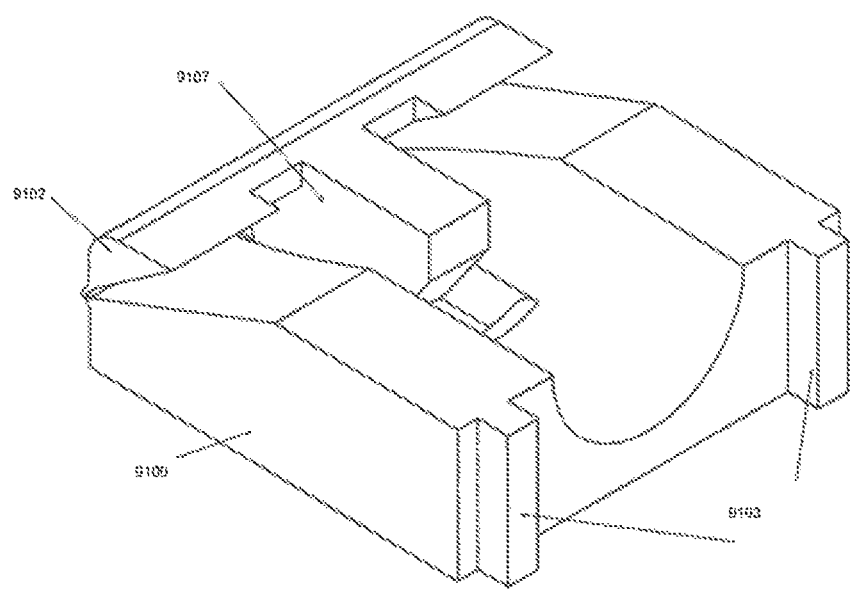

12.) Once the auto-injector 1 has been compressed against the injection location and the injection has commenced, the individual holds the auto-injector 1 against the injection location for a designated time duration. Upon release of the pressure on the auto-injector 1, after the designated time duration, recoiling of the injection needle 4102 commences. Due to the biasing member 3101, the housing 1100, 2100 automatically expands and upon expansion releases a third locking 9100 (see FIGS. 133-134) mechanism which in turn activates the recoiling torsion spring 8101 (see FIG. 129).

Figure 131:
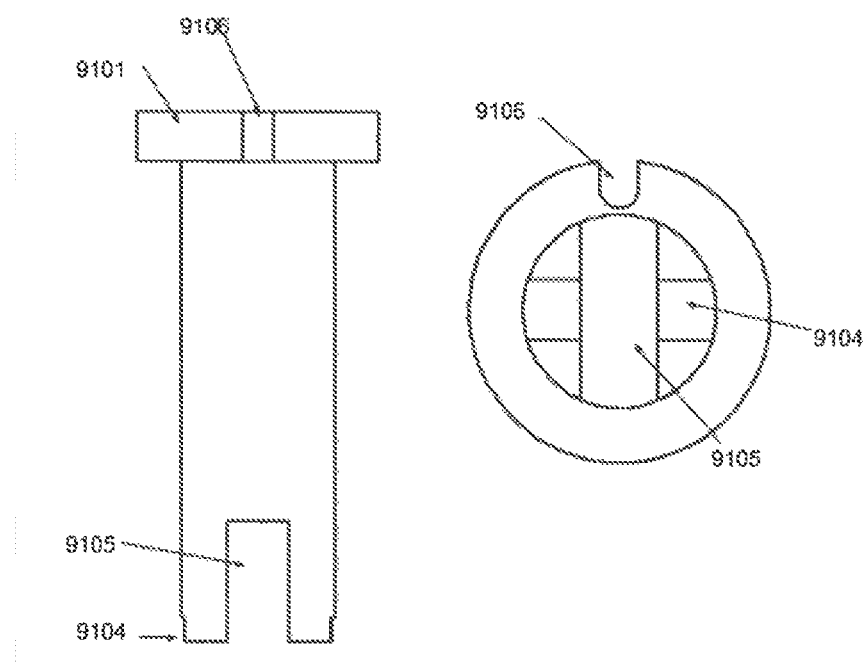
Figure 132:
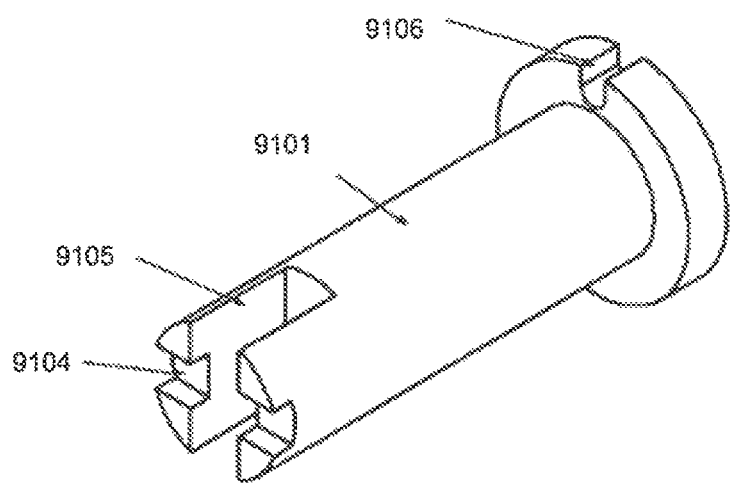

13.) While the auto-injector 1 is in the compressed configuration, the recoil torsion spring 8101 can be maintained in a wound state by another tensioner 9101 (see FIGS. 131-132) and retainer 9100. This recoil spring retainer 9100 may maintain the tensioned state of the recoil torsion spring 8101 during compression of the auto-injector 1 and injection of the dose. Note that the recoil spring 8101 may be disengaged from the needle barrel 4100 during uncoiling of the injection needle 4102. Following the expansion, after injection, the recoil spring 8101 can engage interference element 4107 of the needle barrel 4100 such that the injection needle 4102 is recoiled. This engagement 4107 of the recoiling spring 8101 on the needle barrel 4100 is facilitated by the axial movement of the needle barrel 4100 during the uncoiling process. To prevent the recoil torsion spring 8101 from unwinding (and recoiling the injection needle 4102 prematurely) once the uncoiling spring 8100 is disengaged from the needle barrel 4100, the trigger MC-106 actuates the recoil spring retainer 9100, such that full auto-injector 1 compression acts as a temporary spring retainer, until the expansion of the auto-injector 1.

14.) Once the auto-injector 1 is permitted to expand after the injection has been completed, the trigger MC-106 disengages, releasing the tensioner 9101 and allowing the recoil torsion spring 8101 to recoil the injection needle 4102 into the housing 1100, 2100. Subsequently an interlock SS-100 prevents the injection needle 4102 from being able to be deployed again.

The table below provides names and brief descriptions of the references numerals appearing in the figures:

| REFERENCE NUMERAL | NAME | DESCRIPTION |
|---|---|---|
| MDS-100 | RETAINER LOCKING MECHANISM | COMPLETE PART |
| MDS-101 | RETAINER LOCKING MECHANISM | TRIGGER CONTACT SURFACE |
| MDS-102 | RETAINER LOCKING MECHANISM | LOCK DISENGAGMENT SURFACE FOR TH |
| MDS-103 | RETAINER LOCKING MECHANISM | RETAINER CONTACT SURFACE |
| MDS-104 | RETAINER LOCKING MECHANISM | RETAINER SHEATH CONTACT SURFACE |
| MDS-200 | RETAINER KEEPER | COMPLETE PART |

| REFERENCE NUMERAL | NAME | DESCRIPTION |
|---|---|---|
| MDS-201 | RETAINER KEEPER | RETAINER STROKE HARD STOP |
| MDS-202 | RETAINER KEEPER | RETAINER ALIGNMENT RAILS |
| MDS-203 | RETAINER KEEPER | RESERVOIR ASSEMBLY TABS |
| MDS-204 | RETAINER KEEPER | RETAINER LOCK CONTACT SURFACE |
| MDS-300 | RETAINER LEFT HALF | COMPLETE PART |
| MDS-301 | RETAINER LEFT HALF | ASSEMBLY ALIGNMENT POST/HOLE |
| MDS-302 | RETAINER LEFT HALF | DISPENSING NEEDLE CHANNEL |
| MDS-303 | RETAINER LEFT HALF | FLEXIBLE TUBING CHANNEL |
| MDS-304 | RETAINER LEFT HALF | MOLDED FLEXIBLE TUBING CLAMPS |
| MDS-305 | RETAINER LEFT HALF | U-SONIC WELD ENERGY DIRECTORS |
| MDS-306 | RETAINER LEFT HALF | RETAINER LOCK CONTACT SURFACE |
| MDS-307 | RETAINER LEFT HALF | DISPENSING NEEDLE BARRIER LIP |
| MDS-308 | RETAINER LEFT HALF | DISPENSING SPRING SHOULDER |
| MDS-309 | RETAINER LEFT HALF | RETAINER KEEPER STROKE STOP CONTACT SURFACE |
| MDS-310 | RETAINER LEFT HALF | RETAINER TIP FOR PUSHING THE PLUNGER |
| MDS-400 | RETAINER RIGHT HALF | COMPLETE PART |
| MDS-401 | RETAINER RIGHT HALF | ASSEMBLY ALIGNMENT POST/HOLE |
| MDS-402 | RETAINER RIGHT HALF | DISPENSNIG NEEDLE CHANNEL |
| MDS-403 | RETAINER RIGHT HALF | FLEXIBLE TUBING CHANNEL |
| MDS-404 | RETAINER RIGHT HALF | MOLDED FLEXIBLE TUBING CLAMPS |
| MDS-405 | RETAINER RIGHT HALF | U-SONIC ENERGY DIRECTOR WELLS |
| MDS-406 | RETAINER RIGHT HALF | RETAINER LOCK CONTACT SURFACE |
| MDS-407 | RETAINER RIGHT HALF | DISPENSING NEEDLE BARRIER LIP |
| MDS-408 | RETAINER RIGHT HALF | DISPENSING SPRING SHOULDER |
| MDS-409 | RETAINER RIGHT HALF | RETAINER KEEPER STROKE STOP CONTACT SURFACE |
| MDS-410 | RETAINER RIGHT HALF | RETAINER TIP FOR PUSHING THE PLUNGER |
| MDS-500 | DISPENSING NEEDLE (CLEANLIESS) BARRIER | COMPLETE PART |
| MDS-501 | DISPENSING NEEDLE (CLEANLIESS) BARRIER | PLUNGER FACING SURFACE |
| MDS-502 | DISPENSING NEEDLE (CLEANLIESS) BARRIER | SEALING EDGE FOR RETAINER |
| MDS-600 | DISPENSING NEEDLE | COMPLETE PART |
| MDS-601 | DISPENSING NEEDLE | LANCET TIP |
| MDS-602 | DISPENSING NEEDLE | GRIT BLASTED SURFACE |
| MDS-603 | DISPENSING NEEDLE | HEEL DULLED AREA (TO PREVENT CORING) |
| MDS-604 | DISPENSING NEEDLE | PROXIMAL END OF NEEDLE |
| MDS-700 | DISPENSING SPRING | COMPLETE PART |
| MDS-701 | DISPENSING SPRING | RETAINER KEEPER CONTACT SURFACE |
| MDS-702 | DISPENSING SPRING | RETAINER SHOULDER CONTACT SURFACE |
| MDS-800 | MEDICAMENT RESERVOIR | COMPLETE PART |
| MDS-900 | PLUNGER | COMPLETE PART |
| MDS-901 | PLUNGER | TRIM EDGE (SEALING SURFACE) |
| MDS-902 | PLUNGER | DISPENSING NEEDLE BARRIER CONTACT SURFACE |
| NES-100 | NEEDLE SHEATH | COMPLETE PART |
| NES-101 | NEEDLE SHEATH | SNAP FIT EDGE FOR SAFETY MECHANISM |
| NES-102 | NEEDLE SHEATH | MOLD PIN SUPPORT WINDOWS |
| NES-103 | NEEDLE SHEATH | INJECTION NEEDLE GUIDE CUT OUT ON SNAP FIT EDGE |
| NES-104 | NEEDLE SHEATH | TOP CURVED CUT OUT FOR FITTING UP TO THE NEEDLE BARREL |
| NES-200 | NEEDLE BARREL | COMPLETE PART |
| NES-201 | NEEDLE BARREL | NEEDLE BARREL LOCK CUT OUT |
| NES-202 | NEEDLE BARREL | TORSION SPRING SLOT CUT |

-continued

| REFERENCE NUMERAL | NAME | DESCRIPTION |
|---|---|---|
| NES-203 | NEEDLE BARREL | FLEXIBLE TUBING CHANNEL CUT OUT (TO ALLOW FOR TUBING DEFLECTION DURING ROTATION) |
| NES-204 | NEEDLE BARREL | FLEXIBLE TUBING CONTACT SURFACE WHILE BEING ULTRASONICALLY WELDED |
| NES-205 | NEEDLE BARREL | MOLDED TUBING CLAMPS |
| NES-206 | NEEDLE BARREL | INJECTION NEEDLE CHANNEL CUT OUT WITH TEXTURED SURFACE |
| NES-207 | NEEDLE BARREL | NEEDLE BARREL CAP SHAFT RECEPTICAL |
| NES-208 | NEEDLE BARREL | ROTATIONAL ALIGNMENT RIDGE FOR BARREL GUIDE CONTACT |
| NES-209 | NEEDLE BARREL | INJECTION NEEDLE CHANNEL (COMPLETED CHANNEL FORMED AFTER WELDING) |
| NES-210 | NEEDLE BARREL | ULTRASONIC WELD STEP ON NEEDLE BARREL FACE |
| NES-300 | NEEDLE BARREL CAP | COMPLETE PART |
| NES-301 | NEEDLE BARREL CAP | HARD STOP CUT OUT |
| NES-302 | NEEDLE BARREL CAP | TORSION SPRING WINDING CUT OUT IN FACE OF NEEDLE BARREL CAP |
| NES-303 | NEEDLE BARREL CAP | FLEXIBLE TUBING CHANNEL CUT OUT (TO ALLOW FOR TUBING DEFLECTION DURING ROTATION) |
| NES-304 | NEEDLE BARREL CAP | FLEXIBLE TUBING CONTACT SURFACE WHILE BEING ULTRASONICALLY WELDED |
| NES-305 | NEEDLE BARREL CAP | MOLDED TUBING CLAMPS |
| NES-306 | NEEDLE BARREL CAP | INJECTION NEEDLE CHANNEL CUT OUT WITH TEXTURED SURFACE |
| NES-307 | NEEDLE BARREL CAP | ULTRASONIC WELD ENERGY DIRECTOR |
| NES-308 | NEEDLE BARREL CAP | NEEDLE BARREL CAP SHAFT |
| NES-309 | NEEDLE BARREL CAP | INJECTION NEEDLE CHANNEL (COMPLETED CHANNEL FORMED AFTER WELDING) |
| NES-400 | NEEDLE BARREL GUIDE | COMPLETE PART |
| NES-401 | NEEDLE BARREL GUIDE | NEEDLE BARREL LOCK CHANNEL |
| NES-402 | NEEDLE BARREL GUIDE | TORSION SPRING BRACE LEG CUT OUT |
| NES-403 | NEEDLE BARREL GUIDE | NEEDLE BARREL TAIL ROTATION STABILIZING HOLE |
| NES-404 | NEEDLE BARREL GUIDE | NEEDLE BARREL SHOULDER, FOR SETTING DEPTH OF NEEDLE BARREL IN THE GUIDE |
| NES-500 | NEEDEL BARREL LOCK | COMPLETE PART |
| NES-501 | NEEDEL BARREL LOCK | TRIGGER CONTACT SURFACE |
| NES-502 | NEEDEL BARREL LOCK | LOCK DISENGAGEMENT SURFACE FOR THE TOP HALF |
| NES-503 | NEEDEL BARREL LOCK | LOCKING DEPTH SHOULDER FOR THE NEEDLE BARREL GUIDE |
| NES-504 | NEEDEL BARREL LOCK | NEEDLE BARREL CONTACT SURFACE |
| NES-600 | NEEDLE SHEATH (CLEANLIENESS) BARRIER | COMPLETE PART |
| NES-601 | NEEDLE SHEATH (CLEANLIENESS) BARRIER | MOLDED RIBBING FOR PRESS FITTING IN NEEDLE SHEATH |
| NES-602 | NEEDLE SHEATH (CLEANLIENESS) BARRIER | TOP CURVED CUT OUT FOR FITTING UP TO THE NEEDLE BARREL |
| NES-700 | INJECTION NEEDLE | COMPLETE PART |
| NES-701 | INJECTION NEEDLE | DISTAL END/LANCET TIP |
| NES-702 | INJECTION NEEDLE | GRIT BLASTED SURFACE |
| NES-703 | INJECTION NEEDLE | PROXIMAL END |
| NES-800 | TORSION SPRING | COMPLETE PART |

-continued

| REFERENCE NUMERAL | NAME | DESCRIPTION |
|---|---|---|
| NES-801 | TORSION SPRING | ROTATIONAL LEG MAKING CONTACT WITH THE NEEDLE BARREL |
| NES-802 | TORSION SPRING | BRACING LEG (SUPPORTED ON THE NEEDLE BARREL GUIDE) |
| NES-900 | FLEXIBLE TUBING | COMPLETE PART |
| SS-100 | AUTO-INJECTOR INTERLOCK | COMPLETE PART |
| SS-101 | AUTO-INJECTOR INTERLOCK | LOCKOUT ENGAGMENT ARM |
| SS-102 | AUTO-INJECTOR INTERLOCK | KICK BACK FOOT |
| SS-103 | AUTO-INJECTOR INTERLOCK | SLANTED FOOT FOR LOCKOUT |
| SS-200 | SAFETY MECHANISM | COMPLETE PART |
| SS-201 | SAFETY MECHANISM | TAPERED LEAD IN EDGE FOR NEEDLE SHEATH |
| SS-202 | SAFETY MECHANISM | ALIGNMENT PROTRUSIONS FOR ASSEMBLY (FIT IN GRABBER UNDECUTS) |
| SS-203 | SAFETY MECHANISM | NEEDLE SHEATH HOLE |
| SS-204 | SAFETY MECHANISM | LOCKING POST |
| SS-300 | EXPANSION SPRING | COMPLETE PART |
| SS-301 | EXPANSION SPRING | CONTACT SURFACE FOR BOTTOM HALF |
| SS-302 | EXPANSION SPRING | CONTACT SURFACE FOR COVER |
| MC-100 | COVER | COMPLETE PART |
| MC-101 | COVER | EXPANSION SLOTS FOR ASSEMBLY |
| MC-102 | COVER | ASSEMBLY ALIGNMENT CHANNELS FOR EXPANSION TABS ON THE BOTTOM HALF |
| MC-103 | COVER | ROTATIONAL CHANNEL FOR THE EXPANSION TABS ON THE BOTTOM HALF |
| MC-104 | COVER | EJECTOR PIN LOCATIONS |
| MC-105 | COVER | ALIGNMENT POSTS FOR THE BOTTOM HALF DURING INJECTION |
| MC-106 | COVER | RETAINER TRIGGER |
| MC-107 | COVER | NEEDLE BARREL LOCK TRIGGER |
| MC-108 | COVER | EXPANSION SPRING RECESS CUT |
| MC-109 | COVER | PUCK STOPPER GRABBER CONTACT SURFACE FOR THE STOPPER |
| MC-110 | COVER | INJECTION NEEDLE GUIDE |
| MC-111 | COVER | NEEDLE SHEATH HOLE |
| MC-112 | COVER | INJECTION NEEDLE HOLE |
| MC-113 | COVER | INJECTION NEEDLE GUIDE TAPERED UNDERCUT TO PREVENT PLASTIC SCORING |
| MC-114 | COVER | GRABBER UNDERCUT HOLE FOR THE SAFETY COVER PROTRUSIONS |
| MC-115 | COVER | WALL CUT AWAY FOR STOPPER CLEARANCE |
| MC-116 | COVER | PERIMETER WALL CUT TO PREVENT DEFORMATION DURING MOLDING |
| MC-117 | COVER | STORED/LOCKED POSITION |
| MC-118 | COVER | UNLOCKED POSITION |
| MC-119 | COVER | ARMED POSITION |
| MC-120 | COVER | INJECTION POSITION |
| MC-121 | COVER | INJECTION SURFACE |
| MC-200 | BOTTOM HALF | COMPLETE PART |
| MC-201 | BOTTOM HALF | HOUSINGS FOR PUCK STOPPERS |
| MC-202 | BOTTOM HALF | HOUSINGS FOR TRIGGERS AND ALIGNMENT POSTS (DURING STORED STATE) |
| MC-203 | BOTTOM HALF | TRIGGER HOLES |
| MC-204 | BOTTOM HALF | NEEDLE SHEATH HOLE |
| MC-205 | BOTTOM HALF | RETAINER KEEPER RECESS CUT |
| MC-206 | BOTTOM HALF | RESERVOIRCUT OUT/ RESERVOIRCRADDLE |

-continued

| REFERENCE NUMERAL | NAME | DESCRIPTION |
|---|---|---|
| MC-207 | BOTTOM HALF | NEEDLE BARREL CRADLE |
| MC-208 | BOTTOM HALF | RESERVOIR BRACING WALL |
| MC-209 | BOTTOM HALF | ASSEMBLY FINS FOR TOP HALF |
| MC-210 | BOTTOM HALF | ROTATION/EXPANSION TABS |
| MC-211 | BOTTOM HALF | ALIGNMENT POST HOUSINGS FOR INJECTION |
| MC-212 | BOTTOM HALF | PUCK STOPPER LEDGE FOR DEVICE LOCK OUT |
| MC-213 | BOTTOM HALF | EXPANSION SPRING RECESS CUT OUT |
| MC-214 | BOTTOM HALF | INJECTION NEEDLE GUIDE CUT OUT |
| MC-215 | BOTTOM HALF | PUCK SEALING SURFACE WITH TEXTURED PROFILE |
| MC-216 | BOTTOM HALF | NEEDLE BARREL GUIDE PLATFORM |
| MC-217 | BOTTOM HALF | KEYED SLOT FOR SAFETY PLATE |
| MC-218 | BOTTOM HALF | HARD STOP FOR NEEDLE BARREL ROTATION |
| MC-219 | BOTTOM HALF | TIRGGER BRACING |
| MC-300 | TOP HALF | COMPLETE PART |
| MC-301 | TOP HALF | FINGER PLACEMENT LOCATIONS (FOR ROTATION) |
| MC-302 | TOP HALF | RIDGE ON TOP SURFACE FOR NEEDLE BARREL GUIDE AND ROTATIONAL AID |
| MC-303 | TOP HALF | ASSEMBLY FIN CUT OUTS FOR BOTTOM HALF |
| MC-304 | TOP HALF | RESERVOIR CUT OUT/CRADLE FOR VIAL |
| MC-305 | TOP HALF | CUT OUT FOR THE RETAINER KEEPER |
| MC-306 | TOP HALF | RETAINER LOCK DISENGAGEMENT RAMP |
| MC-307 | TOP HALF | NEEDLE BARREL LOCK DISENGAGEMENT RAMP |
| MC-308 | TOP HALF | EJECTOR PIN LOCATION ON NEEDLE BRACE |
| MC-309 | TOP HALF | INJECTION NEEDLE BRACE |
| MC-310 | TOP HALF | FLEXIBLE TUBING CUT OUT FOR ROTATING AROUND THE NEEDLE BARREL |
| MC-311 | TOP HALF | RESERVOIR BRACING WALL |
| MC-312 | TOP HALF | NEEDLE BARREL LEDGE CUT (KEEPS THE NEEDLE BARREL INSIDE THE GUIDE DURING ROTATION BY PREVENTING AXIAL DISPLACEMENT) |
| MC-313 | TOP HALF | NEEDLE BARREL GUIDE CUT OUT |
| MC-314 | TOP HALF | PUCK STOPPER HOUSINGS |
| MC-315 | TOP HALF | PUCK SEALING SURFACE/RIM |
| MC-316 | TOP HALF | NEEDLE BARREL TAIL CUT OUT |
| 1 | AUTOINJECTOR ASSEMBLY | FULL ASSEMBLY INCLUDING THE COVER |
| 1100 | TOP HALF | TOP HALF |
| 1101 | TOP HALF | FINGER TAB |
| 1102 | TOP HALF | ASSEMBLY ALIGNMENT HOLES |
| 1103 | TOP HALF | MALE THREAD FOR HELIX |
| 1104 | TOP HALF | MIDDLE HOUSING |
| 1105 | TOP HALF | RESERVOIR RECESS CUT TOP HALF |
| 1106 | TOP HALF | RECOILING SPRING CUTOUT |
| 1107 | TOP HALF | RESERVOIR CRADLE HOUSING SIDE |
| 1108 | TOP HALF | RESERVOIR CRADLE OUTSIDE EDGE |
| 1109 | TOP HALF | RETAINER GUIDE HOUSING |
| 2100 | BOTTOM HALF | BOTTOM HALF |
| 2101 | BOTTOM HALF | ASSEMBLY ALIGNMENT PYRAMIDS |
| 2102 | BOTTOM HALF | MIDDLE HOUSING |
| 2103 | BOTTOM HALF | MALE THREAD FOR HELIX ALIGNMENT |

-continued

| REFERENCE NUMERAL | NAME | DESCRIPTION |
|---|---|---|
| 2104 | BOTTOM HALF | RESERVOIRRECESS CUT BOTTOM HALF |
| 2105 | BOTTOM HALF | RESERVOIRCRADDLE HOUSING SIDE |
| 2106 | BOTTOM HALF | RESERVOIRCRADDLE OUTSIDE EDGE |
| 2107 | BOTTOM HALF | EXPANSION TABS |
| 2108 | BOTTOM HALF | RESERVOIRREAR BRACE BOTTOM HALF |
| 2109 | BOTTOM HALF | UNCOILING SPRING BRACE |
| 2110 | BOTTOM HALF | HELIX LOCK GUIDE CHANNEL |
| 2111 | BOTTOM HALF | INJECTION NEEDLE HOLE IN BOTTOM HALF |
| 2112 | BOTTOM HALF | RETAINER GUIDE HOUSING |
| 2113 | BOTTOM HALF | RECOIL LOCK ALIGNMENT SLOTS |
| 3100 | COVER | COVER WITH MOLDED SPRINGS |
| 3101 | COVER | MOLDED SPRINGS |
| 3102 | COVER | STORED/COLLAPSED CONFIGURATION POSITION |
| 3103 | COVER | ACTIVATED CONFIGURATION POSTION |
| 3104 | COVER | ARMED CONFIGURATION POSITION |
| 3105 | COVER | ASSEMBLY SHOULDER IN COVER FOR REACHING STORED POSITION |
| 3106 | COVER | EXPANSION CHANNEL IN COVER |
| 3107 | COVER | STORED/COLLAPSED POSITION LOCK |
| 3108 | COVER | ACTIVE TO ARMED LOCK |
| 4100 | NEEDLE BARREL | HELIX |
| 4101 | NEEDLE BARREL | NEEDLE BARREL WITH SLANTED CHANNEL |
| 4102 | NEEDLE BARREL | COILED NEEDLE |
| 4103 | NEEDLE BARREL | COILED NEEDLE COLLAR |
| 4104 | NEEDLE BARREL | UNCOILING TENSIONER |
| 4105 | NEEDLE BARREL | UNCOILING TENSIONER LOBED HEAD |
| 4106 | NEEDLE BARREL | UNCOILING TORSIONAL SPRING SLOT IN HELIX |
| 4107 | NEEDLE BARREL | RECOILING SPRING SLOT IN HELIX |
| 4108 | NEEDLE BARREL | NEEDLE BARREL WITH SLANT CUT TORSIONAL SPRING SLOT |
| 4109 | NEEDLE BARREL | UNCOILING TENSIONER SQUARE HOLE FOR WINDING |
| 4110 | NEEDLE BARREL | SLANTED CHANNEL NEEDLE BARREL THRUST BEARING |
| 4111 | NEEDLE BARREL | SLANTED CHANNEL INJECTION NEEDLE GUIDE CHANNEL |
| 4112 | NEEDLE BARREL | NEEDLE COLLAR SLOT IN HELIX |
| 4113 | NEEDLE BARREL | NEEDLE GUIDE GROOVE IN HELIX |
| 4114 | NEEDLE BARREL | UNCOILING TENSIONER TORSIONAL SPRING SLOT |
| 5100 | NEEDLE BARREL LOCK | HELIX LOCK |
| 5101 | NEEDLE BARREL LOCK | SLANTED CUT FOR TRIGGER |
| 5102 | NEEDLE BARREL LOCK | SLANTED CUT HELIX SIDE |
| 7100 | MEDICAMENT RESERVOIR & ASSEMBLY | VIAL |
| 7101 | MEDICAMENT RESERVOIR & ASSEMBLY | RETAINER |
| 7102 | MEDICAMENT RESERVOIR & ASSEMBLY | PLUNGER |
| 7103 | MEDICAMENT RESERVOIR & ASSEMBLY | SHEATH |
| 7104 | MEDICAMENT RESERVOIR & ASSEMBLY | RESERVOIR MOLDED IN 90 DEGREE ELBOW TIP |
| 7105 | MEDICAMENT RESERVOIR & ASSEMBLY | PLUNGER MOLDED RECEPTICLE FOR RETAINER |
| 7106 | MEDICAMENT RESERVOIR & ASSEMBLY | DISPENSING SPRING |

-continued

| REFERENCE NUMERAL | NAME | DESCRIPTION |
|---|---|---|
| 7107 | MEDICAMENT RESERVOIR & ASSEMBLY | RETAINER TIP FOR PLUNGER |
| 7108 | MEDICAMENT RESERVOIR & ASSEMBLY | RETAINER SHOULDER FOR GRABBING SHEATH/DISPENSING SPRING |
| 7109 | MEDICAMENT RESERVOIR & ASSEMBLY | RETAINER SHOULDER FOR PLUNGER |
| 7110 | MEDICAMENT RESERVOIR & ASSEMBLY | RETAINER RELEASE TABS |
| 8100 | TORSION SPRING | UNCOILING TORSIONAL SPRING |
| 8101 | TORSION SPRING | RECOILING TORSIONAL SPRING |
| 8102 | TORSION SPRING | UNCOILING TORSIONAL SPRING ANTI-ROTATIONAL TAIL |
| 8103 | TORSION SPRING | UNCOILING TORSIONAL SPRING HELIX END |
| 8104 | TORSION SPRING | RECOILING TORSIONAL SPRING ANTI-ROTATIONAL TAIL |
| 8105 | TORSION SPRING | RECOILING TORSIONAL SPRING HELIX END |
| 9100 | RECOIL SYSTEM | RECOIL LOCK |
| 9101 | RECOIL SYSTEM | RECOILING SPRING TENSIONER |
| 9102 | RECOIL SYSTEM | RECOIL LOCK LIVING HINGE |
| 9103 | RECOIL SYSTEM | RECOIL LOCK ALIGNMENT SLOTS |
| 9104 | RECOIL SYSTEM | RECOILING TENSIONER SLOT FOR WINDING |
| 9105 | RECOIL SYSTEM | RECOILING TENSIONER SLOT FOR LOCKING |
| 9106 | RECOIL SYSTEM | RECOILING TENSIONER TORSION SPRING SLOT |
| 9107 | RECOIL SYSTEM | RECOIL LOCK NEEDLE BARREL PIECE |

Each numerical value presented herein is contemplated to represent an exemplary minimum value or a maximum value in a range for a corresponding parameter. Accordingly, when added to the claims, the exemplary values provide express support for claiming the range, which may lie above or below the numerical value, in accordance with the teachings herein. Every value between the minimum value and the maximum value within each numerical range presented herein (including in the chart shown in FIG. 141), is contemplated and expressly supported herein, subject to the number of significant digits expressed in each particular range.

The terms and expressions employed herein are used as terms and expressions of description and not of limitation and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The structural features and functions of some embodiments may be arranged in various combinations and permutations, and all are considered to be within the scope of the disclosed invention. Unless otherwise necessitated, recited steps in the various methods may be performed in any order and certain steps may be performed substantially simultaneously. Accordingly, the described embodiments are to be considered in all respects as only illustrative and not restrictive. Furthermore, the configurations described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A compact, high aspect ratio auto-injector for delivering a medicament dose subcutaneously or intramuscularly, the auto-injector comprising:
  a housing;
  a medicament dispensing system disposed within the housing and comprising a medicament reservoir adapted to contain the dose; and
  a needle extension mechanism coupled to the medicament reservoir, the needle extension mechanism comprising a curved injection needle and a needle guide adapted to straighten the curved injection needle during deployment of the curved injection needle through the needle guide, such that the curved injection needle is non-self-straightening and is straightened by the needle guide, to facilitate dispensing of the dose by the auto-injector.

2. The auto-injector according to claim 1, wherein the housing comprises a sealed housing rotatably retained in a cover.

3. The auto-injector according to claim 2, where the housing further comprises an interface to receive user input to facilitate a manual rotation of the housing relative to the cover from a first locked position to a second unlocked position.

4. The auto-injector according to claim 3, wherein at least one of the housing, the cover, a label, and a component directly visible to a user comprises indicia indicating the locked position, the unlocked position, and an armed position.

5. The auto-injector according to claim 3, wherein the auto-injector further comprises a biasing member, such that when the housing is rotated to the unlocked position, the sealed housing is automatically displaced axially relative to the cover, increasing a height of the auto-injector.

6. The auto-injector according to claim 5, wherein the biasing member comprises a spring that is at least one of integrally formed with the housing integrally formed with the cover, and disposed between the housing and the cover.

7. The auto-injector according to claim 5, wherein the auto-injector further comprises an interlock, such that the housing cannot be rotated relative to the cover or displaced axially relative to the cover without removal of the interlock.

8. The auto-injector according to claim 5, wherein manual compression of the auto-injector in an armed position, reduces the height of the auto-injector, and activates a mechanism that straightens and extends a distal end of the curved injection needle through the housing, dispenses the dose through the curved injection needle, and activates an interlock.

9. The auto-injector according to claim 8, wherein upon release of the manual compression, the biasing member automatically displaces the housing axially relatively to the cover, increasing the height of the auto-injector and retracting the distal end of the curved injection needle into the housing.

10. The auto-injector according to claim 9, wherein the auto-injector further comprises an interlock to prevent subsequent manual compression of the auto-injector, thereby rendering the auto-injector single-use.

11. The auto-injector according to claim 10, wherein the interlock comprises an abutting structure in the housing and the cover.

12. The auto-injector according to claim 1, wherein the medicament dispensing system further comprises a plunger within the medicament reservoir and forming a sealed cavity for retaining the dose.

13. The auto-injector according to claim 12, wherein the medicament dispensing system further comprises a dispensing needle in fluidic communication with the curved injection needle.

14. The auto-injector according to claim 13, further comprising a flexible tube interconnecting the dispensing needle with the curved injection needle.

15. The auto-injector according to claim 13, wherein the medicament dispensing system further comprises a spring, a retainer, and a locking mechanism such that when the locking mechanism is released, the spring displaces the retainer and forces the dispensing needle to pierce the plunger to provide fluidic communication with the dose.

16. The auto-injector according to claim 15, wherein the cover comprises a second trigger to release the retainer and the locking mechanism.

17. The auto-injector according to claim 15, wherein the spring further displaces the plunger to pump the dose out of the vial and through the dispensing needle to the curved injection needle.

18. The auto-injector according to claim 15, wherein the spring comprises a compression spring.

19. The auto-injector according to claim 1, wherein the needle extension mechanism further comprises a needle barrel for supporting the curved injection needle, a spring coupled to the barrel for rotating the barrel to uncoil the curved injection needle, and a barrel locking mechanism to prevent inadvertent rotation of the barrel.

20. The auto-injector according to claim 19, wherein the spring comprises a torsion spring.

21. The auto-injector according to claim 19, wherein a cover of the housing forms an aperture aligned with the needle guide through which a distal end of the curved injection needle passes during rotation of the barrel.

22. The auto-injector according to claim 21, wherein release of the barrel locking mechanism permits the spring to rotate the barrel and deploy the curved injection needle.

23. The auto-injector according to claim 22, wherein the cover comprises a first trigger to release the barrel locking mechanism.

24. The auto-injector according to claim 19, wherein the needle extension mechanism further comprises a needle barrel cap to secure a proximal end of the curved injection needle to the needle barrel.

25. A method of operating a compact, high aspect ratio auto-injector for delivering a medicament dose subcutaneously or intramuscularly, the autoinjector comprising a housing, a medicament dispensing system disposed in the housing and comprising a medicament reservoir adapted to contain the dose, and a needle extension mechanism coupled to the medicament reservoir, the needle extension mechanism comprising a curved injection needle and a needle guide, the method comprising the steps of:
triggering deployment of a distal end of the curved injection needle through an aperture in a cover of the housing aligned with the needle guide to straighten the curved injection needle, wherein the curved injection needle is non-self-straightening and is straightened by the needle guide;
triggering piercing of the medicament reservoir to provide fluidic communication between the medicament reservoir and the curved injection needle;
dispensing the dose through the curved injection needle at a desired injection location; and thereafter, retracting the distal end of the curved injection needle into the auto-injector.

26. The method according to claim 25, wherein the auto-injector further comprises an interlock, such that the housing cannot be rotated relative to the cover or displaced axially relative to the cover without removal of the interlock.

27. The method according to claim 25, wherein the housing comprises a sealed housing rotatably retained in the cover, the method further comprising the steps of:
manually rotating the housing relative to the cover from a first locked position to a second unlocked position, in which the sealed housing is automatically displaced axially relative to the cover to an armed position, increasing a height of the auto-injector.

28. The method according to claim 27, further comprising the step of determining the locked position, the unlocked position, and the armed position based on indicia on at least one of the housing, the cover, a label, and a component directly visible to a user.

29. The method according to claim 27, further comprising the step of adhering the cover to the desired injection location prior to triggering of the auto-injector.

30. The method according to claim 25, wherein the step of triggering piercing of the medicament reservoir comprises manually compressing the auto-injector when the auto-injector is in the armed position, which comprises activating the medicament dispensing mechanism triggering piercing of a plunger within the medicament reservoir with a distal end of a dispensing needle.

* * * * *